(12) United States Patent
Melker et al.

(10) Patent No.: US 7,914,460 B2
(45) Date of Patent: Mar. 29, 2011

(54) CONDENSATE GLUCOSE ANALYZER

(75) Inventors: Richard J. Melker, Gainesville, FL (US); David G. Bjoraker, Gainesville, FL (US); Donn M. Dennis, Gainesville, FL (US); Jon D. Stewart, Gainesville, FL (US); Christopher D. Batich, Gainesville, FL (US); Matthew M. Booth, Gainesville, FL (US); John Frederick Horn, Jr., Orange Park, FL (US); Ronald E. Youngblood, Williston, FL (US)

(73) Assignees: University of Florida Research Foundation, Inc., Gainesville, FL (US); Xhale, Inc., Gainesville, FL (US)

( * ) Notice: Subject to any disclaimer, the term of this patent is extended or adjusted under 35 U.S.C. 154(b) by 0 days.

(21) Appl. No.: 11/504,335

(22) Filed: Aug. 15, 2006

(65) Prior Publication Data
US 2008/0045825 A1  Feb. 21, 2008

(51) Int. Cl.
*A61B 5/08* (2006.01)
*A61B 5/00* (2006.01)
(52) U.S. Cl. ......... 600/532; 600/365; 600/529; 600/543
(58) Field of Classification Search .................. 600/365, 600/532, 543
See application file for complete search history.

(56) References Cited

U.S. PATENT DOCUMENTS

| | | | |
|---|---|---|---|
| 3,567,029 A | 3/1971 | Quame | |
| 3,608,546 A | 9/1971 | Shinn | |
| 3,649,199 A | 3/1972 | Littlejohn | |
| 3,792,272 A | 2/1974 | Harte et al. | |
| 3,877,291 A | 4/1975 | Hoppesch et al. | |
| 3,951,607 A | 4/1976 | Fraser | |
| 3,955,926 A | 5/1976 | Fischer | |
| 4,150,670 A | 4/1979 | Jewett et al. | |
| 4,202,352 A | 5/1980 | Osborn | |
| 4,215,409 A | 7/1980 | Strowe | |
| 4,312,228 A | 1/1982 | Wohltjen | |
| 4,314,564 A | 2/1982 | Albarda | |
| 4,334,540 A | 6/1982 | Preti et al. | |
| 4,346,584 A | 8/1982 | Boehringer | |
| 4,349,626 A | 9/1982 | Labows et al. | |
| 4,361,026 A | 11/1982 | Muller et al. | |
| 4,399,686 A | 8/1983 | Kindlund et al. | |
| 4,432,226 A | 2/1984 | Dempster | |
| 4,456,014 A | 6/1984 | Buck et al. | |

(Continued)

FOREIGN PATENT DOCUMENTS

DE    19 607 646    9/1997

(Continued)

OTHER PUBLICATIONS

Effros et al. "Dilution of Respiratory Solutes in Exhaled Condensates". Am J Respir Crit Care Med. vol. 165, pp. 661-669, 2002.*

(Continued)

*Primary Examiner* — Patricia C Mallari
(74) *Attorney, Agent, or Firm* — Timothy H. Van Dyke; Beusse Wolter Sanks Mora & Maire

(57) ABSTRACT

The present invention provides systems and methods for analyzing glucose present in exhaled breath condensate (EBC). In certain embodiments of the invention, electrochemical- or coulometric-based sensing technologies are used to analyze EBC for the presence and/or concentration of glucose.

33 Claims, 7 Drawing Sheets

U.S. PATENT DOCUMENTS

| | | |
|---|---|---|
| 4,534,360 A | 8/1985 | Williams |
| 4,734,777 A | 3/1988 | Okino et al. |
| 4,735,777 A | 4/1988 | Mitsui et al. |
| 4,772,559 A | 9/1988 | Preti et al. |
| 4,796,639 A | 1/1989 | Snow et al. |
| 4,868,545 A | 9/1989 | Jones |
| 4,895,017 A | 1/1990 | Pyke et al. |
| 4,938,928 A | 7/1990 | Koda et al. |
| 4,992,244 A | 2/1991 | Grate |
| 5,003,985 A | 4/1991 | White et al. |
| 5,034,192 A | 7/1991 | Wrighton et al. |
| 5,042,501 A | 8/1991 | Kenny et al. |
| 5,060,506 A | 10/1991 | Douglas |
| 5,071,770 A | 12/1991 | Kolesar, Jr. |
| 5,081,871 A | 1/1992 | Glaser |
| 5,082,630 A | 1/1992 | Partin et al. |
| 5,094,235 A | 3/1992 | Westenskow et al. |
| 5,111,827 A | 5/1992 | Rantala |
| 5,137,692 A | 8/1992 | Fritz |
| 5,145,645 A | 9/1992 | Zakin et al. |
| 5,167,972 A | 12/1992 | Greenberg et al. |
| 5,179,027 A | 1/1993 | Fisher |
| 5,252,292 A | 10/1993 | Hirata et al. |
| 5,296,706 A | 3/1994 | Braig et al. |
| 5,303,575 A | 4/1994 | Brown et al. |
| 5,317,156 A | 5/1994 | Cooper et al. |
| 5,325,704 A | 7/1994 | Mariani et al. |
| 5,351,522 A | 10/1994 | Lura |
| 5,360,009 A * | 11/1994 | Herskovitz .................... 600/538 |
| 5,361,771 A | 11/1994 | Craine et al. |
| 5,409,839 A | 4/1995 | Balestrieri et al. |
| 5,425,374 A | 6/1995 | Ueda et al. |
| 5,447,165 A | 9/1995 | Gustafsson |
| 5,453,359 A | 9/1995 | Gargan et al. |
| 5,465,608 A | 11/1995 | Lokshin et al. |
| 5,466,700 A | 11/1995 | Batenhorst et al. |
| 5,482,601 A | 1/1996 | Ohshima et al. |
| 5,495,744 A | 3/1996 | Ueda et al. |
| 5,501,212 A | 3/1996 | Psaros |
| 5,528,924 A | 6/1996 | Wajid et al. |
| 5,547,878 A | 8/1996 | Kell |
| 5,558,083 A | 9/1996 | Bathe et al. |
| 5,560,352 A | 10/1996 | Heim et al. |
| 5,571,401 A | 11/1996 | Lewis et al. |
| 5,573,005 A | 11/1996 | Ueda et al. |
| 5,573,955 A | 11/1996 | Khanna et al. |
| 5,605,612 A | 2/1997 | Park et al. |
| 5,634,517 A | 6/1997 | Linden et al. |
| 5,645,072 A | 7/1997 | Thrall et al. |
| 5,716,852 A | 2/1998 | Yager et al. |
| 5,756,879 A | 5/1998 | Yamagishi et al. |
| 5,771,890 A | 6/1998 | Tamada |
| 5,776,783 A | 7/1998 | Kell |
| 5,783,154 A | 7/1998 | Althainz et al. |
| 5,783,449 A | 7/1998 | Kuznetsov |
| 5,795,787 A | 8/1998 | Silkoff et al. |
| 5,801,297 A | 9/1998 | Mifsud et al. |
| 5,826,577 A | 10/1998 | Perroz et al. |
| 5,830,412 A | 11/1998 | Kimura et al. |
| 5,861,254 A | 1/1999 | Schneider et al. |
| 5,866,434 A | 2/1999 | Massey et al. |
| 5,891,398 A | 4/1999 | Lewis et al. |
| 5,900,552 A | 5/1999 | Chu et al. |
| 5,918,257 A | 6/1999 | Mifsud et al. |
| 5,925,014 A | 7/1999 | Teeple Jr. |
| 5,928,167 A | 7/1999 | Wagner et al. |
| 5,932,877 A | 8/1999 | Braig et al. |
| 5,945,069 A | 8/1999 | Buehler |
| 5,950,630 A | 9/1999 | Portwood et al. |
| 5,954,685 A | 9/1999 | Tierney |
| 5,958,896 A | 9/1999 | Renshaw et al. |
| 5,962,335 A | 10/1999 | Katzman |
| 5,964,712 A | 10/1999 | Kubo et al. |
| 5,971,937 A | 10/1999 | Ekström |
| 5,996,586 A | 12/1999 | Phillips |
| 6,007,775 A | 12/1999 | Yager |
| 6,010,459 A | 1/2000 | Silkoff et al. |
| 6,025,200 A | 2/2000 | Kaish et al. |
| 6,057,162 A | 5/2000 | Rounbehler et al. |
| 6,063,243 A | 5/2000 | Zettl et al. |
| 6,067,167 A | 5/2000 | Atkinson et al. |
| 6,074,345 A | 6/2000 | Van Oostrom et al. |
| 6,085,576 A | 7/2000 | Sunshine et al. |
| 6,094,681 A | 7/2000 | Shaffer et al. |
| 6,097,485 A | 8/2000 | Lievan |
| 6,120,443 A | 9/2000 | Cohen-Laroque |
| 6,131,571 A | 10/2000 | Lampotang et al. |
| 6,136,801 A | 10/2000 | Kell |
| 6,153,147 A | 11/2000 | Craig |
| 6,180,414 B1 | 1/2001 | Katzman |
| 6,186,977 B1 | 2/2001 | Andrews et al. |
| 6,190,858 B1 | 2/2001 | Persaud et al. |
| 6,203,814 B1 | 3/2001 | Fisher et al. |
| 6,216,690 B1 | 4/2001 | Keitel et al. |
| 6,221,026 B1 | 4/2001 | Phillips |
| 6,234,006 B1 | 5/2001 | Sunshine et al. |
| 6,237,397 B1 | 5/2001 | Shinar et al. |
| 6,244,096 B1 | 6/2001 | Lewis et al. |
| 6,248,078 B1 | 6/2001 | Risby et al. |
| 6,251,082 B1 | 6/2001 | Rayburn |
| 6,261,783 B1 | 7/2001 | Jayasena et al. |
| 6,264,913 B1 | 7/2001 | Wagner |
| 6,277,081 B1 | 8/2001 | Susi et al. |
| 6,283,953 B1 | 9/2001 | Ayer et al. |
| 6,287,765 B1 | 9/2001 | Cubicciotti |
| 6,303,316 B1 | 10/2001 | Kiel et al. |
| 6,305,212 B1 | 10/2001 | Drzewiecki |
| 6,312,390 B1 | 11/2001 | Phillips |
| 6,319,724 B1 | 11/2001 | Lewis et al. |
| 6,328,708 B1 | 12/2001 | Georgieff |
| 6,341,520 B1 | 1/2002 | Satoh et al. |
| 6,363,772 B1 | 4/2002 | Berry |
| 6,387,329 B1 | 5/2002 | Lewis et al. |
| 6,399,302 B1 | 6/2002 | Lannigan et al. |
| 6,416,479 B1 | 7/2002 | Seidman |
| 6,416,740 B1 | 7/2002 | Unger |
| 6,455,319 B1 | 9/2002 | Lewis et al. |
| 6,467,333 B2 | 10/2002 | Lewis et al. |
| 6,479,019 B1 | 11/2002 | Goldstein et al. |
| 6,495,824 B1 | 12/2002 | Atkinson |
| 6,511,453 B2 | 1/2003 | Georgieff |
| 6,546,268 B1 * | 4/2003 | Ishikawa et al. ............... 600/345 |
| 6,558,626 B1 | 5/2003 | Aker et al. |
| 6,585,661 B1 * | 7/2003 | Hunt et al. .................... 600/532 |
| 6,589,727 B1 | 7/2003 | Klenerman et al. |
| 6,597,438 B1 | 7/2003 | Cabuz et al. |
| 6,598,459 B1 | 7/2003 | Fu |
| 6,599,253 B1 | 7/2003 | Baum et al. |
| 6,599,281 B1 | 7/2003 | Struys et al. |
| 6,620,800 B1 | 9/2003 | Roberts, II |
| 6,631,333 B1 | 10/2003 | Lewis et al. |
| 6,680,377 B1 | 1/2004 | Stanton et al. |
| 6,727,075 B2 | 4/2004 | Fitzgerald et al. |
| 6,755,783 B2 | 6/2004 | Cosentino et al. |
| RE38,728 E | 4/2005 | Katzman et al. |
| 2001/0021815 A1 | 9/2001 | Katzman et al. |
| 2001/0041366 A1 | 11/2001 | Lewis et al. |
| 2001/0046674 A1 | 11/2001 | Ellington |
| 2001/0050228 A1 | 12/2001 | Jaeger |
| 2001/0055544 A1 | 12/2001 | Copp |
| 2002/0007249 A1 | 1/2002 | Cranley et al. |
| 2002/0007687 A1 | 1/2002 | Zimmermann et al. |
| 2002/0014236 A1 | 2/2002 | Dittmann et al. |
| 2002/0017300 A1 | 2/2002 | Hickle et al. |
| 2002/0026937 A1 | 3/2002 | Mault |
| 2002/0034757 A1 | 3/2002 | Cubicciotti |
| 2002/0068295 A1 | 6/2002 | Madou et al. |
| 2002/0173729 A1 | 11/2002 | Viertio-Oja et al. |
| 2002/0177232 A1 | 11/2002 | Melker et al. |
| 2003/0004426 A1 | 1/2003 | Melker et al. |
| 2003/0008407 A1 | 1/2003 | Fu |
| 2003/0059820 A1 | 3/2003 | Vo-Dinh |
| 2003/0087239 A1 | 5/2003 | Stanton et al. |
| 2003/0119065 A1 | 6/2003 | Lin et al. |
| 2003/0139681 A1 | 7/2003 | Melker et al. |
| 2003/0176804 A1 | 9/2003 | Melker et al. |
| 2003/0185760 A1 | 10/2003 | Lanza et al. |

| | | | |
|---|---|---|---|
| 2003/0216660 | A1 | 11/2003 | Ben-Oren et al. |
| 2004/0027246 | A1 | 2/2004 | Aguglia |
| 2004/0038386 | A1 | 2/2004 | Zesch et al. |
| 2004/0101477 | A1 | 5/2004 | Leyland-Jones |
| 2004/0127808 | A1* | 7/2004 | Vaughan et al. ............... 600/532 |
| 2004/0162500 | A1 | 8/2004 | Kline |
| 2004/0236244 | A1 | 11/2004 | Allen et al. |
| 2005/0037374 | A1 | 2/2005 | Melker et al. |
| 2005/0054942 | A1 | 3/2005 | Melker et al. |
| 2005/0065446 | A1 | 3/2005 | Talton |
| 2005/0137491 | A1 | 6/2005 | Paz et al. |
| 2005/0240092 | A1* | 10/2005 | Shah et al. .................... 600/365 |
| 2007/0167853 | A1* | 7/2007 | Melker et al. ................. 600/532 |
| 2007/0173731 | A1* | 7/2007 | Meka et al. .................... 660/543 |

FOREIGN PATENT DOCUMENTS

| | | |
|---|---|---|
| DE | 29 902 593 | 8/1999 |
| EP | 0 370 151 A1 | 5/1990 |
| EP | 0 979 997 | 2/2000 |
| GB | 829 409 | 3/1960 |
| GB | 2 309 166 A | 7/1997 |
| GB | 2 329 245 A | 3/1999 |
| JP | 08313407 | 11/1996 |
| JP | 09196915 | 7/1997 |
| RU | 2104535 | 1/1996 |
| WO | WO 87/02773 | 5/1987 |
| WO | WO 92/10749 | 6/1992 |
| WO | WO 95/08113 A1 | 3/1995 |
| WO | WO 95/31718 | 11/1995 |
| WO | WO 98/57145 A1 | 12/1998 |
| WO | WO 99/12471 | 3/1999 |
| WO | WO 99/66304 | 12/1999 |
| WO | WO 00/25108 A1 | 5/2000 |
| WO | WO 00/67820 | 11/2000 |
| WO | WO 00/79243 A1 | 12/2000 |
| WO | WO 01/34024 | 5/2001 |
| WO | WO 01/93743 | 12/2001 |
| WO | WO 02/17991 A2 | 3/2002 |
| WO | WO 02/079514 A1 | 10/2002 |
| WO | WO 03/016901 A1 | 2/2003 |
| WO | WO 03/045473 | 6/2003 |
| WO | WO 2004/037316 A | 5/2004 |
| WO | WO 2004/065404 A1 | 8/2004 |
| WO | WO 2005/033707 A | 4/2005 |
| WO | WO 2006/057816 | 6/2006 |

OTHER PUBLICATIONS

U.S. Appl. No. 09/708,789, filed Nov. 8, 2000, Lampotang et al.
Baker, B. et al., "An Electronic Aptamer-Based Small Molecule Sensor for the Rapid, Label-Free Detection of Cocaine in Adulterated Samples and Biological Fluids," *J. Am. Chem. Soc.*, 2006, pp. 3138-3139, vol. 128, No. 10.
Brody et al., "Aptamers as therapeutic and diagnostic agents", *Reviews in Molecular Biotechnology*, 2000, vol. 74, pp. 5-13.
Brody et al., "The use of Aptamers in Large Arrays for Molecular Diagnostics", *Molecular Diagnosis*, 1999, vol. 4, No. 4, pp. 381-388.
Chandiok et al., "Screening for bacterial vaginosis: a novel application of artificial nose technology", *Journal of Clinical Pathology*, 1997, vol. 50, No. 9, pp. 790-791.
Dicesare et al., "Saccharide Detection Based on the Amplified Fluorescence Quenching of a Water-Soluble Poly(phenylene ethynylene) by a Boronic Acid Functionalized Benzyl Viologen Derivative," *Langmuir*, 2002, pp. 7785-7787, vol. 18, No. 21.
Dickinson, T. A. et al., "Current Trends in 'Artificial-Nose' Technology," *Tib Tech*, 1998, vol. 16, pp. 250-258.
Effros et al.; "Dilution of Respiratory Solutes in Exhaled Condensates," *Am. J. Respir. Crit. Care Med.*, 2002, pp. 663-669, vol. 165.
Fang et al., "Detection of Organic Chemicals by SAW Sensor Array", *Sensors and Actuators*, 1999, vol. B56, pp. 155-157.
Frauendorf et al., "Detection of Small Organic Analytes by Fluorescing Molecular Switches", *Bioorganic & Medicinal Chemistr*, 2001, pp. 2521-2524, vol. 9.
Fujita et al., "A Simple method for detecting plasma propofol", *Anesth. Analog*, 2000, vol. 90, pp. 1452-1454.
Ganga-Zandzou, P.S. et al. "A $^{13}$C-urea breath test in children with *Helicobacter pylori* infection: validity of the use of a mask to collect exhaled breath sample," *Acta. Paediatr.*, 2001, vol. 90, pp. 232-233.

Grate et al., "Determination of Partition Coefficients from Surface Acoustic Wave Vapor Senor Responses and Correlation with Gas—Liquid Chromatographic Partition Coefficients", *Anal. Chem.*, 1988, vol. 60, pp. 869-875.
Groves et al., "Analyzing organic vapors in exhaled breath using a surface acoustic wave sensor array with preconcentration: Selection and characterization of the preconcentrator adsorbent", *Analytica Chimica Acta*, 1998, pp. 131-143, vol. 371.
Hammon III, W. S. et al., "Forensic GPR: Finite-Difference Simulations of Responses From Buried Human Remains," *Journal of Applied Geophysics*, 2000, vol. 45, pp. 171-186.
Hong, C. et al., "Carbon Nanotube-Enhanced Electrochemical DNA Biosensor for DNA Hybridization Detedtion", *Anal. Bioanal. Chem.*, 2003, vol. 375, pp. 287-293.
Jayasena, "Aptamers: An Emerging Class of Molecules That Rival Antibodies in Diagnostics" *Clinical Chemistry*, 1999, vol. 45, No. 9, pp. 1628-1650.
Kraman, P., "Prescription Drug Diversion," *Trends Alert* provided by the Council of State Government at www.csg.org, Apr. 2004.
Kuipers et al., "First-pass lung uptake and pulmonary clearance of propofol," *Anesthesiology*, 1999, vol. 91, pp. 1780-1787.
Miller III, E. R. et al., "Association Between Cigarette Smoking and Lipid Peroxidation in a Controlled Feeding Study," *Circulation*, 1997, vol. 96, No. 4, pp. 1097-1101.
Pantarotto D. et al., "Synthesis, Structural Characterization, and Immunological Properties of Carbon Nanotubes Functionalized with Peptides", *J. Am. Chem. Soc.*, 2003, vol. 125, pp. 6160-6164.
Perri, F. "Diagnosis of *Helicobacter pylori* infection: which is best? The urea breath test," *Dig. Liver. Dis.*, 2000, vol. 32, Supp. 3, pp. S196-S198.
Phillips, "Breath Tests in Medicine" *Scientific American*, 1992, pp. 74-79.
Stojanovic et al., "Aptamer-Based Folding Fluorescent Sensor for Cocaine" *Journal of the American Chemistry Society*, 2001, vol. 123, pp. 4928-4931.
Stuart, B. H. et al., "Studies of Adipocere Using Diffuse Reflectance Infrared Spectroscopy," *Vibrational Spectroscopy*, 2000, vol. 24, pp. 233-242.
Stubbs, D. D. et al., "Investigation of Cocaine Plumes Using Surface Acoustic Wave Immunoassay Sensors," *Anal. Chem.*, 2003, vol. 75, pp. 6231-6235.
Tierney et al., "Design of a Biosensor for Continual, Transdermal Glucose Monitoring," *Clinical Chemistry*, 1999, pp. 1681-1683, vol. 45, No. 9.
United States Department of Justice, "Review of the Drug Enforcement Administration's (DEA) Control of the Diversion of Controlled Pharmaceuticals," Report No. I-2002-010 www.usdoj.gov/oig/inspection/DEA/0210/background.htm, Sep. 2002.
U.S. Food and Drug Administration, "FDA White Paper, Protecting the Public Health: FDA Pursues and Aggressive Enforcement Strategy," www.fda.gov/oc/whitepapers/enforce.html, Jun. 30, 2003.
U.S. Food and Drug Administration, "New FDA Initiative to Combat Counterfeit Drugs," www.fda.gov/oc/initiatives/counterfeit/backgrounder.html, Jul. 2, 2004.
Vass, A., "Beyond the Grave—Understanding Human Decomposition," *Microbiology Today*, Nov. 2001, vol. 28, pp. 190-192.
Vass, A. et al., "Detection of Buried Human Remains Using Bioreporter Fluorescence," U.S. Dept. of Energy Report, Y/NSP-726, 2001.
Xiao et al., "Label-Free Electronic Detection of Thrombin in Blood Serum by Using an Aptamer-Based Sensor," *Angew. Chem. Int. Ed.*, 2005, pp. 5456-5459, vol. 44.
Xiao et al., "A Reagentless Signal-On Architecture for Electronic, Aptamer-Based Sensors via Target-Induced Strand Displacement," *Journal of American Chemical Society*, 2005, pp. 17990-17991, vol. 127, No. 51.
Effros, R.M. et al., "Epithelial lining fluid solute concentrations in chronic obstructive lung disease patients and normal subjects," *Journal of Applied Physiology*, Oct. 2005, vol. 99, pp. 1286-1292.
Goldoni, M. et al., "Influence of condensation temperature on selected exhaled breath parameters," *BMC Pulmonary Medicine*, 2005, vol. 5, No. 10.

Manolis, A., "The Diagnostic Potential of Breath Analysis," *Clin. Chem.*, 1983, vol. 29, No. 1, pp. 5-15.

Mutlu, G. et al., "Collection and Analysis of Exhaled Breath Condensate in Humans," *Am. J. Respir. Crit. Care Med.*, 2001, vol. 164, pp. 731-737.

Arvanitakis, C. et al., "Lactase Deficiency—a Comparative Study of Diagnostic Methods," *The American Journal of Clinical Nutrition*, Oct. 1977, pp. 1597-1620, vol. 30.

Ballantine, D.S. et al., "Surface Acoustic Wave Devices for Chemical Analysis," *Anal. Chem.*, 1989, pp. 704A-712A, vol. 61, No. 11.

Barkley, J. et al., "Gas Chromatography Mass Spectrometry Computer Analysis of Volatile Halogenated Hydrocarbons in Man and His Environment- A Multimedia Environmental Study," *Biochemical Mass Spectrometry*, 1980, pp. 139-147, vol. 7, No. 4.

Caspary, W.F., "Breath Tests," *Clinics in Gastroenterology*, May 1978, pp. 351-374, vol. 7, No. 2.

Clark, N. et al., "Non-invasive Measurement of Glucose in Airway Surface Liquid," *Soceity for Younger Scientists and Engineers in the UK*, 2005.

Conkle, J.P. et al., "Trace Composition of Human Respiratory Gas," *Arch. Environ. Health*, Jun. 1975, pp. 290-295, vol. 30.

Fisher et al. "A man-portable chemical sniffer utilizing Novel Fluorescent polymers for detection of ultra-trace concentrations of explosives emanating from landmines," *Nomadics Inc.*, 2000, pp. 1-10.

Gage, J.C. et al., "A Method for the Determination of Low Concentrations of Organic Vapours in Air and Exhaled Breath," *Ann. Occup. Hyg.*, 1977, pp. 127-134, vol. 20.

Hanson et al., "The use of a novel electronic nose to diagnose the presence of intrapulmonary infection," *Anesthesiology*, Sep. 1997, vol. 87, No. 3A, Abstract A269.

Huang et. al., "Depth of anesthesia estimating & propofol delivery system", Aug. 1, 1996, http://www.rpi.edu/~royr/roy_descpyt.html.

Kang, B.S. et al., "Wide Bandgap Semiconductor Nanorod and Thin Film Gas Sensors," *Sensors*, 2006, vol. 6, pp. 643-666.

Krotoszynski, B.K. et al., "Characterization of Human Expired Air: A Promising Investigative and Diagnostic Technique," *J. Chromat. Sci.*, Jul. 1977, pp. 239-244, vol. 15.

Liebich et al. "Volatile Substances in Blood Serum: a Profile Analysis and Quantitative Determination," *Journal of Chromatography*, 1977, vol. 142, pp. 505-516.

Lukens, "Detection of drug usage via breath analysis within immunoassay film badge," *Proceedings of SPIE-The International Society for Optical Engineering*, 1997, pp. 79-83, vol. 2932.

Manolis et al, "The detection of Δ9-tetrahydrocannabinol in the breath of human subjects," *Clinical Biochemistry*, 1983, pp. 229-233, vol. 16, No. 4.

Maugh, T.H., "Separations by MS Speed Up, Simplify Analysis," *Science, New Series*, Aug. 8, 1980, pp. 675-677, vol. 209, No. 4457.

McLafferty, F., "Tandem Mass Spectrometry," *Science, New Series*, Oct. 16, 1981, pp. 280-287, vol. 214, No. 4518.

Mueller et al. "Experience in mass spectrometric identification in acute poisoning," *Beitr. Diagn. Ther, Akuter. Intox., Vortr. Symp. 4$^{th}$*, 1982, pp. 126-134, Abstract Only.

O'Neill, et al., "A Computerized Classification Technique for Screening for the Presence of Breath Biomarkers on Lung Cancer," *Clinical Chemistry*, 1988, pp. 1613-1618, vol. 34, No. 8.

Parry et al., "Leg ulcer odour detection identified beta-haemolytic streptococcal infection," *Journal of Wound Care*, 1995, vol. 4, pp. 404-406.

Pavlou et al., "Sniffing out the truth: Clinical Diagnosis Using the Electronic Nose," *Clin. Chem, Lab, Med.*, 2000, vol. 38, No. 2, pp. 99-112.

Prokopuk, N. et al., "Development of GaN-based Micro Chemical Sensor Nodes," *IEEE Sensors*, 2005.

Rogers et al. "Fiber-optic biosensors based on total internal-reflection fluorescence," *American Chemical Society*, 1992, Ch. 13, pp. 165-173.

Schwabe, A.D. et al., "Breath Tests for the Detection of Fat Malabsorption," *Gastroenterology*, 1979, pp. 216-218, vol. 76, No. 1.

Tracqui, A. et al, "Systematic Toxicological Analysis Using HPLC/DAD," *Journal of Forensic Sciences*, 1995, vol. 40, No. 2, pp. 254-262.

Vass, A. et al., "Decomposition Chemistry of Human Remains: A New Methodology for Determining the Postmortem Interval," *J. Forensic Sci.*, 2002, vol. 47, No. 3, pp. 542-553.

Wohltjen et al., "Vapor Detection with Surface Acoustic Wave Microsensors", *Chemical Sensors and Microinstrumentation*, 1989, pp. 157-175.

Yost, R.A. et al., "Triple Quadruple Mass Spectrometry for Direct Mixture and Analysis and Structure Elucidation," *Analytical Chemistry*, Oct. 1979, pp. 1251-1264, vol. 51, No. 12.

Effros et al. Dilution of Respiratory solutes in Exhaled Condensates, Am J. Respir. Crit. Care Med vol. 1565, pp. 663-669, 2002.

Philips et al. "Factors determining the appearance of glucose in upper and lower respiratory tract secretions," Intensive Care Med (2003) 29:2204-2210.

Williams, Biological and Analytic Components of Variation in Long-Term Studies of Serum Consitutents in Normal Subjects, I. Objectives, Subject Selection, Laboratory Procedures, and Estimation of Analytic Deviation , Clinical Chemistry vol. 16, No. 12 1970 pp. 1016-1021.

Harris et al., Biological and Analytic Components of Variation in Long-Term Studies of Serum Consitutents in Normal Subjects, II. Estimating Biological Components of Variation, Clinical Chemistry vol. 16, No. 12 1970 pp. 1022-1027.

Cotlove et al. Biological and Analytic Components of Variation in Long-Term Studies of Serum Consitutents in Normal Subjects, III. Physiological and Medical Implications, Clinical Chemistry vol. 16, No. 12 1970 pp. 1028-1032.

Young et al. Biological and Analytic Components of Variation in Long-Term Studies of Serum Consitutents in Normal Subjects, IV. Results of a Study Designed to Elminate Long-Term Analytic Deviations, Clinical Chemistry vol. 17, No. 5 1971 pp. 403-409.

Harris et al., Biological and Analytic Components of Variation in Long-Term Studies of Serum Consitutents in Normal Subjects, V. Estimated Bilogical Variations in Ionized Calcium, Clinical Chemistry vol. 17, No. 10 1971 pp. 983-987.

Kenny, "Target-Controlled Infusions-Pharmacokinetic and Pharmacodynamic Variations." www.anaesthesiologie.med.uni-erlangen.de/esctaic97/a_kenny.htm, 1997.

* cited by examiner

1. EBC APPLICATION

1. EBC APPLICATION

1. EBC APPLICATION

1. EBC APPLICATION

115 Peltier (heating/cooling device)

150 Known glucose standard

145 Glucose test section

130 Cl⁻ calibration standardization section

D-Glucose

Trimethylsilyl O-methyloxime derivative of D-glucose

CONDENSATE GLUCOSE ANALYZER

FIELD OF INVENTION

The present invention relates to non-invasive monitoring of glucose concentrations in blood; and more particularly, to a system and method utilizing a breath condensate detection system for the frequent monitoring of glucose concentrations in subjects who are at risk for hypoglycemia, hyperglycemia, and/or glucose level fluctuations that put the subject at medical risk.

BACKGROUND INFORMATION

Abnormal levels of glucose in the blood of humans can have a number of consequences. For example, fluctuations of blood glucose levels outside of the physiological range can result in one of two states, hypoglycemia and hyperglycemia. Hypoglycemia is defined as plasma glucose levels below normal (70 mg/dL). Hypoglycemia can be symptomatic or asymptomatic. For example, subjects suffering from postprandial hypoglycemia generally have symptoms of adrenergic stimulation including diaphoresis, anxiety, irritability, palpitations, tremor, and hunger. Such symptoms typically occur from about 2 to 4 hours postprandially and tend to occur suddenly with symptoms generally subsiding in about 15 to 20 minutes. Postprandial hypoglycemia is often idiopathic, however, it can be caused by early diabetes, alcohol intake, renal failure, and drug treatments.

In addition, a category of hypoglycemia exists which is designated as fasting hypoglycemia. Clinically, this form of hypoglycemia may have symptoms of neuroglycopenia including headache, fatigue, and mental dullness. In more severe cases, hypoglycemia can progress to confusion, blurring of vision, seizure, and ultimately loss of consciousness or seizure. Fasting hypoglycemia can occur with a fast of greater than 4 hours, and further can be caused by an insulinoma (insulin producing tumor) or resulting from self-administered insulin or intake of other hypoglycemic agents, alcohol abuse, liver disease (e.g., decreased gluconeogenesis), pituitary insufficiency, or adrenal insufficiency.

Hyperglycemia, on the other hand, refers to excessive levels of blood glucose in a subject. There are many forms of hyperglycemia, the primary form being diabetes, which is defined as hyperglycemia secondary to decreased insulin production or an increase in peripheral tissue resistance to the action of insulin. Insulin, in simple terms, is the hormone that unlocks the cells of the body, allowing glucose to enter those cells and feed them. In diabetic subjects, glucose cannot enter the cells and subsequently, glucose builds up in the blood and the body's cells literally starve to death. Although the cause of diabetes is not completely understood, genetics, environmental factors, and viral causes have been partially identified.

The American Diabetes Association reports that nearly 6% of the population in the United States, a group of 16 million people, has diabetes. The Association further reports that diabetes is the seventh leading cause of death in the United States, contributing to nearly 200,000 deaths per year. Diabetes is a chronic disease having no cure.

There are two major types of diabetes: Type I and Type II. Type I diabetes (formerly known as juvenile onset diabetes) is an autoimmune disease in which the body does not produce any insulin and most often occurs in young adults and children. People with Type I diabetes must take daily insulin injections to stay alive.

Type II diabetes is a metabolic disorder resulting from the body's inability to make enough, or properly to use, insulin. Type II diabetes accounts for 90-95% of diabetes. In the United States, Type II diabetes is nearing epidemic proportions, principally due to an increased number of older Americans and a greater prevalence of obesity and a sedentary lifestyle.

Diabetics having Type I diabetes typically are required to self-administer insulin using, e.g., a syringe or a pen with needle and cartridge. Continuous subcutaneous insulin infusion via implanted pumps is also available. Insulin itself was formally obtained from pork pancreas but is now made chemically identical to human insulin by recombinant DNA technology or by chemical modification of pork insulin. Although there are a variety of different insulins for rapid-, short-, intermediate-, and long-acting forms that may be used variously, separately or mixed in the same syringe, use of insulin for treatment of diabetes is not to be ignored.

The general characteristics of the symptoms of diabetes include the following: polyuria (high urine volume); hyperglycemia (high blood glucose levels); glucosuria (loss of glucose in urine); polydipsia (excessive thirst); polyphagia (excessive hunger); and sudden weight loss.

It has been observed that complications resulting from diabetes are the third leading cause of death in most developed countries. Diabetes is a risk factor for a variety of conditions including coronary heart disease, cerebrovascular stroke, neuropathy (nerve damage), nephropathy (kidney damage), retinopathy (eye damage), hyperlipidemia (excessive blood lipids), angiopathy (damage to blood vessels) and infection. For example, diabetes is said to be the leading cause of new cases of blindness in individuals in the range of ages between 20 and 74; from 12,000-24,00 people per year lose their sight because of diabetes. Diabetes is the leading cause of end-stage renal disease, accounting for nearly 40% of new cases. Nearly 60-70% of people with diabetes have mild to severe forms of diabetic nerve damage which, in severe forms, can lead to lower limb amputations. People with diabetes are 2-4 times more likely to have heart disease and to suffer strokes.

The healthcare costs associated with the treatment of diabetes and diabetic complications are enormous and projected to increase with the number of American living to older ages and the increased incidence of obesity. Much of the morbidity and mortality can be ameliorated by the use of insulin or oral medications (and in many cases weight loss), but the key to diabetes control is frequent measurement of blood glucose concentration. This is vital in determining the amount of insulin or oral medications that must be given.

Thus, it is highly recommended by the medical profession that subjects who are at risk or have been diagnosed with hypoglycemia, hyperglycemia (including diabetes), and/or glucose fluctuations practice self-monitoring of blood glucose (SMBG). For example, diabetic subjects may make insulin dosage adjustments before injection based upon the level of glucose in the blood. Adjustments are necessary since blood glucose levels vary day to day for a variety of reasons, e.g., exercise, stress, rates of food absorption, types of food, hormonal changes (pregnancy, puberty, etc.) and the like.

Present devices available for SMBG are complicated and difficult for many diabetics to use and often require them to obtain an adequate blood sample. Thus, despite the importance of SMBG, several studies have found that the proportion of individuals who self-monitor at least once a day significantly declines with age. This decrease is likely due simply to the fact that SMBG typically involves obtaining blood from a finger stick. Most diabetics, even those aware of the complications of hypo- and hyperglycemia, do not test frequently enough (for Type I [insulin dependent] diabetics this may be 6-8 times/D and for Type II diabetics controlled with oral agent testing should ideally be performed at least 2 times/D) because they consider obtaining blood to be significantly more painful than the self-administration of insulin and SMBG is far more time consuming and complicated. The FDA is fully aware of the many shortcomings of the devices used for SMBG, but newer technologies or matrices have not proven any more reliable.

There is a desire for a less invasive method of glucose measurement. Methods exist or are being developed for a minimally invasive glucose monitoring, which use body fluids other than blood (e.g., sweat, tears, or saliva) or subcutaneous fluid. Sweat and saliva are relatively easy to obtain, but their glucose concentration appears to lag in time significantly behind that of blood glucose. Unfortunately, tears, saliva and sweat have failed as viable matrices for use as surrogates for blood in monitoring glucose levels.

Billions of dollars have been spent on sensors that can be temporarily inserted into the subcutaneous tissues (usually of the abdomen) in order to measure glucose continuously. The fluid present between cells in this space is referred to as "interstitial fluid." Continuous measurement of interstitial fluid could lead to the development of closed loop glucose control with insulin pumps. The ultimate goal is a device that could be implanted and would continuously measure glucose and provide insulin to tightly regulate glucose concentration. This goal has remained elusive and present sensors function for only a few days and interstitial fluid has been shown to be an average of the glucose concentration over periods of time that exceed those acceptable to sense rapid changes in glucose concentration, especially when hypoglycemia occurs.

Breath is a unique bodily fluid. Unlike blood, urine, feces, saliva, sweat and other bodily fluids, it is available on a breath to breath, and therefore continuous, basis. It is readily available for sampling non-invasively and because the lung receives all of the blood flow from the right side of the heart, measurements of analytes/compounds in breath correlate strongly and reproducibly with blood concentration. It is less likely to be associated with the transfer of serious infections than other bodily fluids and collection of samples is straightforward and painless. More importantly, certain compounds that are produced by the cellular lining of the airways, notably nitric oxide (NO), may be in higher concentration in the airways and therefore easily assessed in breath as opposed to blood, urine, and the like.

Exhaled breath, especially when exhaled through the mouth (in contrast to breath exhaled from the nose, which acts as a heat-moisture exchanger) is a complex fluid that contains 100% humidity at 37° C. (body temperature) and aerosol droplets that are derived from airway lining fluid, predominantly from fluid lining the alveoli but may also include contributions from non-alveolar areas. If the temperature of the collected sample is maintained at 37° C. or higher it will remain in this state and can be treated as a gas for compounds that are insoluble in water or readily diffuse out of water.

Truly simple, non-invasive methods of measuring glucose are not commercially available. Insofar as is known, glucose has not been previously reported as being detectable in exhaled breath condensates (EBC), let alone having any correlation with blood and condensate concentration. Thus, there is a need for a commercially available, non-invasive EBC sensing device that enables frequent monitoring of glucose levels in subjects.

SUMMARY OF THE INVENTION

The present invention solves the needs in the art by providing methods and systems for non-invasive monitoring of glucose concentration in blood, as well as systems and methods for non-invasive monitoring of the effects of one or more therapeutic regimens on the concentration of glucose in a subject. The systems and methods of the present invention utilize sensors that can analyze a subject's EBC to detect, quantify, and/or trend concentrations of glucose present in the EBC, which correlate to the glucose concentration in the subject's body, in particular in blood.

In one embodiment, the present invention provides systems and methods for monitoring glucose levels and/or concentration in a subject diagnosed with hypoglycemia, hyperglycemia (including diabetes), and/or fluctuations in glucose levels.

In a related embodiment, the present invention provides systems and methods for monitoring glucose levels and/or concentration in a subject having a disease state or condition that puts the subject at risk for hypoglycemia, hyperglycemia, or fluctuations toward hypoglycemia and/or hyperglycemia (for example, quickly dropping or increasing glucose levels). A wide variety of disease states or conditions benefit from frequent glucose monitoring; for example, such monitoring provides a tool for the subject and/or healthcare professional to develop a response or plan to assist with management of the disease state or condition.

In other embodiments of the invention, systems and methods are provided for monitoring the efficacy of therapeutic regimens administered to a subject to treat hypoglycemia, hyperglycemia, and/or abnormal fluctuations in glucose levels.

As understood by the skilled artisan, exhaled breath samples maintained at 37° C. or higher can be manipulated to collect the aerosol droplets without the free water that accounts for the 100% humidity. In one embodiment of the invention, to collect just the aerosol droplets, a series of screens (referred to in the art as impactors) can be used to collect droplets of a particular size. These systems are frequently used to determine the size of drug particles delivered by devices such as meter dose inhalers. In this instance, compounds that readily dissolve in water (such as glucose) can be collected from exhaled breath samples without being diluted by the free water (100% humidity) that is present. Alternatively, in certain circumstances, compounds that are highly water soluble and likely to remain in solution, such as glucose, can be collected as exhaled breath condensate (EBC) when the sample is cooled (this condensate would include both aerosol droplets and free water condensed from the 100% humidity). This liquid can then be analyzed with sensors that are designed for liquid-based analyses.

In general, aerosol droplet will contain a higher concentration of an analyte such as glucose, but the quantity of liquid will be less than that collected from EBC, which will have a lower concentration of the analyte. The decision on whether to collect just the aerosol droplets or EBC will depend on the size of sample needed for measurement of the concentration of the analyte and the simplicity of the various sensors. In general, it is easier to collect EBC than aerosol droplets. Unless otherwise indicated, EBC will be used to describe the total amount of condensate, that is the aerosol droplets and the free evaporative water.

Thus, exhaled breath measurements can be used to monitor glucose levels and to correlate them with blood concentrations. By using breath to determine blood glucose concentrations, diabetics are freed from having to perform frequent blood sticks to determine their glucose concentrations or freed from the risk of developing tissue damage and infection from implantable monitoring devices. Further, continuous monitoring of breath glucose can be used in the operating room during surgery and/or the intensive care units since tight glucose control has been shown to improve wound healing and reduce the incidence of post-operative infection.

According to the present invention, it has been determined that glucose is present in exhaled breath, but almost exclusively in EBC. In one embodiment of the invention, a non-invasive system for monitoring the concentration of glucose in a subject having a disease state or condition is provided, said system comprising: a means for collecting a sample of exhaled breath from a subject; a means for extracting the condensates from the sample of exhaled breath; and a sensor having sufficient sensitivity and selectivity to detect and/or quantify the glucose present in the condensates.

A method of use according to the invention comprises: collecting a sample of exhaled breath from a subject; extracting condensates from the sample of exhaled breath; and contacting the condensates with a sensor having the ability to detect and/or quantify the glucose. Such systems and methods are helpful in assisting in the management of diabetic disease states (e.g., gestational diabetes; fetal or premature-birth neonate (i.e., a neonate born before term) glucose management, Type I and II diabetes).

In accordance with the subject invention, a sensor for detecting glucose in EBC can be selected from a variety of systems that have been developed for use in collecting and monitoring liquid components. For example, the sensor of the subject invention can be selected from those described in U.S. Pat. Nos. 4,431,507; 5,288,636; 5,517,313; 5,762,770; 5,894,351; 5,910,661; 5,917,605; 5,997,817; 6,294,062; 6,558,528; 6,572,566; 6,780,651; 6,893,552; 6,913,668; and, 7,074,307, all of which are incorporated herein by reference in their entirety.

Further, sensor systems having computerized data analysis components can also be used in the subject invention (i.e., U.S. Pat. No. 4,796,639). Sensors of the subject invention can also include commercial devices commonly known as "artificial" or "electronic" noses or tongues. Other sensors for use in accordance with the subject invention include, but are not limited to, metal-insulator-metal ensemble (MIME) sensors, cross-reactive optical microsensor arrays, fluorescent polymer films, surface enhanced raman spectroscopy (SERS), diode lasers, selected ion flow tubes, metal oxide sensors (MOS), bulk acoustic wave (BAW) sensors, calorimetric tubes, infrared spectroscopy, semiconductive gas sensor technology; mass spectrometers, fluorescent spectrophotometers, conductive polymer gas sensor technology; aptamer sensor technology; amplifying fluorescent polymer (AFP) sensor technology; microcantilever technology; molecularly polymeric film technology; surface resonance arrays; microgravimetric sensors; thickness sheer mode sensors; surface acoustic wave gas sensor technology; radio frequency phase shift reagent-free and other similar micromechanical sensors. Preferred sensors of the invention are those that utilize immobilized glucose-binding molecules such as antibodies or parts of antibodies, enzymes, oligonucleotides (e.g., DNA or RNA aptamers), peptides, or proteins or parts of proteins (see, for example, U.S. Pat. No. 6,475,750, which is incorporated herein). More preferably, the sensors of the invention are those that utilize hydrogel immobilized glucose-binding enzymes (see, for example, U.S. Pat. Nos. 5,423,739; 5,540,828; 5,954,685; 5,989,409; 6,144,869; 6,356,776; 6,594,514; 6,850,790; 6,902,905; and 6,999,810, all of which are incorporated herein by reference in their entirety).

In a preferred embodiment of the subject invention, a specific phase of the respiratory cycle, namely the end-tidal portion of exhaled breath, is sampled to collect condensates from which glucose amounts or concentrations are determined, wherein the glucose amounts or concentrations in EBC correlate to blood glucose concentrations.

The systems and methods of the invention are particularly helpful to the subject and/or healthcare professional in monitoring subject response to therapeutic regimens prescribed to assist in the management of the subject's disease state and/or associated conditions. Such therapeutic regimens include, but are not limited to, response to hypoglycemic agents including insulin and oral agents, weight management regimens, including ketogenic diets, diets for performance athletes, and evaluation of the effects of drugs on glucose and/or insulin homeostasis.

One aspect of the present invention comprises a system and method for monitoring an effect of at least one non-insulin-containing and/or one insulin-containing pharmaceutical composition on glucose levels in a subject receiving the pharmaceutical composition. In the method, glucose monitoring in the subject may be carried out by: administering a prescribed pharmaceutical composition that affects glucose levels in a subject; obtaining a sample of the subject's exhaled breath; extracting condensates from the sample of exhaled breath; and assessing glucose amounts or concentrations in the condensates extracted from the subject's exhaled breath. In a related embodiment, a record is maintained of the treatments with the pharmaceutical composition as well as of corresponding glucose amounts or concentrations determined present in EBC after (and in certain instances before) each treatment. The records are compared to evaluate the effect of the pharmaceutical composition on glucose levels in the subject receiving the pharmaceutical composition (especially in diabetics, where other drugs interfere with glucose homeostasis).

According to the subject invention, the effect of any pharmaceutical composition known to be useful in modulating glucose levels can be monitored including, but not limited to, oral hypoglycemic agents, insulin, hormones, atypical antipsychotics, adrenergic medications such as pseudoephedrine, and the like. Oral hypoglycemic agents that can be monitored in accordance with the present invention include, but are not limited to, first-generation sulfonylurea compounds (e.g., acetohexamide, chlorpropamide, tolazamide, and tolbutamide); second-generation sulfonylureas (e.g., glipizide, glyburide, and glimepiride); biguanides; alpha-glucosidase inhibitors; and troglitazone.

In a further aspect, the present invention comprises a system and method for evaluating compliance with a weight management program in a subject, wherein monitoring of glucose amount or concentration in the subject is accomplished by monitoring glucose in EBC. In this method a reference range of glucose amounts or concentrations is determined that correspond to achieving a weight management goal in the subject. Such range of glucose amounts or concentrations typically comprises a high threshold glucose value and a low threshold glucose value. Rates of change (or trends) of glucose amounts or concentrations in the subject may be determined.

Another aspect of the present invention relates to a method for improving prognosis and/or reduction of adverse side-effects associated with a disease state or condition in a subject with abnormal glucose levels. In this aspect of the present invention, a reference range of glucose amounts or concentrations is determined that corresponds to achieving an improved prognosis or reduction of adverse side-effects associated with the disease state or condition in the subject. The reference range comprises, for example, a high threshold glucose value, a low threshold glucose value, a predetermined rate of change (e.g., glucose levels change at a rate faster than a predetermined rate of change), and/or a predicted glucose value for a later time point. The glucose condensate monitoring device of the invention may provide an alert corresponding to threshold values, rate changes, a predicted glucose value that falls outside of the predetermined range, etc. The series of glucose amounts or concentrations and the reference range are compared to evaluate compliance with the reference range of glucose amounts or concentrations to achieve an improved prognosis or reduction of adverse side-effects associated with the disease state or condition in the subject.

In one embodiment, a glucose condensate test kit is provided for monitoring glucose amounts or concentrations in a subject or for assessing the efficacy of a therapeutic regimen administered to a subject to address abnormal glucose levels. A kit of the invention contains the necessary material for performing the methods described herein. This kit may contain any one or combination of the following, but is not limited to, a breath collection device, which includes a means for extracting condensates from the sample of exhaled breath and a sensor for determining glucose amounts or concentrations in the condensates; a set of subject instructions for its use; and a device for keeping track of, storing, displaying, and/or communicating monitored results. In certain related embodiments, the device can calculate and display the blood glucose concentration based on the EBC glucose concentration.

In a related embodiment, the subject glucose EBC test kit is provided in combination with other known methods for the diagnosis of hypoglycemia, hyperglycemia, diabetes, or insulin resistance. For example, in certain embodiments, the glucose EBC concentration test kit includes a means for detecting insulin resistance when blood glucose levels are still in the normal range and before β-cell destruction leading to diabetes has occurred. To do so, the kits of the invention enable continuous monitoring of EBC insulin levels, where any change in levels of insulin in relation to blood/breath glucose or an delayed insulin response to a glucose load (such as a carbohydrate rich meal) would diagnose insulin resistance. Early diagnosis of diabetes could be achieved with the kits of the invention by the continuous monitoring of EBC insulin levels (e.g., through a ruthenium-oxide ($RuO_x$)-type catalytic film sensor), where a measurement of inadequate insulin concentrations in response to a carbohydrate load would provide early diagnosis of diabetes.

In a related embodiment, the occasional or continuous measurement of glucose/insulin ratio is highly advantageous for use in early detection of insulin resistance, which will allow timely intervention to prevent the development of Type II diabetes and/or its complications. In addition, the present invention can be used to monitor the progress of any intervention therapies, including diet and exercise. In certain embodiments, the occasional or continuous measurement of glucagon/insulin ratio (where glucagon is a hormone that increases glucose concentration) may be used instead of the glucose/insulin ratio.

Advantages of the test kits of the invention include the following: they are practical, sensitive and specific; the validity of the test kits is not influenced by stress, exercise, hormone imbalances, or some drugs and medications; the test kits provide a non-invasive method for monitoring glucose levels; the test kits are simple to perform and can be readily used in physicians' offices, medical laboratories, or at any location by the subject; and the test kits are safe for use by children and women.

In certain embodiments, the systems of the subject invention include a reporting system capable of tracking glucose concentrations that are present in EBC and/or tracking subject glucose levels (e.g., blood glucose levels) determined from EBC analysis. In related embodiments, the reporting system is capable of tracking glucose levels or concentrations remotely or proximately as well as being capable of providing the necessary outputs, controls, and alerts to the user, be it a healthcare provider, the subject, and the like.

In one embodiment, glucose concentration in breath condensates can be monitored intermittently or continuously in a wide range of environments. Small handheld portable equipment could be used by subjects in the home, at work, in nursing homes or while they are ambulatory, while other devices could be designed for continuous monitoring in the operating room, intensive care units and in other areas of hospitals or other healthcare facilities such as clinics, doctors offices where this capability would be valuable.

In one example, the glucose condensate sensing device of the invention could be used in a clinical setting or subject-based location before, during, or after delivery of a therapeutic regimen (such as administration of an insulin-containing pharmaceutical composition) to monitor the efficacy of the therapeutic regimen in addressing abnormal glucose levels in the subject.

The preferred device of the present invention includes the following parts: 1) an exhaled breath sampling device, wherein the device samples end-tidal exhaled breath; 2) a condensate extracting system for extracting the condensates from the sample of end-tidal exhaled breath; 3) a sensor having the ability to detect and/or quantify glucose present in the condensates; and 4) a signaling means, coupled to the sensor, for producing an electrical signal indicative of the presence and/or amount of glucose in the breath condensate detected by the sensor. The signaling means may be further operative to determine the approximate concentration of glucose present in the condensates and/or subject (such as blood glucose levels). In certain embodiments, the signaling means is coupled to a processor, 112, which can store, track, trend, and interpret the signals to provide useful information regarding glucose amount or concentration for display to the user.

In certain embodiments, the quantity of glucose detected can be evaluated by the processor and by a closed loop feedback system meter an appropriate dose of insulin. This would be desirable when a patient is taking inhaled insulin or insulin by continuous infusion (subcutaneous or intravenous). Alternatively, the processor can display on a screen the quantity of insulin the patient should self administer.

The exhaled breath sampling device that samples end-tidal exhaled breath preferably includes: a device and/or method for obtaining a sample of exhaled breath from a subject (such as a conventional breath sampling apparatus that includes a flow channel through which exhalation air flows); and a means for determining end-tidal breath (such as end-tidal component monitors; for example, $CO_2$ sensors; $O_2$ sensors; and flow, pressure, humidity and temperature sensors).

The sensor can be any known sensor having the sensitivity to detect and/or quantify glucose in condensate samples. Preferably, the sensor includes a surface that is exposed to the subject's condensates and also comprises a material selectively absorptive of glucose and/or EBC.

The condensate extracting system for extracting condensates present in end-tidal exhaled breath samples includes any one of many known devices for collecting condensates that are currently available to the skilled artisan. For example, one such device relies on gravity to form a condensate pool from which a sample for testing may be drawn. These types of devices require that condensate droplets become large enough to overcome water's naturally tendency to stick to the walls of a collecting tube. Eventually, the amount of condensate in the collection area becomes large enough for analysis. In some cases, the collecting tube is inserted into an ice bucket or may even be separately cooled by refrigeration systems in order to increase the amount and speed of condensate formation. In a preferred embodiment, a Peltier device is placed in contact with one wall of the condensate collecting device and cooled so that EBC preferably condenses in the cooled area of the collecting device. In some cases, a coating such as Teflon™ is applied to collecting tubes to make the tube walls non-wetting and non-reactive with glucose and to enhance the speed and amount of condensate collected.

The invention will now be described, by way of example and not by way of limitation, with reference to the accompanying sheets of drawings and other objects; features and advantages of the invention will be apparent from the following detailed disclosure and from the appended claims.

DETAILED DESCRIPTION OF THE INVENTION

Figure 1:
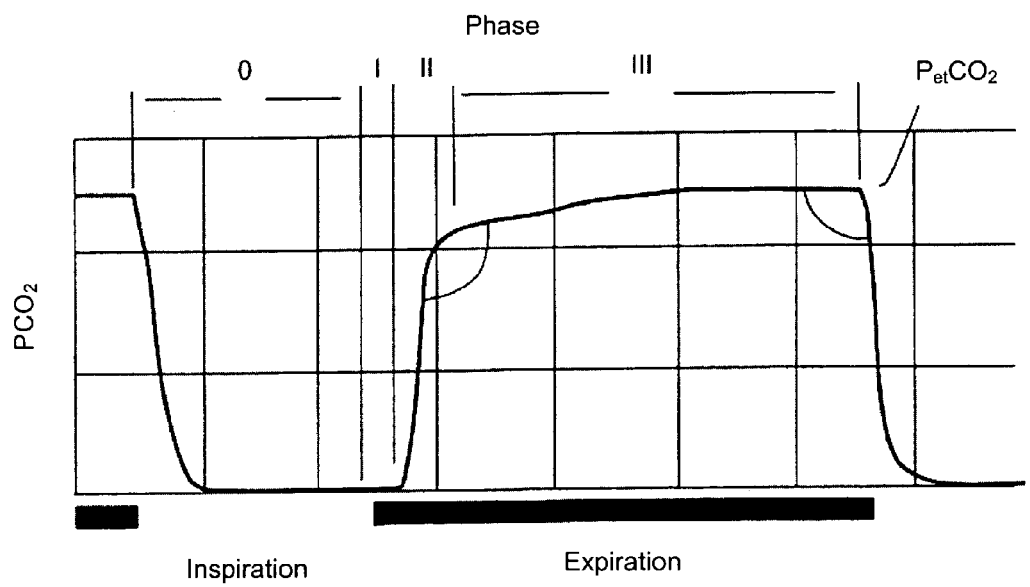
FIG. 1 shows a capnogram of a single respiratory cycle, which includes indication of an end-tidal portion of a breath sample.

The present invention provides systems and methods for non-invasive monitoring of a subject's glucose levels (or glucose concentration in blood) by analyzing the subject's EBC (or condensed aerosol droplets). The systems and methods of the present invention utilize sensors that can analyze a subject's EBC to detect, quantify, and/or trend concentrations of glucose present in the EBC. According to the subject invention, the concentration of glucose in EBC is proportionate to the concentration of glucose in blood. Thus, based on the condensate concentration of glucose, the corresponding blood glucose concentration in a patient can be non-invasively, accurately, and rapidly assessed. The disclosed ability to non-invasively monitor a subject's glucose levels using the systems and methods disclosed herein is particularly advantageous in diagnosing and monitoring the status of the subject's disease state or condition as well as in monitoring the efficacy of therapeutic regimens administered to the subject to treat abnormal glucose levels, especially where the results of the measurements can be used in a closed loop system to administer appropriate doses of insulin.

The practice of the present invention will employ, unless otherwise indicated, conventional methods and techniques of chemistry, biochemistry, electrochemistry and pharmacology, within the skill of the art. Such conventional methods and techniques are explained fully in the literature.

It is to be understood that the terminology used herein is for the purpose of describing particular embodiments only, and is not intended to be limiting. As used in this specification and the appended claims, the singular forms "a", "an" and "the" include plural referents unless the context clearly dictates otherwise. Thus, for example, reference to "a sensor" includes a single sensor or multiple sensors, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The term "processor" refers to a computer processor contained on an integrated circuit chip, such a processor may be small in size (such as a microprocessor) and can also include memory and associated circuits. A processor of the invention may further comprise programmed instructions to execute or control selected functions, computational methods, switching, etc. Processors and associated devices are commercially available from a number of sources, including, but not limited to, Cypress Semiconductor Corporation, San Jose, Calif.; IBM Corporation, White Plains, N.Y.; Applied Microsystems Corporation, Redmond, Wash.; Intel Corporation, Chandler, Ariz.; and, National Semiconductor, Santa Clara, Calif.

An "exhaled breath sampling device" or "exhaled breath sampling system" refers to any device and/or associated method for obtaining a sample of exhaled breath from a subject for the purpose of determining the concentration of glucose present in the sample, in particular the concentration of glucose present in the EBC. In certain embodiments, the exhaled breath sampling device is in operative contact with a "reservoir" or "collection reservoir," wherein a sample of exhaled breath is taken from the subject and placed into the reservoir to extract the condensates (and thereby detect and/or quantify the amount of glucose) in the reservoir.

In a preferred embodiment, the exhaled breath sampling device comprises a hydrogel. The hydrogel is linked to or contains an enzyme which reacts with high specificity with glucose (e.g., glucose oxidase, glucose dehydrogenase, glucose hexokinase) and a transduction mechanism that measures an electrical or other change that is related to the glucose binding event and/or concentration of glucose in the EBC. Other compounds or molecules that react with a high degree to specificity for glucose can also be used (e.g., molecular recognition entities such as aptamers, antibodies, and the like). In certain embodiments, an enzyme or molecular recognition entity is physically trapped within the hydrogel because the high molecular weight of the enzyme/entity prevents diffusion through the hydrogel. Alternatively the enzyme/entity can be chemically bonded to the hydrogel through well known immobilization chemistry of functional groups such as the hydroxyl group on pHEMA.

The hydrogel is preferably provided in a freeze-dried or dehydrated state and may be macroporous. As such, when the hydrogel is exposed to EBC containing glucose, it swells and incorporates the EBC containing the glucose into the spaces between the hydrogel polymer. The amount of EBC incorporated into these spaces can be as high as 99% of the total weight of the hydrogel, but lower water contents are usually used to maintain the strength (durometer) of the hydrogel The glucose-specific enzyme or molecular recognition entity present in the hydrogel then reacts with the glucose contained in the EBC and produces a compound which causes or changes an electrical current which is sensed by the transduction mechanism. Such change in electrical current indicates the presence and concentration of glucose in EBC. In certain embodiments, the amount of change in electrical current is proportional to the concentration of glucose in exhaled breath. According to the subject invention, the ratio of EBC glucose to blood glucose can be periodically determined for a specific individual in order to calibrate and ensure the accuracy of the device.

The term "analyte" is used herein to denote any physiological analyte that can be detected and/or measured in a biological, chemical, physical, enzymatic, or optical analysis.

A "condensate extracting system" or "means for extracting condensates" refers to any device and/or associated method for extracting condensates from exhaled breath, generally involving a cooling process and/or gravitational forces and/or specific flow characteristics (such as narrowing a portion of the device to produce high turbulent flow rates and thus cooling of the sample) to condense the condensates for aqueous phase glucose analyses. For example, condensate can be collected from a subject's sample of exhaled breath using a device that relies on gravity to form a condensate pool or a device that exposes the sample of exhaled breath to cool temperatures.

In a preferred embodiment, the exhaled breath sampling device includes a freeze-dried hydrogel, which contains a glucose-selective binding moiety such as an antibody, aptamer, enzyme, etc. The freeze-dried hydrogel swells to a specific volume upon absorption of the glucose containing EBC. In certain embodiments of the invention, the condensate extracting system is an integral part of the exhaled breath sampling device. In other embodiments, the condensate extracting system is separate from the exhaled breath sampling system.

The term "condensates" or "exhaled breath condensate" (or EBC), refers to breath liquid phase, breath aqueous phase, respiratory droplet/aerosols, breath evaporate, water vapor, bronchial or alveolar aerosols, alveolar lining fluid, airway lining fluid, and the like found in exhaled breath.

A "glucose monitoring system" or "glucose monitoring device" refers to a system useful for obtaining frequent measurements of glucose present in EBC. Such a device is useful, for example, for monitoring the amount or concentration of blood glucose in a subject. Such a system may comprise, but is not limited to, an exhaled breath sampling system, a condensate extracting system, a sensor, and a transduction method or signaling means in operative communication with the sensor. Such a device typically provides frequent measurement or determination of glucose amount or concentration in the subject and provides an alert or alerts when levels of the glucose being monitored fall outside of a predetermined range. Such devices may comprise durable and consumable (or disposable) elements.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex and, thus, includes adult and newborn subjects, whether male or female.

The term "sensor," "sensing device," or "sensor system," encompasses any technology that can be used to detect and/or measure the concentration or amount of a target analyte present in EBC (such as glucose, insulin, glucagon, and the like). Sensing devices for detecting glucose in EBC can include electrochemical devices, optical and chemical devices and combinations thereof. A more detailed description of sensors that can be used in accordance with the present invention is provided below.

A "signaling means" includes, but is not limited to, a "sensor electrode" or "sensing electrode" or "working electrode," which refers to an electrode that is monitored to determine the amount of electrical signal at a point in time or over a given time period, where the signal is then correlated with the concentration of glucose. The sensing electrode comprises a reactive surface which converts the detection of glucose by the sensor to an electrical signal. The reactive surface can be comprised of any electrically conductive material such as, but not limited to, platinum-group metals (including, platinum, palladium, rhodium, ruthenium, osmium, and iridium), nickel, copper, and silver, as well as, oxides, and dioxides, thereof, and combinations or alloys of the foregoing, which may include carbon as well. Some catalytic materials, membranes, and fabrication technologies suitable for the construction of amperometric sensors are described by Newman, J. D., et al. (1995) Analytical Chemistry 67:4594-4599.

The "signaling means" can include components in addition to the sensing electrode, for example, it can include a "reference electrode" and a "counter electrode." The term "reference electrode" is used to mean an electrode that provides a reference potential, e.g., a potential can be established between a reference electrode and a working electrode. The term "counter electrode" is used to mean an electrode in an electrochemical circuit that acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are preferred.

The term "reactive surface" refers to the surface of the sensing electrode that: (1) is in contact with the surface of an ionically conductive material through which glucose flows from a source thereof; (2) is comprised of a catalytic material (e.g., a platinum group metal, platinum, palladium, rhodium, ruthenium, or nickel and/or oxides, dioxides and combinations or alloys thereof) or a material that provides sites for electrochemical reaction; (3) converts a chemical signal (for example, hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal that is correlatable with the amount of glucose present in the electrolyte.

An "ionically conductive material" refers to any material that provides ionic conductivity, and through which electrochemically active species can diffuse. The ionically conductive material can be, for example, a solid, liquid, or semi-solid (e.g., in the form of a gel) material that contains an electrolyte, which can be composed primarily of water and ions (e.g., sodium chloride), and generally comprises 50% or more water by weight. The material can be in the form of a hydrogel, a sponge or pad (e.g., soaked with an electrolytic solution), or any other material that can contain an electrolyte and allow passage of electrochemically active species, especially glucose. Some exemplary hydrogel formulations are described in WO 97/02811, published Jan. 30, 1997. The ionically conductive material may comprise a biocide. Biocides of interest include, but are not limited to, compounds such as chlorinated hydrocarbons; organometallics; hydrogen releasing compounds; metallic salts; organic sulfur compounds; phenolic compounds (including, but not limited to, a variety of Nipa Hardwicke Inc. liquid preservatives registered under the trade names Nipastat®, Nipaguard®, Phenosept®, Phenonip®, Phenoxetol®, and Nipacide®); quaternary ammonium compounds; surfactants and other membrane-disrupting agents (including, but not limited to, undecylenic acid and its salts), combinations thereof, and the like.

The term "electrolyte" refers to a component of the ionically conductive medium which allows an ionic current to flow within the medium. This component of the ionically conductive medium can be one or more salts or buffer components, but is not limited to these materials.

The term "collection reservoir" is used to describe any suitable containment method or device for containing a sample of exhaled breath and/or condensates taken from a subject. For example, the collection reservoir can be a receptacle containing a material which is ionically conductive (e.g. liquid with ions therein), or alternatively it can be a material, such as a sponge-like material or hydrophilic polymer, used to keep the liquid in place. Such collection reservoirs can be in the form of a hydrogel (for example, in the shape of a disk or pad). Hydrogels are typically referred to as "collection inserts." Other suitable collection reservoirs include, but are not limited to, tubes, vials, strips, capillary collection devices, cannulas, and miniaturized etched, ablated or molded flow paths.

The terms "disease state," "condition" and "medical condition" refer to any physiological or environmental state about which a subject has concern. Exemplary disease states and conditions are described extensively herein, for example hypogylcemia, hyperglycemia, diabetes mellitus Types I and II, starvation, various genetic diseases that affect glucose homeostasis such as glycogen storage diseases, cardiovascular disease, cystic fibrosis, gestational diabetes, etc.

The term "aptamer," as used herein, refers to a non-naturally occurring oligonucleotide chain that has a specific affinity for glucose. Aptamers include nucleic acids that are identified from a candidate mixture of nucleic acids. In a preferred embodiment, aptamers include nucleic acid sequences that are substantially homologous to the nucleic acid ligands isolated by the SELEX method. Substantially homologous is meant a degree of primary sequence homology in excess of 70%, most preferably in excess of 80%.

The "SELEX™" methodology, as used herein, involves the combination of selected nucleic acid ligands, which interact with a target analyte in a desired action, for example binding to glucose, with amplification of those selected nucleic acids. Optional iterative cycling of the selection/amplification steps allows selection of one or a small number of nucleic acids, which interact most strongly with the target analyte from a pool, which contains a very large number of nucleic acids. Cycling of the selection/amplification procedure is continued until a selected goal is achieved. The SELEX methodology is described in the following U.S. patents and patent applications: U.S. patent application Ser. No. 07/536,428 and U.S. Pat. Nos. 5,475,096 and 5,270,163.

Breath Sampling and Condensate Extraction

The purpose of this invention is to condense exhaled sample(s) for aqueous phase glucose analyses. This will assist in monitoring a subject's glucose levels; diagnosing and monitoring the status of a subject's disease state or condition; as well as monitoring the efficacy of therapeutic regimens administered to the subject to treat abnormal glucose levels, all of which are based on the detected amount of glucose in EBC that is correlated with blood glucose concentration.

The investigations that have resulted in the present invention indicate that measured glucose in liquid phase exhaled breath correlates to blood glucose concentration. Exhaled breath maintained at body temperature (about 37° C.) is saturated with water. When a sample of exhaled breath is cooled below body temperature, the water condenses. If an adequate sample of condensate is extracted from breath, the condensate can be analyzed for a wide variety of analytes.

According to the subject invention, the physicochemical characteristics of a molecule will determine whether it is best captured and detected in the gaseous or liquid phase of breath. For example, compounds such as propofol, DMSO, and $CO_2$ are readily detected in the gas phase of breath, whereas molecular entities such as glucose, insulin, glucagon, and electrolytes are best sampled and detected in the breath via analysis of the liquid phase (aerosol droplets, EBC). Glucose is a polar molecule with numerous hydrogen bounds, which make it extremely hydrophilic; thus, glucose is essentially only present in the water droplets/aerosol from the airway lining fluid, predominantly deep within the lung from alveoli.

According to the subject invention, glucose is present in the alveolus in a concentration very close to, if not equal to, that in the blood as only two cells, the capillary endothelial cell and the alveolar lining cell, separate the blood from the alveolar gas. Unfortunately, the tiny aerosol droplets containing the glucose are diluted by alveolar lining fluid and water produced by evaporation. By the time the glucose containing droplets are exhaled and condensed, the concentration has been substantially diluted. This dilution is consistent with that predicted in the literature for compounds other than glucose. Up until this invention, the true alveolar droplet glucose concentration was unknown and the presence of glucose in the lung, especially in exhaled breath and EBC, was unconfirmed. Moreover, it was unknown whether there existed a reproducible and accurate ratio or correlation between glucose in EBC and blood glucose concentrations.

The present inventors have surprisingly discovered that the ratio of glucose in EBC to blood glucose concentration is 3 to 5 magnitudes lower and that this ratio is predictable and reproducible. In accordance with the present invention, a more predictive method is provided to monitor glucose concentration in a subject by monitoring breath (specifically EBC) rather than blood.

According to the present invention, the preferred exhaled breath sample taken from a subject is gas that originates deep in the lung (alveolar gas), which is not further diluted by gas from the trachea and conducting airways (deadspace). Deadspace gas would not contain glucose. If the collected sample contains a varying amount of deadspace gas, the glucose concentration detected may vary independently of the blood glucose levels in the subject, which would require additional calculations to accurately assess the correlative blood glucose concentration. For example, according to the subject invention, the deadspace, the ratio of dead space to tidal volume ($V_D/V_T$), or alveolar ventilation (which is tidal volume less deadspace or $V_T$-$V_D$) can be calculated for use in determining how much of the breath is due to deadspace ventilation and how much is alveolar ventilation. With such information, the skilled artisan could calculate the exhaled breath glucose concentration.

Generally, the exhalation gas stream comprises sequences or stages. At the beginning of exhalation there is an initial stage, the gas representative thereof coming from an anatomically inactive (deadspace) part of the respiratory system, in other words, from the mouth and upper respiratory tracts (the conducting airways). In the next stage, the gas is a mixture of deadspace and metabolically active gases. During the final "plateau" phase, which comprises the last portion of the exhaled breath, nothing but deep lung gas, so-called alveolar gas is present. This gas, which comes from the alveoli, is termed end-tidal gas.

According to the present invention, exhaled breath from any specific phase of the respiratory cycle can be sampled to detect for the presence of glucose in the condensates from the subject, but condensate from the end-tidal phase is most likely to correlate best with the blood glucose concentration. For example, sensors as described herein can be applied to extracted condensates from exhalation samples drawn from the initial phase, or the end-tidal (late plateau) phase.

Technology used for end-tidal component monitoring (such as $CO_2$ sensors, $O_2$ sensors, and NO sensors) can be used to determine when or at what stage the sample is collected. Known methods for airway pressure measurements, humidity or temperature measurement or for monitoring gas flow afford other means of collecting samples at the appropriate phase of the respiratory cycle. For example, airway gas flow, airway pressure or gas temperature could be used to determine when alveolar gas is exhaled. One method utilizes a flow sensor to detect starting and completion of exhalation. A processor may be provided as a data processing/control unit for automatically detecting the signal from the flow sensor to control sampling of exhaled breath. In a preferred embodiment, the exhaled breath sample is collected at end-tidal breathing.

Single or multiple samples collected by the known in-line (or mainstream) sampling method are preferable, but if sensor acquisition time is reduced, side stream sampling may be used. With in-line sampling, a sensor of the subject invention could be placed proximal to an endotracheal (ET) tube directly in the gas stream. In the latter, samples are collected through an adapter at the proximal end of an ET tube and drawn through thin bore tubing to a condensate extracting system of the subject invention. In certain embodiments that use in-line sampling, the condensate extracting system and sensor are placed in a sampling chamber positioned within the subject's gas stream for patients requiring endotracheal intubation and frequent glucose monitoring. Alternatively, to sample end-tidal gas, samples can be taken throughout the exhalation phase of respiration where with each sample, condensates are extracted and analyzed with a sensor and an average glucose value determined and correlated with blood glucose concentration. Depending on the sample size, extracting time, and sensor response time, exhaled gas may be collected on successive cycles.

Referring now to FIG. 1, the upper frame demonstrates a capnogram of a single respiratory cycle. The initial gas that is exhaled is deadspace gas (Phase II of the capnogram), followed by gas that is a mixture of deadspace and alveolar gas. Finally, only alveolar gas is exhaled (Phase III). When exhalation is terminated and inspiration begins (Phase IV) there is no long $CO_2$ present in the sample. For accurate blood level correlation, samples are taken at the point labeled "$P_{et}CO_2$" or Phase III, which reflects the $CO_2$ concentration in the lung. As noted above, condensates extracted from an end-tidal sample will correlate best with blood concentration.

In one embodiment, samples are collected at the distal end of an ET tube through a tube with a separate sampling port. This may improve sampling by allowing a "cleaner—(less deadspace)" sample during each respiratory cycle.

In certain embodiments, condensate is extracted from a subject's exhaled breath sample using any one of many known devices for extracting condensates. One such device relies on gravity to form a condensate pool from which a sample for testing may be drawn. These types of devices require that condensate droplets become large enough to overcome water's naturally tendency to stick to the walls of a collecting tube. Eventually, the amount of condensate in the collection area becomes large enough for analysis. In some cases, the collecting tube is inserted into an ice bucket or may even be separately cooled by refrigeration systems in order to increase the amount and speed of condensate formation. In other cases, a Teflon™ or other hydrophobic polymer coated collecting tube is applied to collecting tubes to make the tube walls non-wetting and non-reactive with glucose and to enhance the speed and amount of condensate collected.

A preferred method for increasing the amount and speed of condensate formation comprises the use of a Peltier device, which can cool and/or heat a collecting tube. An advantage of the Peltier device is that it can be cooled to improve the rate and volume of condensation, and following cooling, rapidly heat the resultant condensate to a temperature that is ideal for the sensor to function. This is particularly advantageous where the sensor is a glucose-binding molecule such as an enzyme.

Figure 4:
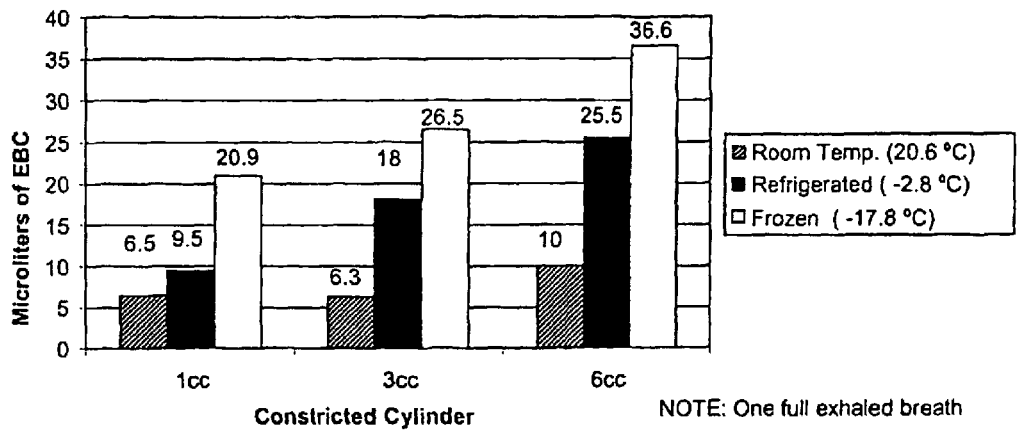
FIG. 4 is a graphical illustration of the volume of EBC collected based on temperature and the size of the collection device, where the sample of EBC is based on one full exhaled breath.
Figure 5A:
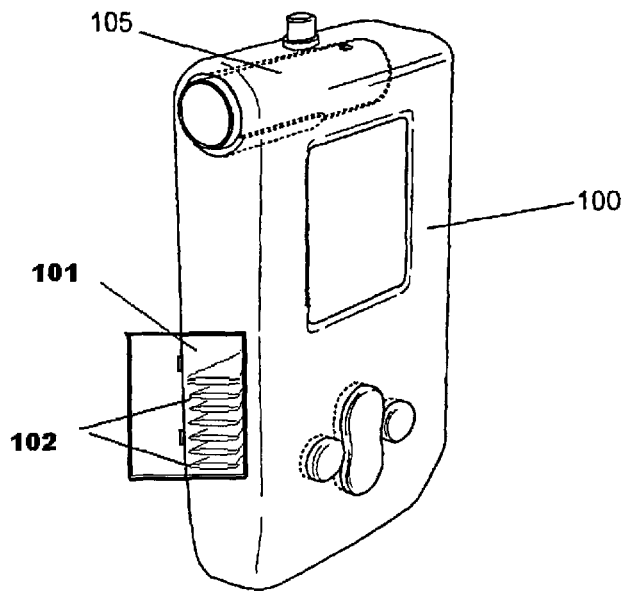
FIGS. 5A-5G show various representations of a portable device of the invention for detecting glucose in exhaled breath.
Figure 5B:
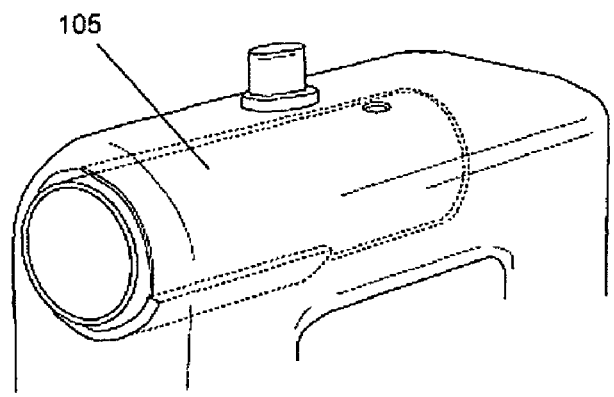
Figure 5C:
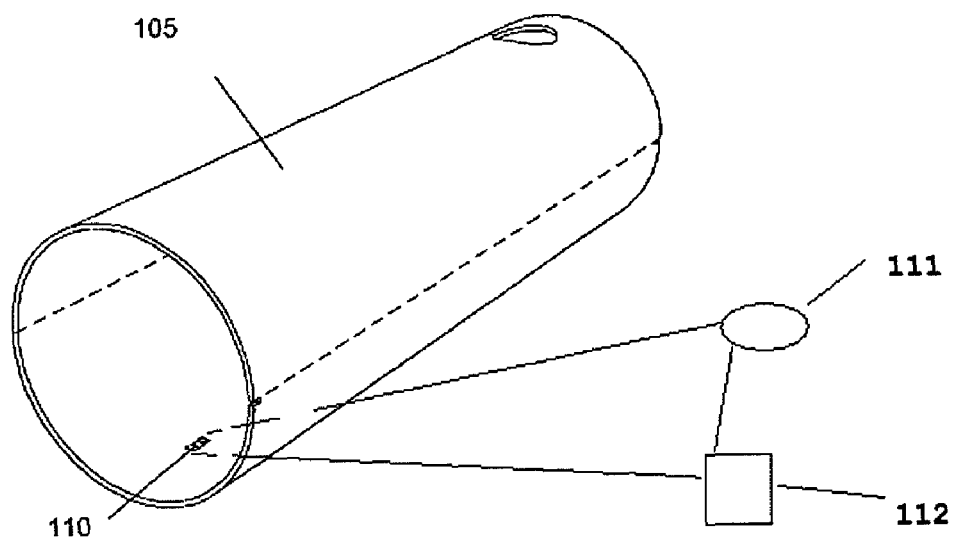
Figure 5D:
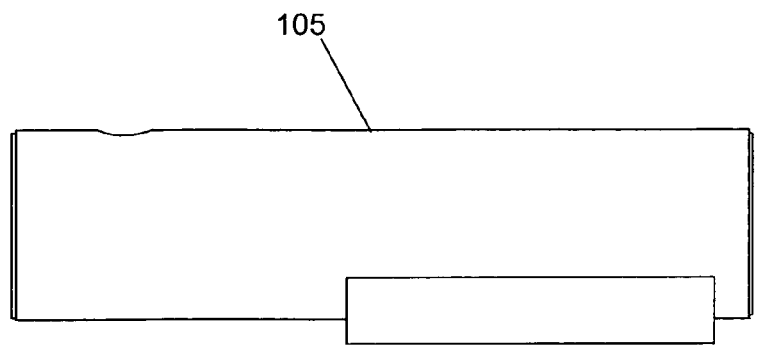
Figure 5E:
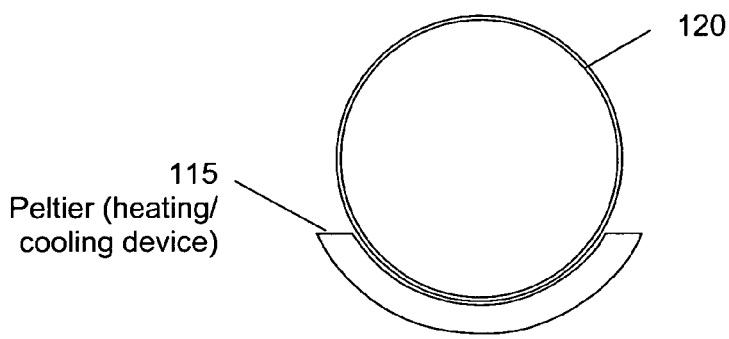
Figure 5F:
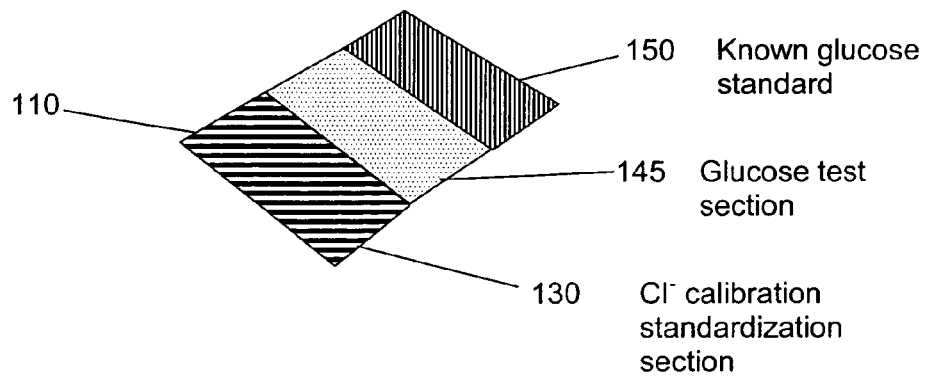
Figure 5G:
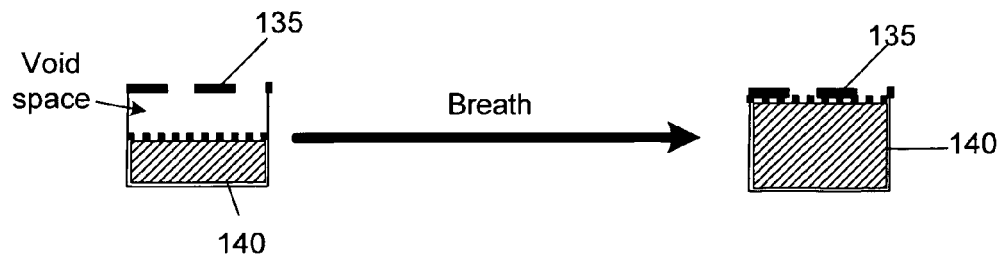

A condensate extracting system of the invention can be made with easily available materials. As understood by the skilled artisan, the amount of EBC that can be collected may be manipulated based on the size of the condensate extracting system and the temperature at which the system is exposed (see, FIG. 4). In one embodiment, the invention provides a device for determination of the content of glucose in EBC, which comprises: a conduit having a condensing unit with an inlet and an outlet (the inlet can be configured to fit with a mechanical respirator or, for direct use by the patient, an inlet assembly providing one-way ingress of ambient atmosphere to the device can be associated with the inlet of the conduit condensing unit); a coolant substance completely or partially surrounding said condensing unit; and, in enclosed fluid communication with said conduit condensing unit outlet, a sensor. In a preferred embodiment, the device is disposable and inexpensive, and is used to collect human exhaled breath for assay of liquid phase glucose to assist in evaluation of blood glucose concentration.

In a related embodiment, the condensing unit consists of one tubing unit that is partially or completely surrounded by a coolant substance. Preferably, the cooling substance is a coolant jacket that contains water, or a substance with a high thermal capacity and is chemically inert. The device can also be made, as described above, without refrigerant or cooling substance, utilizing a gas/membrane or gas/aqueous reaction compartment.

In another embodiment, the condensate extracting system is comprised of cold tolerant materials and consists of two tubing units, one inside the other. Surrounding the inner tube or set of tubes, and contained by the outer tube, is a cooling substance which has a high thermal capacity and is chemically inert, and therefore, once frozen, can maintain freezing temperatures for an extended period of time. The disposable unit can be frozen in a standard size home freezer and then connected together with an exhaled breath sampling system and sensor as a compact integral unit.

In certain embodiments, attached to the proximal portion of the unit is a port, to which a mouthpiece can be attached, through which the patient breathes. This consists of two one-way valves that direct atmospheric air or selected gases to the patient's lungs during inspiration, and channel exhaled gas down a condensing tube. Gas moves in only one direction through the condensing apparatus.

Certain embodiments of invention include, inserted between the breathing port's mouthpiece and the condensing chamber, a microporous filter which traps all small particles (such as saliva or sputum), is impermeable to liquids, but allows gas and vaporized fluids of less than 0.3 microns in diameter to pass. This acts as a saliva trap and may also act as a filter for the larger fluid particles which may be aerosolized in the larger airways.

The distal end of the condensing chamber tube(s) is attached to a collecting apparatus which utilizes gravity to trap condensed fluid. At the bottom of this trap is a clear plastic collection reservoir in which the sample is sequentially warmed and contacted with sensor technology.

In certain embodiments an aerosol "impactor" system may be used to selectively collect aerosol droplets of a particular size. Impactors work by passing a sample, such as exhaled breath, through a series of increasingly smaller openings (such as screens) to selectively trap and collect particles (or aerosol droplets) of a particular size. Ideally, for determinations of EBC glucose quantity, the aerosol droplets collected from an EBC sample should be in the 0.5-2.0 uM range. For exhaled breath, the sample would be maintained at 37° C. or higher to prevent the condensation of breath and therefore the addition of the free water to the aerosol droplets. The aerosol droplets should have a higher glucose concentration than in EBC.

Preferably, the patient breathes comfortably in and out through the mouthpiece. More preferably, one or two breaths are sufficient to assess glucose concentration in accordance with the subject invention. Lung fluid vapor collects on the inner surface of the inner tube(s) of the condensing apparatus starting immediately. Gravity carries the larger droplets down the tube, these droplets recruiting other small droplets on their trip to the collecting vial distally. Alternatively, after a fixed period of tidal breathing, the condensed fluid can be expressed down the inner tube with a device similar to a syringe plunger (also referred to herein as a moveable valve). Aqueous phase glucose can be measured by standard assays or sensor technology (either simultaneously with EBC sampling or at a later time and place), and can be reasonably quantified by simple tests performed by patients in their homes.

In order to practice the method employing the device, the cooling substance (or cooling jacket) is cooled to a temperature lower than that of the collecting tube prior to use (such as, with the cooling jacket, prior to being slid over the tube). Air is inhaled by a patient user through the mouthpiece and exhaled through a movable valve into the collecting tube. In certain embodiments, after the passage of between about 30 seconds and five minutes of breathing, the cooling sleeve is removed from around the collecting tube, the movable valve is advanced through the tube thereby wiping away condensate formed on the interior walls of the tube causing that condensate to collect in a pool around the valve.

In a related embodiment, an airtight cap may be placed over the end of the collecting tube nearest the condensate pool in order to seal the collecting tube prior to storage and/or shipment to a testing location. At the test location, the airtight cap is removed and one or more sensor technology is introduced to the condensate. Testing may be performed after removing samples of the condensate from the collecting tube or by means of a probe placed into contact with the condensate pool or by insertion of chemicals or chemically impregnated strips. Alternatively, the collecting tube may include a sensor to which the condensate pool is exposed to provide immediate detection and/or quantification of glucose present in the condensate pool.

The device of the invention is intended to be used to condense the fluid normally exhaled in breath by a subject and to gather this fluid in such a manner and in such volume that tests may be performed on the condensate. These tests include measuring glucose concentration, as well as the concentration of other characteristics, chemicals and compounds of biologic interest.

The present invention includes several collection devices designed to allow rapid (e.g., less than five minutes, preferably less than 30 seconds), noninvasive collection of EBC from a spontaneously breathing subject or a patient receiving mechanical ventilation, followed by one-step quantitative or semi-quantitative analysis of the condensate for the concentration of glucose. In spontaneously breathing subjects, the exhaled condensate may generally be collected via a mouthpiece held by the lips; however, in patients with severe respiratory distress, the sample may be collected by fitting the patient with an airtight, snug-fitting facemask that allows the delivery of oxygen, while allowing the diversion of exhaled gases and aerosol into a condensing chamber such as those described above.

Glucose could be monitored intermittently or continuously in a wide range of environments. Small handheld portable equipment could be used by subjects in the home, at work, in nursing homes or while they are ambulatory, while other devices could be designed for continuous monitoring in the operating room, intensive care units and in other areas of hospitals or other healthcare facilities such as clinics, doctors offices where this capability would be valuable.

Such small handheld portable equipment may be used by an unskilled layperson, then sealed for transport to a laboratory where subsequent analysis may be performed. Alternatively, the device may also function as part of a home- or workplace-diagnostic device constructed to accept the device and perform the required measurements automatically. Additionally, it may be used in any setting without additional devices, by adding chemical reagents or test strips to detect chemical features and compounds of interest.

Accordingly, as illustrated in FIGS. 5A-5G, one embodiment of the invention comprises a simple self-contained and portable device 100 for efficiently collecting, storing, analyzing, and/or shipping condensate derived from the exhaled breath of a subject wherein the wettable components of such a device may be disposable.

Another embodiment of the invention provides a method for collecting condensate derived from the exhaled breath of a subject that is fast, simple, efficient and performable by nonprofessional personnel.

A further embodiment of this invention provides a device and method in which condensate samples collected from the exhaled breath of a user may be both collected and subjected in situ to various laboratory tests, including ones for measuring glucose levels, without the risk of contamination by exposure to influences external to a collecting tube.

Yet another embodiment of this invention provides a condensate collecting device that may be made available for use in a subject's home or workplace. In a related embodiment, a device is provided in which condensate may be collected, stored and transported in a single unit.

In a preferred embodiment, the subject glucose monitoring system includes a container with disposable breathing tubes 105 , where the breathing tubes 105 each contain a sensor 110 (such as a glucose-binding molecule) and transduction method/signaling means 111. The breathing tubes are in a collapsed state (flat or crescent shaped) to enable ease of storage of several tubes (such as 25-50 tubes) to a container. Alternatively, the disposable tubes are provided in individual wrappers (such as foil or plastic wrappers).

In a preferred method of use, the subject removes a breathing tube from the container (or individual wrapper) and places the tube in an exhaled breath sampling device containing a cooling means 115 that is in close proximity to a portion of the breathing tube, such as the portion of the breathing tube that contains the sensor. The exhaled breath sampling device is preferably portable and handheld. In certain embodiments, the exhaled breath sampling device also includes a means to determine the phase of the exhaled breath sample (such as a $CO_2$ sensor, pressure transducer, flow sensor, or temperature or humidity sensor) so that a specific portion of the exhaled breath sample is directed, collected, and condensed in the tube.

If the breathing tube is in a collapsed state, it will open to form a circular 120 or oval cross-section as it is placed into the exhaled breath sampling device. The sensor and transduction means are preferably embedded to a wall of the breathing tube and have electrode contacts that transmit electrical signals from the tube to the exhaled breath sampling device. These contacts are useful in improving the rate of cooling of a portion of the breathing tube (preferably the area on which the sensor and transduction means are located).

Once the breathing tube is placed in the exhaled breath sampling device, the cooling means (such as a Peltier device) is activated and, when a predetermined temperature is reached (such as 10-15° C. below body temperature), the device alerts the subject to take a deep breath and blow slowly through the breathing tube. A feedback means, such as a graphical display, can be provided in the exhaled breath sampling device to coach the subject to breath at an appropriate flow rate and to a predetermined tidal volume. Depending on what portion of the breath is preferred (such as the end-tidal breath), a two way valve can be provided with the exhaled breath sampling device to exhaust a portion of the breath to the atmosphere before directing the preferred portion of the breath into the breathing tube, where it is condensed by the cooling means to a portion of the tube. Preferably, the breath sample is condensed on the portion containing the sensor and transduction means.

According to one embodiment of the subject invention, the subject need only provide a single breath sample to the exhaled breath sampling device. However, if additional breaths are necessary to collect an adequate EBC sample, the device can include a means for notifying the subject to take additional breaths and continue to blow into the breathing tube. For example, a graphical display can be used to request additional breaths from the subject.

In certain embodiments, the sensor is embedded and freeze dried within a hydrogel polymer 140 that is highly hydrophilic. In certain embodiments, a partial drying of the hydrogel is performed prior to freeze-drying to cause the hydrogel to lose volume and provide optimum swelling behavior for glucose detection. In a related embodiment, pore formers are used during fabrication of the hydrogel polymer to speed hydration. Such pore formers are molecules similar to monomers or solvents but are non-reactive. They are removed during freeze drying of the hydrogel and can lead to pores of various sizes being formed through phase separation prior to solidification of the hydrogel. These large pores help speed the rate of hydration of the hydrogel by increasing the association of the hydrogel with water.

When a portion of the tube containing the hydrogel with the sensor and transduction means is cooled and exposed to exhaled breath condensates, the hydrogel 140 will rapidly expand because it is highly hydrophilic. Generally, the hydrogel will expand until it is fully hydrated with a precise volume of condensate. Once the hydrogel is fully hydrated, the cooling means is turned off.

In certain embodiments, the device may further include a means for heating the breathing tube (after obtaining an appropriate amount of EBC sample) to a desired temperature. A heating means will prevent additional condensate from forming on the hydrogel as well as improve the rate of the sensing reaction, especially if an enzyme is used as a glucose-binding molecule that is embedded in the hydrogel.

In certain embodiments, impactors heated to 37° C. or higher are introduced into the path of the exhaled breath to separate aerosol particles of a particular size (ideally 0.5-2.0 uM). Once these particles pass through the impactors, they can be absorbed into the hydrogel by cooling the surface with the Peltier device.

In an alternative embodiment, the impactor screen that traps aerosol droplets of the preferred size is cooled with the Peltier, while screens for larger droplets are maintained at 37° C. or higher so that only the preferred sized droplets are collected for analysis.

In certain embodiments, an electrolyte sensor, such as a sodium or chloride electrode, is precisely positioned above the hydrogel. As the hydrogel swells, it will contact the electrode, creating a signal, at which time the subject will be signaled to stop breathing through the breathing tube or the breath will be diverted by the device. Since the hydrogel can only absorb a finite and reproducible volume of fluid, the volume of EBC collected will be consistent and known. However, it is desirable for the subject to stop breathing or for the flow to be diverted at this point since additional condensate could form above the hydrogel and potentially allow for the diffusion of additional glucose which would give a faulty high reading.

In another embodiment, a screen or miniature pressure transducer 135 can be placed above the hydrogel pad. When the hydrogel swells to maximum capacity, it will contact the screen, completing an electrical circuit and indicating that the subject should stop blowing into the device or for diversion of the remainder of the breath.

Alternatively, the miniature pressure transducer can sense when the hydrogel is swelled and provide feedback to the subject to stop blowing.

In addition to a means to detect when the hydrogel has swelled completely, a portion of the sensor can consist of an electrode that measures chloride 130 or other electrolytes or conducting compounds. The chloride concentration in blood is tightly regulated and alveolar lining fluid will contain a chloride concentration virtually identical to blood. However, as aerosol droplets traverse the lung additional free water is added to the exhaled breath and the concentration of chloride is diluted, especially if a condensate of aerosol droplets and humidity is formed. Despite this dilution, the concentration of chloride in EBC is also relatively constant and correlates with the blood chloride concentration. Thus measurement of chloride in the EBC can be used to determine whether the collected sample is diluted or concentrated. Low chloride concentrations indicate that the sample has been diluted and the measured glucose concentration will be lower than if the condensate were more concentrated. The ratio of the measured chloride concentration to that normally found in EBC can be used to calculate the true glucose concentration in the condensate and then to calculate the blood glucose concentration. Similar calculations can be used if the condensate concentration of chloride is high.

In another preferred embodiment, a second dehydrated hydrogel pad can be included as part of the sensor 110 for simultaneous calibration. This hydrogel pad will not only contain a glucose sensor (such as an enzyme) 145, but also a "standard" or calibration sensor 150. The calibration sensor 150 will include a known quantity of glucose against which the accuracy and/or quantity of the glucose detected in EBC can be confirmed. For example, where both the quantity of glucose and the volume of EBC absorbed by the hydrogel are known, the concentration of glucose can be calculated.

Alternatively, the glucose can be sprayed or otherwise applied above the dehydrated hydrogel during production and will be absorbed when EBC is condensed on it. It is known in the art of glucose test strip manufacturing that enzymes can be inactivated by temperature and humidity and that, especially when enzymes kinetics are used for glucose determinations, the glucose concentration can be artificially elevated at higher temperatures. In one recent study, (Adverse Impact of Temperature and Humidity on Blood Glucose Monitoring Reliability: A Pilot Study. M J Haller, J J Shuster, D Schatz, and Richard Melker, Diabetes Technology and Therapeutics, submitted) some test strips read 1 mg/dL higher for each 1° C. increase in temperature. Since the concentration on the calibration portion of the sensor is known, the total glucose measured on that sensor is the concentration in EBC plus the known concentration. The concentration measured on the glucose measuring hydrogel sensor is only the concentration in the EBC. The difference in the measured concentrations should always equal the known concentration applied to the calibration portion of the sensor.

For example, if the concentration of glucose on the calibration sensor is 100 ng/mL and the EBC concentration is 100 ng/mL, then the glucose sensing electrode should read 100 ng/mL and the calibration sensing electrode should read 200 ng/mL (EBC plus control). If, however, the sensors are inadvertently exposed to high temperature (left in an automobile in the summertime) and the enzyme activity is decreased by 20%, the glucose sensing electrode will only read 80 ng/mL and the calibration electrode 160 ng/mL. Since the difference between the glucose concentration from the glucose sensing electrode and the calibration electrode is only 80 ng/mL instead of 100 ng/mL, it is clear that the result is 20% too low and depending on the degree of enzyme inactivation, the device can indicate to the subject that the sensors are defective and should be discarded, or if the degree of inactivation is in an acceptable range, the correct glucose concentration can be calculated. This same embodiment could be incorporated into glucose test strips that measure glucose in blood.

In a related embodiment, the hydrogel sensor includes a glucose sensor 145 and calibration sensor 150 that contains a known concentration of glucose, where the calibration sensor is coated or covered with a membrane or compound that allows passage of water from EBC but does not allow glucose to cross and swell the hydrogel. In this embodiment, the calibration sensor measures the known concentration of glucose, which can be used to determine the status of the glucose sensor (such as the status of a glucose binding molecule or enzyme) and to calculate the true glucose concentration in EBC if sensor/enzyme degradation has occurred. The calibration sensor also ensures that all components of the hydrogel sensor measuring system are working correctly.

Preferably, it will take approximately 30 seconds from the time the subject breaths into the device until it displays the blood glucose concentration based on the concentration found in the exhaled breath sample.

Detection and/or Monitoring of Glucose

According to the subject invention, colorimetric techniques, reflectance photometry, and/or electrochemistry (amperometry) are used in combination with molecular recognition entities (or MREs, such as aptamers, enzymes, antibodies, amplifying fluorescent polymers (AFPs), and the like) as described herein to detect and/or quantify the glucose present in a sample of EBC. The glucose must interact (e.g., react with an enzyme or bind to an aptamer or antibody) which creates some measurable change (temperature, color, current, voltage, etc.). This change is then detected by a transduction mechanism. The degree of change is proportional to the glucose concentration in the EBC sample. A sensor includes both the detection and transduction mechanisms. For instance, glucose oxidase combines with glucose and changes the current in a circuit. The change in current is the transduction mechanism. Aptamers are molecular recognition entities and AFPs can be either MREs, transduction molecules or both. Colorimetry, reflectance photometry and electrochemistry can be either transduction mechanisms or both.

According to the subject invention, there are several ways to use enzymes for sensing glucose. The most common strategy involves enzymatic oxidation of glucose to an oxidized by-product and an equivalent amount of hydrogen peroxide. The electrochemistry involves measuring the current involved in oxidizing (more common) or reducing the hydrogen peroxide. The 1:1 stoichiometry allows back-calculation of the glucose level. The other approach is to directly "wire" a redox enzyme to an electrode and measure the current required to reduce or oxidize glucose directly.

When enzymes are used to catalyze reactions that convert glucose to a measurable substance preferred enzymes of the subject invention are those that are specific for glucose and produce substances that are readily measured by methods described herein. As a result, routine glucose measurements from exhaled breath sampling are rapid, accurate, and sensitive. Contemplated enzymes for use in accordance with the subject invention include, but are not limited to, glucose oxidase, glucose dehydrogenase, glucose-6-dehydrogenase, and hexokinase.

Figure 2A:
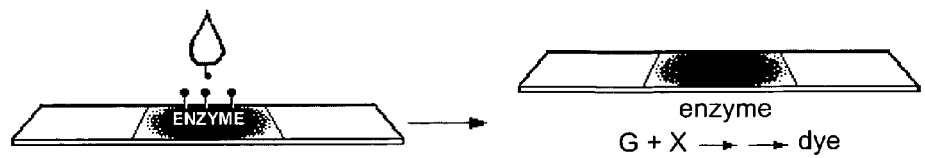
FIGS. 2A-2D show various methods for detecting glucose in EBC, which may be utilized in accordance with the present invention.

For example, with colorimetric techniques, an enzyme is used as a catalyst and glucose is reacted with a compound that is capable of generating a colored product or dye (See FIG. 2A). The amount of colored product generated is directly proportional to the amount of glucose present in the sample. Thus, the more glucose present in the sample, the more intense the color; whereas the less glucose present, the less intense the color.

Figure 2B:
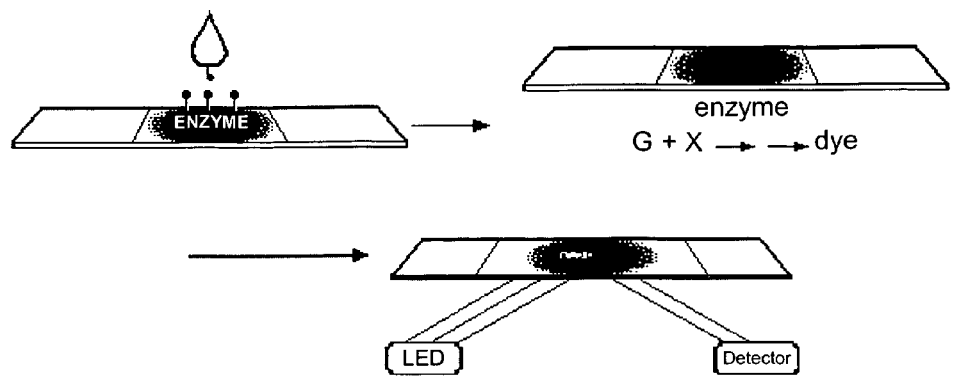

Reflectance photometry quantifies the intensity of the colored product generated by the enzymatic reaction. A light source, such as a light-emitting diode (LED) emits light of a specific wavelength onto a test strip that includes the colored product (generated as described above). Since the colored product absorbs that wavelength of light, the more glucose in a sample (and thus the more colored product on the test strip), the less reflected light (see FIG. 2B. A detector captures the reflected light, converts it into an electronic signal, and translates that signal to its corresponding glucose concentration.

Figure 2C:
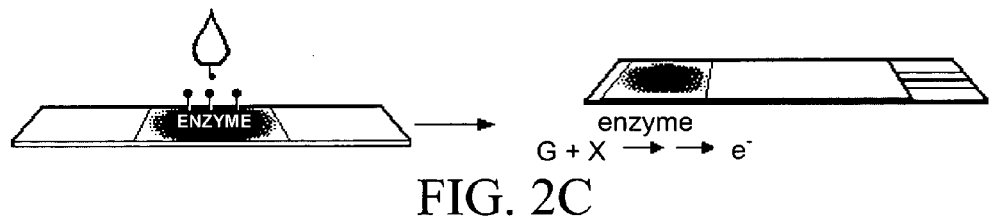

With electrochemistry (amperometry), an enzyme is used as a catalyst to react glucose with a mediator to generate electrons ($e^-$) (see FIG. 2C). The number of electrons captured by the mediator is directly proportional to the amount of glucose present in the sample. Thus, the more glucose present in the sample, the more electrons; whereas, the less glucose, the fewer electrons.

Figure 2D:
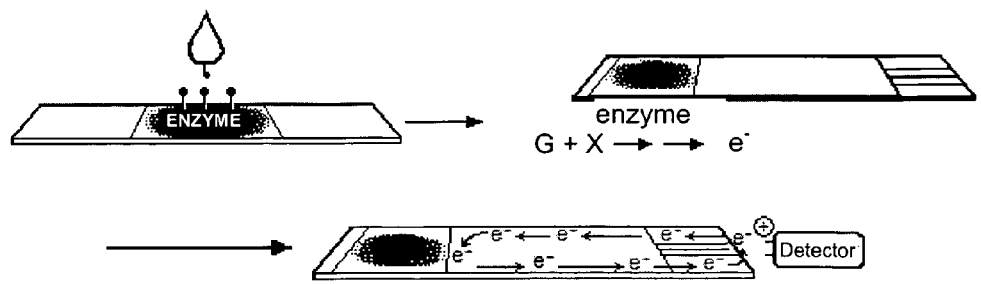

Electrochemistry quantifies the number of electrons generated by the oxidation of glucose. A mediator captures the electrons. When a voltage is applied, the electrons are transferred and counted at the electrodes. A detector converts the resulting current to an electronic signal and translates that signal to its corresponding glucose concentration (see FIG. 2D).

In one embodiment, to detect glucose in a sample of EBC, one or more collection reservoirs are placed in contact with a sensor of the invention. Ionically conductive material is present within the collection reservoir, which is also in contact with a sensing electrode of the sensor, which generates a current in proportion to the amount of glucose present in the reservoir.

The sensing electrode can be, for example, a Pt-comprising electrode configured to provide a geometric surface area of about 0.1 to 3 $cm^2$, preferably about 0.5 to 2 $cm^2$, and more preferably about 1 $cm^2$. This particular configuration is scaled in proportion to the collection area of the collection reservoir used in the sampling system of the present invention, throughout which the extracted analyte and/or its reaction products will be present. The electrode composition is formulated using analytical- or electronic-grade reagents and solvents which ensure that electrochemical and/or other residual contaminants are avoided in the final composition, significantly reducing the background noise inherent in the resultant electrode. In particular, the reagents and solvents used in the formulation of the electrode are selected so as to be substantially free of electrochemically active contaminants (e.g., anti-oxidants), and the solvents in particular are selected for high volatility in order to reduce washing and cure times. Some electrode embodiments are described in European Patent Publication 0 942 278 A2, published Sep. 15, 1999, herein incorporated by reference in its entirety.

The reactive surface of the sensing electrode can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof. Some catalytic materials, membranes, and fabrication technologies suitable for the construction of amperometric biosensors were described by Newman, J. D., et al. (Analytical Chemistry 67(24), 4594-4599, 1995, herein incorporated by reference in its entirety).

Any suitable electrode system can be employed, an exemplary system uses a silver or silver/silver chloride (Ag/AgCl) electrode system. Reference and counter electrodes are formulated typically using two performance criteria: (1) the electrodes are capable of operation for extended periods, preferably periods of up to 24 hours or longer in cases where repeated measurements are necessary, as might be the case in the operating room or ICU.; and (2) the electrodes are formulated to have high electrochemical purity in order to operate within the present system which requires extremely low background noise levels. The electrodes must also be capable of passing a large amount of charge over the life of the electrodes. With regard to operation for extended periods of time, Ag/AgCl electrodes are capable of repeatedly forming a reversible couple which operates without unwanted electrochemical side reactions (which could give rise to changes in pH, and liberation of hydrogen and oxygen due to water hydrolysis). The Ag/AgCl electrode is thus formulated to withstand repeated cycles of current passage in the range of about 0.01 to 1.0 mA per $cm^2$ of electrode area. With regard to high electrochemical purity, the Ag/AgCl components are dispersed within a suitable polymer binder to provide an electrode composition which is not susceptible to attack (e.g., plasticization) by components in the collection reservoir, e.g., the hydrogel composition. The electrode compositions are also typically formulated using analytical- or electronic-grade reagents and solvents, and the polymer binder composition is selected to be free of electrochemically active contaminants which could diffuse to the biosensor to produce a background current.

Preferably, a sensing electrode is used for detecting at nominal concentration levels glucose from the extracted EBC in the collection reservoir(s). Suitable exemplary sensing electrodes that can be used in accordance with the present invention are described in PCT Publication Nos. WO 97/10499, published 20 Mar. 1997 and WO 98/42252, published 1 Oct. 1998, both of which are incorporated by reference in their entirety.

To detect glucose, an enzyme (or enzymes) is disposed within the one or more collection reservoirs. The selected enzyme is capable of catalyzing a reaction with the extracted glucose to the extent that a product of this reaction can be sensed, e.g., can be detected electrochemically from the generation of a current that is detectable and proportional to the amount of the glucose that is reacted. Examples of suitable enzymes include, but are not limited to, glucose oxidase, glucose dehydrogenase, glucose-6-phosphate, dehydrogenase, and hexokinase.

In one embodiment of the present invention, a suitable enzyme is glucose oxidase, which oxidizes glucose to gluconic acid and hydrogen peroxide. The subsequent detection of hydrogen peroxide on an appropriate sensing electrode generates two electrons per hydrogen peroxide molecule creating a current that can be detected and related to the amount of glucose present in the sample. Glucose oxidase (GOx) is readily available commercially and has well known catalytic characteristics. However, other enzymes can also be used singly or together, as long as they specifically catalyze a reaction with glucose to generate a detectable product in proportion to the amount of glucose so reacted. For example, dehydrogenase-based sensors can be implemented in accordance with the enzyme glucose detections systems described above, where such enzyme systems operate on much the same general techniques and use working electrodes made of gold or carbon (via mediated chemistry).

Upon reaction of glucose with an enzyme, the detected current is then correlated with the subject's blood glucose concentration (e.g., using a statistical technique or algorithm or combination of techniques as described herein) so that a system controller may display the subject's actual blood glucose concentration as measured by the sampling system. Such statistical techniques can be formulated as algorithm(s) and incorporated in one or more microprocessor(s) associated with the sampling system. Exemplary signal processing applications include, but are not limited to, those taught in the following U.S. Pat. Nos. 6,144,869, 6,233,471, 6,180,416, herein incorporated by reference in their entirety.

In a further aspect of the present invention, the sampling/sensing mechanism and user interface may be found on separate components. Thus, the monitoring system can comprise at least two components, in which a first component comprises a sensing mechanism that is used to detect glucose, and a second component that receives the glucose data from the first component, conducts data processing on the glucose data to determine glucose concentration and then displays the glucose concentration data.

Typically, microprocessor functions (e.g., a sensing device, aspects of the measurement cycle, computational methods, different aspects of data manipulation or recording, etc.) are found in both components. Alternatively, microprocessing components may be located in one or the other of the at least two components. The second component of the monitoring system can assume many forms, including, but not limited to, the following: a watch, a credit card-shaped device (e.g., a "smart card" or "universal card" having a built-in microprocessor as described for example in U.S. Pat. No. 5,892,661, herein incorporated by reference in its entirety), a pager-like device, cell phone-like device, or other such device that communicates information to the user visually, audibly, or kinesthetically.

Further, additional components may be added to the system, for example, a third component comprising a display of glucose values or an alarm related to glucose concentration, may be employed. In certain embodiments, a delivery unit is included in the system. An exemplary delivery unit is an insulin delivery unit. Insulin delivery units, both implantable and external, are known in the art and described, for example, in U.S. Pat. Nos. 5,995,860; 5,112,614 and 5,062,841, herein incorporated by reference in their entirety. Preferably, when included as a component of the present invention, the delivery unit is in communication (e.g., wire-like or wireless communication) with the extracting and/or sensing mechanism such that the sensing mechanism can control the insulin pump and regulate delivery of a suitable amount of insulin to the subject.

Insulin is recently available in an inhaled form. In one embodiment, the subject EBC glucose measuring device could be incorporated into an inhaled insulin device. The subject could blow into the glucose measuring device and based on the glucose concentration, inhaled insulin could be metered to the subject.

The subject invention can utilize any known hydrogel to immobilize glucose-binding molecules, including but not limited to, PHEMA, polyvinyl alcohol, and polyelectrolyte complexes like chitosan/alginate. Freeze drying involves freezing the solid and a applying a vacuum to remove water. The process for freeze-drying hydrogels is well-known in the art (see, for example, U.S. Pat. No. 5,409,703, which is incorporated by reference in its entirety).

Different sensing devices and/or sensing systems can be employed as well to distinguish between signals. For example, a first gel containing glucose oxidase associated with a first platinum sensor can be used for the detection of glucose, while a second gel containing uricase associated with a second platinum sensor can be used for the detection of urea.

Chemical Derivatization Prior to Glucose Detection

In many analytical applications (e.g., GC/MS), the analyte must be in the gas phase before separation and/or detection can take place. If the analyte does not have a sufficiently high vapor pressure, and does not have the thermal stability to allow rapid heating to effect volatilization, the analyte can be chemically derivatized to a more volatile and/or stable structure. Chemical derivatization can also be used to increase the detector response for an analyte by incorporating functional groups which lead to higher detector signals (such as the fluorescent labels fluorescein and rhodamine). The chemical derivatization reaction or reactions can occur on the surface of the collection vessel or after the derivatizing reagents are added to the vessel. Alternatively, glucose could be transferred from the collection vessel to the detection device, and derivatization could occur while the glucose is in transfer or after it contacts the detection device.

Figure 6:
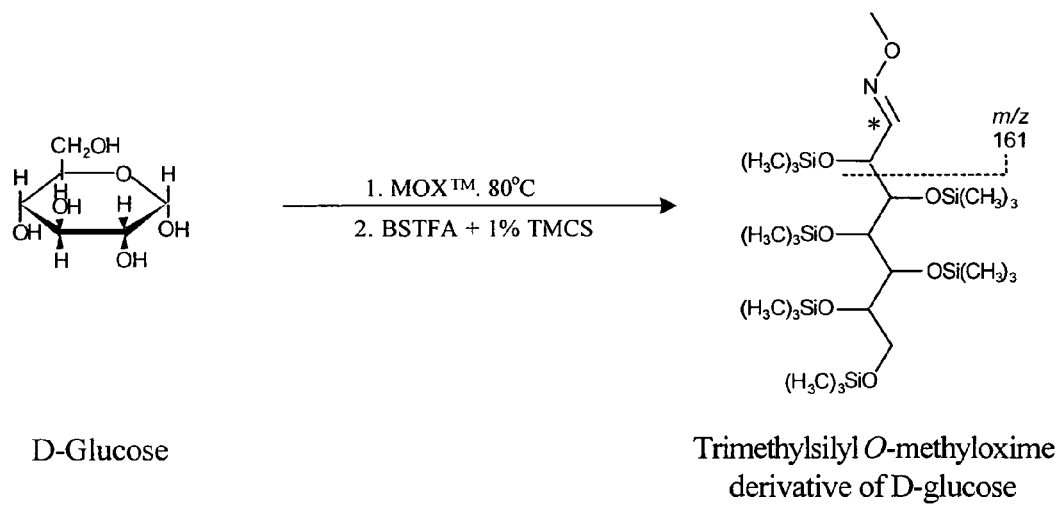
FIG. 6 is an illustration of a glucose derivatization reaction in accordance with the subject invention.

In the case of glucose, methods involving the formation of fully and partially methylated methyl glycosides, acetates, acetals, trimethylsilyl ethers, and alditol acetate derivatives of monosaccharides are typically used (McInnes et al., "Separation of carbohydrate derivatives by gas-liquid partition chromatography," *Journal of Chromatography,* 1:556-57 (1958); Bishop and Cooper, "Separation of carbohydrate derivatives by gas-liquid partition chromatography," *Canadian Journal of Chemistry,* 38:388-95 (1960); Bishop "Gas-liquid chromatography of carbohydrate derivatives," *Ad Carbohydr Chem,* 19:95-147 (1964); Lehrfeld, "Differential gas-liquid chromatography method for determination of uronic acids in carbohydrate mixtures," *Analytical Biochemistry,* 115:410-18 (1981); and Blakeney et al., "A simple and rapid preparation of alditol acetates for monosaccharide analysis," *Carbohydrate Research,* 113:291-99 (1983), all of which are incorporated by reference in their entirety). An example of a trimethylsilyl O-methyloxime derivative with MOX™ Reagent (Methoxyamine HCL in Pyridine) and BSTFA+1% TMCS for glucose is shown in FIG. 6.

Sensor Technology

A number of patents which describe analyte monitoring technology that can be used in the subject invention include, but are not limited to, the following: U.S. Pat. Nos. 5,945,069; 5,918,257; 4,938,928; 4,992,244; 5,034,192; 5,071,770; 5,145,645; 5,252,292; 5,605,612; 5,756,879; 5,783,154; and 5,830,412. Other sensors suitable for the present invention include, but are not limited to, semiconductive sensors, metal-insulator-metal ensemble (MIME) sensors, cross-reactive optical microsensor arrays, fluorescent polymer films, surface enhanced raman spectroscopy (SERS), diode lasers, selected ion flow tubes, metal oxide sensors (MOS), non-dispersive infrared spectrometer, bulk acoustic wave sensors, surface acoustic wave sensors, colorimetric tubes, functionalized microcantilevers and infrared spectroscopy. For example, with semiconductive sensors, detection of glucose using a glucose-binding molecule can cause a change in the electrical properties of semiconductor(s) by making their electrical resistance vary, and the measurement of these variations allows one to determine the concentration of glucose present.

In accordance with the subject invention, glucose monitoring devices for detecting/quantifying glucose utilize a relatively brief detection time of around a few seconds. Other recent analyte sensing technologies contemplated by the present invention include apparatuses having conductive-polymer sensors ("polymeric"), aptamer biosensors, and amplifying fluorescent polymer (AFP) sensors.

A conductive-polymer sensing device (also referred to as "chemoresistors") of the subject invention has a film made of a conductive polymer sensitive to the glucose molecules. Prior to exposure of the conductive polymer to glucose, the polymer exhibits a specific electric resistance that is detectable by the sensing device. On contact with glucose molecules, the reaction of the polymer with glucose causes a change in the electric resistance, and the measurement of the variation of this resistance enables the concentration of the glucose to be determined. An advantage of this type of sensor is that it functions at temperatures close to room temperature.

Responses of polymeric sensing devices to glucose can be fully characterized using a combination of conventional sensor characterization techniques. For example, the sensing device can be attached to a computer. The results can be displayed on the computer screen, stored, transmitted, etc. A data analyzer can compare a pattern of response to previously measured and characterized responses for glucose. The matching of those patterns can be performed using a number of techniques, including neural networks. By comparing the analog output from the polymer to a "blank" or control, for example, a neural network can establish a pattern that is unique to glucose and subsequently learns to recognize glucose. The particular resistor geometries are selected to optimize the desired response to glucose that is being sensed.

Another sensor of the invention can be provided in the form of an aptamer. In one embodiment, the SELEX™ (Systematic Evolution of Ligands by EXponential enrichment) methodology is used to produce aptamers that recognize glucose with high affinity and specificity. Aptamers produced by the SELEX methodology have a unique sequence and the property of binding specifically to a desired analyte. The SELEX methodology is based on the insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. According to the subject invention, glucose can thus serve as targets for aptamers. See also Jayasena, S., "Aptamers: An Emerging Class of Molecules That Rival Antibodies for Diagnostics," *Clinical Chemistry*, 45:9, 1628-1650 (1999).

Aptamer biosensors can be utilized in the present invention for detecting the presence of glucose in EBC samples. In one embodiment, aptamer sensors are composed of resonant oscillating quartz sensors that can detect minute changes in resonance frequencies due to modulations of mass of the oscillating system, which results from a binding or dissociation event (i.e., binding with glucose).

Molecular beacons (MB) and molecular beacon aptamers (MBA) employ fluorescence resonance energy transfer based methods to provide fluorescence signal increases in the presence of particular target sequences (such as glucose). See also, Stojanovic, Milan N., de Prada, Paloma, and Landry, Donald W., "Aptamer-Based Folding Fluorescent Sensor for Cocaine" J. Am. Chem. Soc. 2001, 123, 4928-4931 (2001); Jayasena, Sumedha D., "Aptamers: An Emerging Class of Molecules That Rival Antibodies of Diagnostics, Clinical Chemistry 45:9, 1628-1650 (1999).

Amplifying fluorescent polymer (AFP) sensors may be utilized in the present invention for detecting the presence of glucose in EBC samples. AFP sensors are extremely sensitive and highly selective chemosensors that use amplifying fluorescent polymers. When glucose molecules bind to thin films of the polymers, the fluorescence of the film decreases. A single molecule binding event quenches the fluorescence of many polymer repeat units, resulting in an amplification of the quenching. The binding of glucose molecules to the film is reversible, therefore the films can be reused.

Surface-acoustic-wave (SAW) sensors oscillate at high frequencies and generally have a substrate, which is covered by a chemoselective material. In SAW sensors, the substrate is used to propagate a surface acoustic wave between sets of interdigitated electrodes (i.e., to form a transducer). The chemoselective material is coated on the transducer. When glucose interacts with the chemoselective material coated on the substrate, the interaction results in a change in the SAW properties, such as the amplitude of velocity of the propagated wave. The detectable change in the characteristic wave is generally proportional to the mass load of glucose molecules present (i.e., concentration of glucose in EBC, which corresponds to the concentration of glucose in the blood stream).

Other types of chemical sensors known in the art that use chemoselective coating applicable to the operation of the present invention include bulk acoustic wave (BAW) devices, plate acoustic wave devices, interdigitated microelectrode (IME) devices, optical waveguide (OW) devices, electrochemical sensors, and electrically conducting sensors.

In a related embodiment, the sensor of the invention is connected to a computer, wherein any detectable change in frequency can be detected and measured by the computer.

In other embodiments, competitive binding immunoassays can be used to test an EBC sample for the presence of glucose. Immunoassay tests generally include an absorbent, fibrous strip having glucose-binding molecules incorporated at specific zones on the strip. The EBC sample is deposited on the strip and by capillary action the sample will migrate along the strip and contact the glucose-binding molecules. Where glucose is present, at least one glucose-binding molecule manifests a detectable response, for example a color change. Patents that describe immunoassay technology include the following: U.S. Pat. Nos. 5,262,333 and 5,573,955.

In another embodiment, the device of the present invention may be designed so that subjects can exhale via the mouth or nose directly onto a sensor of the invention, without needing a breath sampling apparatus. For example, a mouthpiece or nosepiece will be provided for interfacing a subject with the device to readily transmit the exhaled breath to the sensor (See, i.e., U.S. Pat. No. 5,042,501). In another embodiment, a subject's EBC sample can be captured in a container (vessel) for later analysis using a sensor of the subject invention (i.e., mass spectrometer).

The results from the sensor technology analysis of the EBC samples are optionally provided to the user (or subject) via a reporting means. In one embodiment, the sensor technology includes the reporting means. Contemplated reporting means include a computer processor 112 linked to the sensor technology in which electronic or printed results can be provided. Alternatively, the reporting means can include a digital display panel, transportable read/write magnetic media such as computer disks and tapes which can be transported to and read on another machine, and printers such as thermal, laser or ink-jet printers for the production of a printed report.

The reporting means can provide the results to the user (or subject) via facsimile, electronic mail, mail or courier service, or any other means of safely and securely sending the report to the subject. Interactive reporting means are also contemplated by the present invention, such as an interactive voice response system, interactive computer-based reporting system, interactive telephone touch-tone system, or other similar system. The report provided to the user (or subject) may take many forms, including a summary of analyses performed over a particular period of time or detailed information regarding a particular bodily fluid sample analysis. Results may also be used to populate a financial database for billing the subject, or for populating a laboratory database or a statistical database.

According to the subject invention, the sensor can include a computer that communicates therewith, which can also notify the medical staff and/or the subject as to any irregularities in glucose level, dosing of pharmaceuticals used to modulate glucose levels, dangerous drug interactions, and the like. This system will enable determination as to whether a subject has been administered a pharmacologically effective amount of a therapeutic drug to modulate glucose levels. The device could also alert the subject (or user) as to time intervals and/or dosage of therapeutic drug to be administered. Accordingly, it is contemplated herein that a sensor of the subject invention can be portable.

Preferably, in operation, the sensor will be used to identify a baseline spectrum for the subject's glucose level prior to drug administration, if necessary. This will prove beneficial for the monitoring the efficacy of the drug in maintaining proper glucose levels in a subject.

Remote Communication System

A further embodiment of the invention includes a communications device in the home (or other remote location) that will be interfaced to the sensor. The home communications device will be able to transmit immediately or at prescribed intervals directly or over a standard telephone line (or other communication transmittal means) the data collected by the data monitor/analyzer device. The communication of the data will allow the user (i.e., physician) to be able to remotely verify if the appropriate dosage of a therapeutic drug is being administered to the subject. The data transmitted from the home can also be downloaded to a computer where the drug blood levels are stored in a database, and any deviations outside of pharmacological efficacy would be automatically flagged (i.e., alarm) so that a user (i.e., subject, physician, nurse) could appropriately adjust the drug dosage per suggestions provided by a computer processing unit connected to the sensor or per dosage suggestions provided by health care personnel (i.e., physician).

Correlation of Glucose in Exhaled Breath to Glucose in Blood

According to the subject invention, the ratio of exhaled breath to blood glucose concentration is a large ratio (e.g., 3-5 orders of magnitude lower in breath than in blood) and that this ratio is predictable and reproducible once determined for a particular individual. By analyzing glucose present in EBC, a more predictive, non-invasive, and simpler method is provided to monitor glucose concentration in a subject by monitoring breath rather than blood.

According to the subject invention, once the level of EBC glucose is measured, it is given a numerical value that corresponds to the blood glucose concentration in the subject (usually expressed in mg/dL). Should the concentration fall below that value, the new value would be indicative of a decrease in concentration. Should the concentration increase beyond that value, the new value would be indicative of an increase in glucose concentration. This numerical scale would allow for easier monitoring of changes in concentration. The numerical scale would also allow for easier translation into control signals for alarms (such as indication that the person is hypoglycemic, etc.), outputs, or charting. The upper and lower limits could be set to indicate thresholds such as from normal to dangerous glucose levels.

In one embodiment of the subject invention, the concentration of glucose in a sample of EBC is reproducibly measured when a constant sample size of exhaled breath and constant dilution of exhaled breath sample are taken. Sample size can be controlled by several methods, which will be elucidated in more detail below. The dilution factor is preferably controlled since changes in glucose concentration in EBC may be due to changes in blood glucose or due to varying dilution of the sample based on the amount of water in the collected EBC.

The dilution of various solutes found in EBC has been studied. A number of candidate analytes and/or physical properties of the EBC could be used to determine whether a target dilution or concentration of the sample has occurred. As long as a reliable, standard marker is presented, then EBC glucose concentration can be corrected for any dilution or concentration.

According to the subject invention, a number of analytes and properties of EBC can be studied including, but not limited to: $Na^+$, $K^+$, $Cl^-$, viscosity, conductivity, surface tension, osmolality, SGOT, SGPT, and sialic acid. Effros and colleagues (Effros, et. al., "Dilution of Respiratory Solutes in Exhaled Condensates," *Am J Respir Crit Care Med,* 165:663-339, (2002), incorporated herein by reference in its entirety) have studied the dilution of a wide range of "solutes" present in EBC. According to Effros, most exhaled water is produced as gaseous water vapor and that the presence of non-volatile solutes in EBC suggests that droplets of respiratory fluid (RF) are also collected (and significantly diluted). Using 20 normal subjects, the conductivity of EBC was found to be 497+/−68 uM. $Na^+$ concentration averaged 242+/−43 uM. The variations in $Na^+$ concentration correlated with those of $K^+$ and $Cl^-$ and were attributed to difference in respiratory droplet dilution.

Dividing the sum of the EBC $Na^+$ and $K^+$ by the sum of the plasma concentrations indicates that RF represents between 0.01% and 2.00% of the condensate volume. Thus, the calculated concentration of $Na^+$ in RF was 91+/−8 mM, $K^+$ 60+/−11 mM and $Cl^-$ 102+/−17 mM respectively. Assuming that the plasma concentration of the sum of $Na^+$ and $K^+$ are 144 mM, the dilution of respiratory droplets by water vapor in EBC can be calculated using the following formula:

$$D = \frac{[Na^+] \text{ plasma} + [K^+] \text{ plasma}}{[Na^+] \text{ condensate} + [K^+] \text{ condensate}}$$

Thus, by measuring these electrolytes, or alternatively other electrolytes such as $Cl^-$, it is possible to compensate for varying dilution of the RF glucose under a variety of conditions. When this dilution factor is determined precisely, then EBC glucose can be correlated precisely with blood glucose!

Likewise, Cope et. al. (Cope, et. al., "Effects of ventilation on the collection of exhaled breath in humans." *J Appl Physiol,* 96:1371-1379 (2004), incorporated herein by reference in its entirety) have shown that ventilation can affect the concentration of compounds detected in exhaled breath (gas). However, they further showed that when patients breath at a normal rate and tidal volume (as opposed to hyper- or hypoventilation) the concentrations can be reliably measured. End-tidal $CO_2$, pressure, temperature and/or flow tracings can be used to "coach" patients to breathe reproducibly with a simple display.

According to the subject invention, where the effects of dilution of RF droplets is corrected for and the patient is "coached" to deliver a reproducible breath sample, EBC glucose is reliably collected and correlated with blood glucose.

Applications of Frequent Glucose Monitoring

One aspect of the present invention comprises a system and method for monitoring an effect of at least one non-insulin-containing and/or one insulin-containing pharmaceutical composition on glucose levels in a subject receiving the pharmaceutical composition. In the method, glucose monitoring in the subject may be carried out by: administering a prescribed pharmaceutical composition that affects glucose levels in a subject; obtaining a sample of the subject's exhaled breath; extracting condensates from the sample of exhaled breath; and assessing glucose amounts or concentrations in the condensates extracted from the subject's exhaled breath. In a related embodiment, a record is maintained of the treatments with the pharmaceutical composition as well as of corresponding glucose amounts or concentrations determined present in EBC after (and in certain instances before) each treatment. The records are compared to evaluate the effect of the pharmaceutical composition on glucose levels in the subject receiving the pharmaceutical composition.

A reference range of glucose amounts or concentrations is typically determined that corresponds to maintaining a desired range of glucose amounts or concentrations in the subject during a treatment course with the pharmaceutical composition. The reference range comprises, for example, a high threshold glucose value, a low threshold glucose value, a predetermined rate of change (e.g., glucose levels change at a rate faster than a predetermined rate of change), and/or a predicted glucose value for a later time point. The glucose monitoring device may provide an alert corresponding to threshold values, rate changes, a predicted glucose value that falls outside of the predetermined range, etc. Such glucose monitoring is useful when any one or more of a number of pharmaceutical compositions are being used to treat a subject. Exemplary pharmaceutical compositions are described herein and include, but are not limited to, pentamidine, quinine, saquinavir, and/or indomethacin. In addition, the subject may also be receiving insulin, or another pharmaceutical directly targeted to maintenance of glucose levels in the subject.

In a related embodiment of the present invention, monitoring of glucose amount or concentration in the subject is accomplished by monitoring glucose in EBC using the systems and methods described herein. Extraction is carried out, for example, frequently over a selected period of time. The collection reservoir is analyzed, at least periodically and typically frequently, to measure glucose concentration therein. The measured value correlates with the subject's blood glucose level.

The glucose condensate monitoring device used in the present invention may have alert means, where an alert is provided to the subject (for example, an auditory alert) when glucose levels exceed the predetermined threshold values, when glucose levels change at a rate faster than a predetermined rate of change, or when a predicted glucose value for a later time point falls outside of the predetermined range.

Many disease states and conditions will benefit from frequent monitoring of glucose and, optionally, one or more additional analytes. Non-limiting examples of such disease states and conditions that will benefit from frequent monitoring of glucose levels, include hyperglycemia; hypoglycemia; cystic fibrosis; AIDS; organic and amino acid disorders; cancer remission; as well as subjects with cardiovascular disease; stroke subjects; gestational diabetes; organ transplant recipients; those infected with *Candida*, HIV or malaria; elderly subjects; kidney subjects; young children; long-distance drivers; intense exercisers; subjects on a weight loss program or other special diet; subjects receiving growth hormone; and alcoholics. Furthermore, monitoring of glucose levels will also be beneficial in determining the effects of one or more pharmaceutical compositions on glucose levels or concentrations in a biological subject. In the present invention, at least one of the pharmaceutical compositions whose effect on glucose levels is monitored does not contain insulin.

I. Hyperglycemia

Hyperglycemia refers to excessive levels of blood glucose in a subject. The primary form of hyperglycemia is diabetes mellitus (DM), which is hyperglycemia secondary to decreased insulin where either production of insulin is decreased or peripheral tissue resistance to insulin is increased. Insulin-dependent DM (IDDM, or Type I DM) accounts for about 10% of DM cases and usually occurs in childhood or early adulthood. Type I DM can result in ketoacidosis when subjects are without insulin therapy. Non-insulin dependent DM (NIDDM, or Type II DM) usually occurs in people>40 years of age, and about 60% of the subjects are obese. Type II DM can also occur in animals, for example, domestic cats. These subjects are not prone to ketosis but may develop it under conditions of stress. Gestational onset DM (GODM) occurs when diabetes onset is during pregnancy and resolves with delivery. These subjects are at a higher risk for developing DM at a later date. Secondary DM can be caused, for example, by steroid therapy, Cushing's syndrome, pancreatectomy, pancreatic insufficiency secondary to pancreatitis, or endocrine disorders. The Diabetes Control and Complications Trial Group reported that the long-term complications of DM appear to be directly related to control of blood glucose levels. Thus, the conclusion of the study was that intensive therapy delays the onset and slows the progression of diabetic retinopathy, nephropathy, and neuropathy in subjects with IDDM. Other studies have shown the same conclusions in NIDDM. Thus, frequent monitoring of blood glucose levels is an important tool for both diagnosing and determining appropriate therapy for many conditions associated with abnormal glucose levels.

II. Dysglycemia and Cardiovascular Disease

Recent research has found a connection between dysglycemia, or abnormal glucose levels, and risk factors (e.g., atherosclerosis and hypertension) for cardiovascular disease (see, for example, Gerstein H C, Yusuf S (1996) *Lancet* 347 (9006): 949-950; Gerstein H C, Yusuf S (1998) *Diabetes Research and Clinical Practice* 40 Suppl: S9-S14; Meigs J B, Nathan D M et al. (1998) *Ann Intern Med* 128(7): 524-533; Tsai S T, Li C L et al. (2000) *J Clin Epidemiol.* 53(5): 505-510, all of which are incorporated herein by reference in their entirety). For instance, atherosclerotic changes appear to develop in non-diabetic individuals with impaired glucose tolerance (see, e.g., Kawamori, R (1998) *Diabetes Res Clin Pract* 40 Suppl: S35-S42; Yamasaki Y, Kawamori R et al. (1995) *Diabetologia* 38(5):585-591). Similarly, hypertension is also associated with impaired glucose tolerance (Vaccaro et al. (1996) *Diabetologia* 39:70-76, all of which are incorporated by herein by reference in their entirety).

At a molecular level, studies have shown a connection between a deletion polymorphism in the antigotensis-converting enzyme (ACE) gene (which is related to cardiovascular disease) and elevated plasma glucose levels after oral glucose load (Ohishi et al. (2000) *Clin Exp Pharmacol Physiol* 27:483-487, which is incorporated herein by reference in its entirety). Further, high blood glucose concentration (in both diabetic and non-diabetic subjects) increases the risk of death and poor outcome after acute myocardial infarction and significantly increases the mortality rate from cardiovascular disease (see, e.g., Capes et al. *Lancet* (2000) 355(9206):773-778; Feskens E J & Kromhout D (1992) *J Clin Epidemiol* 45(11): 1327-34 and Bjornholt et al. (1999) *Diabetes Care* 22(1): 4549, all of which are incorporated herein by reference in their entirety).

The risk of heart disease associated with hyperglycemia increases continuously across the spectrum of glucose tolerance categories, from those that are just barely above normal to those in the diabetic range. Generally speaking, as blood glucose levels increase, so does the likelihood that an individual will experience cardiovascular disease. (see, e.g., Temelkova-Kurktschiev et al. (2000) *Exp Clin Endocrinol Diabetes* 108:93-99, which is incorporated herein by reference in its entirety). This relationship is similar to the relationship between smoking and blood pressure to cardiovascular risk.

Thus, monitoring and controlling blood glucose levels in individuals with a family or personal history of heart disease allows these subjects to reduce the risk of cardiovascular problems. Further, in certain embodiments, it will also be useful to monitor levels of glucose, cholesterol, triglycerides and/or therapeutic drugs used to treat high cholesterol, hypertension or the like.

III. Glucose Tolerance, Diabetes Onset and Cystic Fibrosis

It is estimated that approximately 50,000 individuals in the U.S. and Canada suffer from cystic fibrosis. One well-known complication of this disease is cystic fibrosis-related diabetes (CFRD) (Finkelstein S M & Wielinski C L (1988) *J Pediatr* 112(3): 373-377; Handwerger S, Roth J et al. (1969) *N Engl*

*J Med* 281(9): 451-461, both of which are incorporated herein by reference in their entirety). CFRD appears to be grossly underestimated in the U.S., probably due to the lack of routine oral glucose tolerance tests (see, e.g., Hardin D S & Moran A (1999) *Endocrinol Metab Clin North Am.* 28(4): 787-800, which is incorporated herein by reference in its entirety). CFRD incidence has also increased as the life-spans of cystic fibrosis subjects increase. In a 10 year study of CFRD, Cucinotta D, De Luca Fetal. ((1999) *Acta Paediatr* 88(4): 389-393, which is incorporated herein by reference in its entirety) found that impaired glucose tolerance was the sole predictor of whether subjects will develop CFRD.

Thus, frequent monitoring of blood glucose levels in cystic fibrosis subjects will allow clinicians to detect diabetes earlier than was previously possible. Moreover, monitoring of trends in blood glucose levels can help identify groups who are prone to develop diabetes. In addition to monitoring glucose, the levels of chloride, sodium, and/or therapeutic drugs used to treat CF may also be monitored.

IV. Abnormal Blood Glucose Levels in Stroke, Ischemia, Brain Injury, Head Injury, and Spinal Cord Injury Hyperglycemia following acute stroke is strongly associated with subsequent mortality, impaired neurological recovery and brain lesions in diabetic and non-diabetic subjects (Sala et al. (1999) *Ann NY Acad Sci* 890:133-154; Weir C J, Murray G D et al. (1997) *BMJ* 314(7090): 1303-1306; Gray C S, Taylor R et al. (1987) *Diabet Med* 4(3): 237-40; Guyot et al. (2000) *Horm Metab Res.* 32:6-9; Hayahi (2000) *No To Hattatsu* 32:122-131; Rovlias and Kotsou (2000) *Neurosurgery* 46:335-342, all of which are incorporated herein by reference in their entirety). Furthermore, between 20% and 50% of acute stroke subjects are hyperglycemic at presentation. As a result, it is of increasing interest to study the effects of modulating blood glucose levels in stroke subjects, for example by administering glucose potassium insulin (GKI) to these subjects (Scott J F, Robinson G M et al. (1999) *Stroke* 30(4): 793-799; Scott J F, Gray C S et al. (1998) *QJ Med* 91(7): 511-515; Hennes et al. (1999) *Anaesthesist* 48:858-870; Schurr et al. (1999) *Ann NY Acad Sci* 893:386-390, all of which are incorporated herein by reference in their entirety).

Thus, frequent monitoring blood glucose levels in stroke subjects can allow clinicians to detect abnormal glucose levels at an early time and early treatment may reduce mortality and improve neurological outcomes.

V. Hyperglycemia Associated with Organ Transplantation

Impaired glucose tolerance or DM are also frequent complications after organ transplantation, in both human leukocyte antigen (HLA) matched and mismatched subjects. For example, liver transplant recipients have been shown to have severe post-prandial hyperglycemia, which may be attributed to insulinpoenia and a late increased glucose turnover (Schneiter et al. (2000) *Diabetes Metab* 26:51-56; Petruzzo et al. (2000) *Diabetes Metab* 26:215-218, all of which are incorporated herein by reference in their entirety). Similarly, in the context of grafts, Trick et al. ((2000) *J Thorac Cardiovasc Surg* 119:108-114, which is incorporated herein by reference in its entirety) report that appropriate control of preoperative blood glucose levels appears to help prevent deep sternal site infection after coronary artery bypass graft operations. Accordingly, frequent monitoring of blood glucose levels before and after transplant (e.g., organ transplant and grafts) is part of the present invention. Furthermore, multiple analytes in these subjects (e.g., glucose, an immunosuppressive drug, etc.) can also be measured.

VI. Hyperglycemia Associated with *Candida* Infection

Chronic or repeated infection with *Candida* (e.g., vulvovaginal candidiasis and congenital cutaneous candidiaseis in infants) is a widespread problem in both immunocompetent and immunosuppressed subjects. A known etiology of recurrent candidiasis is hyperglycemia, see, e.g., Ringdahl (2000) *Am Fam Physician* 61:3306-3312, which is incorporated herein by reference in its entirety. Further, because many subjects experience recurrent *Candida* infections once prophylaxis is discontinued, long-term therapy may still be warranted. Therefore, frequent monitoring of blood glucose level is useful in subjects suffering from chronic or repeated infection with *Candida*.

VII. Diet-Induced Hyperglycemia

Diet can also induce hyperglycemia in certain subjects. Diets high in carbohydrates and/or fat have been associated with development of insulin resistance and perturbed carbohydrate and lipid metabolism and leptin has been proposed as a treatment for diet induced hyperglycemia and insulin resistance (Buettner et al. (2000) *Am J Physiol Endocrinol Metab* 278:E563-9, which is incorporated herein by reference in its entirety). Thus, in addition to allowing a subject to quickly and easily monitor blood glucose levels, the present invention allows for the monitoring of additional analytes, for example, leptin.

VIII. HIV-Related Hyperglycemia

The present invention will also find use in evaluating and determining treatment regimes for human immunodeficiency virus (HIV)-infected subjects, particularly those subjects currently receiving protease inhibitors. Although protease inhibitors have proven to be very useful in treating HIV infection in certain subjects, these drugs often exhibit glucose-related side effects, including, for example, hyperglycemia, new-onset diabetes mellitus, lipodystrophic syndrome, central obesity, peripheral fat loss, and hyperlipidemia, Scevola et al. (2000) *AIDS Read* 10:365-369; 371-375; Mathe (1999) *Biomed Pharmacother* 53:449-451, which is incorporated herein by reference in its entirety. Accordingly, all subjects receiving protease inhibitors should be monitored for blood glucose levels.

IX. Geriatric Hyperglycemia

The prevalence of hyperglycemia in elderly persons (e.g, greater than 60 years of age) is high and is significantly associated with cardiovascular risk factors such as obesity, high systolic pressure and hypertriglyceridemia, see, above and Lai et al. (2000) *J Gerontol A Biol Sci Med* 55:M255-256. Hyperglycemia is also more common elderly trauma subjects and in those elderly subjects exhibit hostility, Frankenfield et al. (2000) *J Trauma* 48:49-56, all of which are incorporated herein by reference in their entirety. Thus, is useful to monitor glucose levels in these in elderly subjects.

X. Hyperglycemia in Neonates and Children

Transient hyperglycemia that occurs as a part of the stress response in acute illnesses can cause serious complications in infancy and childhood, Gupta et al (1997) *Indian J Pediatr* 64:205-210, which is incorporated herein by reference in its entirety. For example, non-ketotic hyperglycemia (NKH) in infancy and childhood can cause serious complications, for example, hydrocephalus requiring shunting and subsequent brain damage, Van Hove et al. (2000) *Neurol* 54:754-756, which is incorporated herein by reference in its entirety. Thus, frequent monitoring of glucose (and, optionally, other analytes, such as ketones) is useful in young children.

Further, there are numerous reports of transient neonatal diabetes (Menon, P. S., et al., *Indian J Pediatr* 67(6):443-448, 2000; Shield, J. P., *Horm Res* 53(Suppl. 1):7-11, 2000; Stanley, C. A., *Pediatr Clin North Am* 44(2):363-374, 1997; Wilson, S., *Nurs Times* 87(36):44-45, 1991, which are incorporated herein by reference in their entirety). There are numerous causes that are thought to contribute to such transient neonatal diabetes, including, but not limited to, chromosomal abnormality, genotypic effects, and/or imprinting (Varrault, A., et al., *J Biol Chem* 276(22)18653-18656, 2001; Marquis, E., et al, *Tissue Antigens* 56(3):217-222, 2000; Gardner, R. J., et al, *Hum Mol Genet* 9(4):589-596, 2000; Kamiya, M., et al., *Hum Mol Genet* 9(3):453-460, 2000; Shield, J. P., et al., *Arch Dis Child Fetal Neonatal Ed* 76(1): F39-42, 1997, which are incorporated herein by reference in their entirety), treatments (e.g., drug treatments to mother and/or neonate) (Moniaci, V. K., et al, *J Perinat Neonatal Nurs* 11(4):60-64, 1998; Uhrig, J. D., et al, *Can Med Assoc J* 128(4):368-371, 1983; Bomba-Opon, D. A., et al, *Ginekol Pol* 71(8):887-892, 2000; Yunis, K. A., et al., *Am J Perinatol* 16(1): 17-21, 1999, which are incorporated herein by reference in their entirety), nutrition (Barker, D. J., *Nutrition* 13(9):807-813, 1997, which is incorporated herein by reference in its entirety), and disease states (e.g., in the mother and/or neonate) (Ahlfors, K., et al, *Scand J Infect Dis.* 31(5): 443-457, 1999; Lorenzi, P., et al., *AIDS*, Dec. 24, 12(18): F241-247, 1998; Cooper, L. Z., *Rev Infect Dis* 7(Suppl. 1):S2-10, 1985, which are incorporated herein by reference in their entirety). In addition, babies born before term may have glucose metabolism abnormalities (Gross, T. L., et al., *Am J Obstet Gynecol* 146(3):236-241, 1983; Lackman, F., *Am J Obstet Gynecol* 184(5):946-953, 2001, which are incorporated herein by reference in their entirety).

Thus, frequent monitoring of glucose (and, optionally, other analytes, such as drug levels) is useful in neonates and premature neonates to reduce possible short- and/or long-term damage caused by low, high, or fluctuating glucose levels, as well as to increase probability of survival.

XI. Hyperglycemia Associated with Intense Exercise

During intense exercise, fluctuations in the levels of various analytes, for example glucose, hormones, etc., has been shown to occur, Kreisman et al. (2000) *Am J Physiol Endocrinol Metab* 278:E7860793, which is incorporated herein by reference in its entirety. Commonly, subjects who exercise intensely can become hyperglycemic. Marliss et al. (2000) *J Appl Physiol* 88:457-66, which is incorporated herein by reference in its entirety. Accordingly, monitoring the level of glucose and/or other analytes such as hormones aids in regulating exercise intensity and/or intake of food or fluids during exercise.

XII. Hypoglycemia

Hypoglycemia refers to decreased levels of glucose in plasma, or below normal levels. Although hypoglycemic subjects may be asymptomatic, many exhibit adrenergic stimulation symptoms including diaphoresis, anxiety, irritability, palpitations, tremor, and hunger. Hypoglycemic events may also occur during the night-time (nocturnal hypoglycemia), for example, when a person is sleeping, thus vulnerable to continuing decreases in levels of glucose in plasma. Severe hypoglycemia may cause confusion, visual blurring, loss of consciousness and seizures. Typically, hypoglycemia occurs about 2 to 4 hours postprandially and generally subsides in 15 to 20 minutes. The etiology of hypoglycemia is often idiopathic, but may be caused by early diabetes, malignancies of the pancreas, benign tumors of the pancreas, general hypertrophy of the pancreas without evident disease, alcohol intake and liver disease (decreased gluconeogenesis), gastrectomy, renal failure, drugs such as salicylates, beta-blockers, pentamidine, acetylcholine esterase (ACE) inhibitors, excess insulin including insulinoma, self-administered insulin or oral hypoglycemic agents; pituitary or adrenal insufficiency.

Clinicians are generally most concerned with functional or idiopathic hyperinsulinism, the most common type of which is caused by excessive intake of refined sugars, caffeine, emotional stress or a combination of these factors with sugar and caffeine compounded in their effects through a condition of stress. The Islets of Langerhans (insulin producing cells) in the pancreas are over-stimulated by constant bombardment of refined sugar and caffeine producing greater amounts of insulin than required to metabolize the circulating blood sugar, thus keeping blood sugar levels lower than normal except for a very short time after ingestion of food. Eventually any sugar, good, bad, or indifferent, will trigger the pancreas to secrete excessive amounts of insulin. The liver is also heavily involved in this mechanism as it controls reconversion of stored glycogen into glucose for distribution in the blood stream. In addition, all the endocrine glands are linked in a dynamic balance to compensate for any deviation of blood sugar levels so that the brain and nervous system are never for an instant deprived of necessary amounts of blood sugar needed for their normal activity. This balance is upset by stress and symptoms such as anxiety, irritability, fear, sweating, flushing or pallor, numbness, chills, headaches, dizziness, weakness and faintness are common. However, the most obvious symptoms are excessive hunger just about all the time and great fatigue and weakness. Thus, hypoglycemia is an important medical issue and frequent monitoring of glucose levels is useful to a wide variety of subjects.

XIII. Hypoglycemia and Eating Disorders

Hypoglycemia can occur in individuals with anorexia nervosa (Alvin et al. (1993) *Arch Fr Pediatr* 50(9): 755-762; Johnson et al. (1994) *Int J Eat Disord* 15(4): 331-341; Overduin J & Jansen A (1997) *Physiol Behav* 61(4): 569-575, which are incorporated herein by reference in their entirety). In bulimic subjects following purging of a meal, there is a dramatic reduction in insulin and glucose (Johnson et al., above). Because of the correlation between hypoglycemia and hunger, the hypoglycemia that results from purging may be partially responsible for continued binging and purging. Thus, monitoring blood glucose levels in subjects with eating disorders can assist therapists in treating them, and can also help subjects understand physiological processes that contribute to their problems.

XIV. Hypoglycemia and Pentamidine Therapy

Pentamidine is an effective agent for treating *Pneumocystis carinii pneumonia* pneumonia in HIV-infected subjects, the hemolymphatic stage of Gambian trypanosomiasis, and antimony-resistant leishmaniasis. Iatrogenic hypoglycemia occurs in one-quarter to one-third of HIV-infected subjects treated with this drug, and it can become severe and even life-threatening, Andersen et al. (1986) *Drug Intell Clin Pharm* 20(11): 862-868; Stahl-Bayliss et al. (1986) *Clin Pharmacol Ther* 39(3): 271-5; Chan et al. (1996) *Drug Saf* 15(2): 135-157, which are incorporated herein by reference in their entirety. Thus, frequent monitoring of the levels of blood glucose and, optionally, other analytes (e.g., pentadiene), in HIV-infected subjects receiving pentamidine therapy will reduce the risk of nosocomial infections in them, and will reduce the risk of HIV transmission to needle-stick performing hospital personnel.

XV. Hypoglycemia and Disease States

Many organic and amino acid disorders are also correlated with hypoglycemia, for example acidemias that involve the oxidation of fatty acids (Ozand et al. (2000) *Semin Perinatol* 24:172-193, which is incorporated herein by reference in its entirety); Beckwith-Wiedemann syndrome (DeBaun et al. (2000) *Semin Perinatol* 24:164-171, which is incorporated herein by reference in its entirety); glycogen storage diseases (Wolfsdorf et al. (1999) *Endocrinol Metab Clin North Am* 28:801-823, which is incorporated herein by reference in its entirety); carbohydrate-deficient glycoprotein syndrome (Babovic-Vuksanovic et al. (1999) *J Pediatr* 135:775-781, which is incorporated herein by reference in its entirety); hypopituitarism (Nanao et al. (1999) *Acta Paediatr* 88:1173, which is incorporated herein by reference in its entirety); and mitochondrial respiratory chain disorders (Morris (1999) *Liver* 19:357-368, which is incorporated herein by reference in its entirety).

Glycogen storage diseases (glycogenoses) are a group of hereditary disorders that result from a lack of at least one enzyme involved in glycogen synthesis or breakdown. The result is accumulation of glycogen in tissues. According to the Merck Manual (16$^{th}$ edition), hypoglycemia can be a severe problem in some of these glycogen storage diseases, for example, Type 0 (enzyme system affected, glycogen synthetase), Type Ia (enzyme system affected, glucose-6-phosphatase), Type Ib (enzyme system affected, glucose-6-phosphatase translocase), Type III (enzyme system affected, debrancher enzyme system), Type VI (enzyme system affected, liver phosphorylase). Subjects with glycogen storage disorders must follow strict diets (in order to avoid hypoglycemia and other problems) and must monitor their blood glucose levels (see, Wolfsdorf, et al., above).

Thus, frequent monitoring of glucose levels non-invasively in these subjects will likely improve their clinical outcomes and simplify their lives significantly.

XVI. Hypoglycemia and Alcoholism

Hypoglycemia is a common adverse effect of alcoholism, and it occurs in up to 95% of alcoholics, Bunout (1999) *Nutrition* 15(7-8): 583-589, which is incorporated herein by reference in its entirety. Hypoglycemia due to excessive alcohol ingestion can be severe, and alcoholics are usually glucose intolerant as well, Kearney et al. (2000) *J R Soc Med* 93:15-17, which is incorporated herein by reference in its entirety. This condition is most likely due to an inhibition of glucose-stimulated insulin secretion. Frequent, non-invasive monitoring of blood glucose levels and/or other analytes such as alcohol can treat alcoholics by allowing them to see clinical improvements in their blood sugar levels, or to allow them to see the extent to which alcohol abuse has damaged an important metabolic process.

XVII. Hypoglycemia and Long Distance Driving Performance

Long distance drivers often experience hypoglycemia. Further, the fatigue associated with hypoglycemia and the resulting possibility that these drivers may fall asleep at the wheel is a potential hazard, Frier (2000) *Diabetes Care* 23:148-150; Marrero et al. (2000) *Diabetes Care* 23:146-147, which are incorporated herein by reference in their entirety. Long distance driving and associated risks are most frequently associated with long-haul trucker drivers (*N Engl J. Med.* 1997 Sep. 11;337(11):755-761, which is incorporated herein by reference in its entirety). Long distance driving is, for example, sustained driving with little or no rest for 5 to 10 hours or more. Typical "long-haul" trucker drivers may drive from 10 to 15 hours at a time. The California Department of Motor Vehicles suggests a ten minute rest after even just two hours of driving. Frequent monitoring of glucose levels will allow long distance drivers to more adequately determine food and/or fluid intake. This in turn will decrease the risks posed by poor driving performance caused by hypoglycemia.

XVIII. Hypoglycemia and Renal Failure

Hypoglycemia and its accompanying complications occur frequently in both diabetic and non-diabetic end stage renal failure (ESRF) subjects, Haviv et al. (2000) *Ren Fail* 22:219-223, which is incorporated herein by reference in its entirety. Accordingly, using the methods described herein, ESRF subjects can benefit from frequent, periodic monitoring of glucose and/or other analyte levels (e.g., glucose and liver enzymes).

XIX. Hypoglycemia, Neonates, and Children

Hypoglycemia can cause severe problems in infants or children, including for example mild to severe brain damage (Kinnala et al. (2000) *Semin Perinatol* 24:116-119; Frey et al. (2000) *Scweiz Zmed Wochenschr* 130:151-155; Hawdon (1999) *Eur J Pediatr* 158 Suppl 1:S9-S12, which are incorporated herein by reference in their entirety). Because hypoglycemia can occur if feeding is postponed more than 12 to 24 hours post-partum, there remains a need for frequent and close clinical observation of neonates and other vulnerable children while avoiding excessively invasive management that may interfere with feeding. Thus, the present invention provides frequent monitoring of glucose levels and, optionally, the levels of other analytes which may signal neonatal distress, such as ketones.

XX. Hypoglycemia and Growth Hormone Therapy

Growth hormone (GH) therapy has been recommended for short stature children and for hypoglycemias due to growth hormone deficiency. Increasingly, growth hormone therapy is also recommended for adults with growth hormone deficiency following pituitary tumor surgery or irradiation (Dash, et al., J. *Assoc Physicians India* 47:417-425, 1999, which is incorporated herein by reference in its entirety). Further, the insulin tolerance test (ITT) is widely accepted as the method of choice to evaluate growth hormone secretion capacity in adults with hypothalamic-pituitary disorders, Hoeck, et al. (2000) *J Clin Endocrinol Metab* 85:1467-1472, which is incorporated herein by reference in its entirety. Thus, the present invention can be used in both adults and children to monitor the levels of glucose and, in certain instances, various analytes (e.g., growth hormone).

XXI. Hypoglycemia and Cancer Remission

Under most circumstances, tumors growth rapidly when the blood glucose supply is high and grow slowly when blood glucose supply is low. In cases of spontaneous remissions, tumors appear to grow rapidly and steadily despite low blood glucose and, consequently, the tumor system collapses and is removed by the immune system. It has been suggested that remission may be induced if hypoglycemia is initiated just prior to reducing the tumor mass and then maintaining the hypoglycemic state, Niakan (1999) *Cancer Biother Radiopharm* 14:297-298, which is incorporated herein by reference in its entirety. In such regimes, the present invention can be used to monitor blood glucose levels to help the subject remain hypoglycemic during the critical period.

XXII. Hypoglycemia and Malaria

Severe malaria often presents with hypoglycemia, Agbenyega et al. (2000) *J Clin Endorcrinol Metab* 85:1569-1576, which is incorporated herein by reference in its entirety. Furthermore, because hypoglycemia is a frequent complication of quinine therapy for malaria, frequent blood sugar estimations are required in treating malaria or quinine toxicity, Padmaja et al. (1999) *Indian J Med Sci* 53:153-157, which is incorporated herein by reference in its entirety. Thus, the ability to monitor glucose and/or quinine levels is useful in relation to diagnosis and treatment of malaria.

XXIII. Drug Treatment Related Hypoglycemia

As noted above, hypoglycemia is present in many diseases. One cause of hypoglycemia appears to be related to drug therapy, Virally et al. (1999) *Diabetes Metab* 25:477-490, which is incorporated herein by reference in its entirety. For instance, saquinavir, a treatment for HIV, induces hypoglycemia in Type II diabetes (see, Zimhony and Stein (1999) *Ann Intern Med* 131:980, which is incorporated herein by reference in its entirety), while indomethacin, a drug used to arteriosus in premature infants, also induces hypoglycemia. Consequently, frequent monitoring of glucose and, in certain instances, other analytes (e.g., the therapeutic drug) in these individuals is part of the present invention.

XXIV. Hypoglycemia, Brain Injury and Stroke

As noted above, brain injury can be a serious complication of hypoglycemia. de Courten-Meyers et al. (2000) *J Cereb Blood Flow Metab* 20:82-92; Losek (2000) *Ann Emerg Med* 35:4346, which are incorporated herein by reference in their entirety. There is also strong evidence that severe hypoglycemia can worsen the prognosis in acute stroke. Nagi et al. (1999) *Nervenarzt* 70:944-949, which is incorporated herein by reference in its entirety. To determine appropriate treatment options, routine and rapid assessment of glucose is recommended.

XXV. Hypoglycemia and Endurance Exercise and Training

Performance in endurance events requires an adequate supply of nutrients such as glucose. Thus, performance is optimized when training includes monitoring of glucose (and other analyte levels in certain instances) combined with nutritional supplementation to prevent hypoglycemia, Coyle (1999) *J Sci Med Sport* 2:181-189, which is incorporated herein by reference in its entirety.

XXVI. Severe Hypoglycemia

Some individuals may experience recurrent bouts of severe hypoglycemia. Because such episodes of hypoglycemia may cause severe complications, it is recommended that individuals with a recent history of severe hypoglycemia better recognize the occurrence of low blood glucose. Cox et al. (1999) *Diabetes Care* 22:2018-2025, which is incorporated herein by reference in its entirety. The present invention provides a fast and efficient way for these individuals to monitor glucose levels.

XXVII. Pregnancy and Gestational Diabetes

Dysglycemia during pregnancy can cause severe problems for both mother and fetus, see, e.g., Schafer-Graft et al. (1999) *Ther Umsch* 56:572-576, which is incorporated herein by reference in its entirety. For diabetic mothers who become pregnant, close monitoring and tight control of blood glucose levels during the first 9 weeks of pregnancy helps reduce the incidence of birth defects, Schwartz et al. (2000) *Semin Perinatol* 24:120-135, which is incorporated herein by reference in its entirety.

In approximately 4% of women, pregnancy will induce "gestational diabetes" or "insulin resistance" in women who have never had diabetes before but who have high blood sugar levels during pregnancy. Without enough insulin, the mother become hyperglycemic and is more likely to become hypertensive, Bartha et al. (2000) *Am J Obstet Gynecol* 182:346-350, which is incorporated herein by reference in its entirety. In addition to the problems this causes the mother, hyperglycemia and hypertension also place the fetus at risk for serious complications. The high maternal levels of glucose are able to cross the placenta, which causes the fetus's pancreas to make extra insulin to metabolize the blood sugar and can lead to macrosomia (alternately called a "fat" baby, or a "big bad baby" (BBB)). Babies with macrosomia face health problems of their own, including damage to their shoulders during birth; breathing problems and hypoglycemia after birth because of their own increased insulin production, Schwartz et al., above. Further, babies with excess insulin become children who are at risk for obesity and adults who are at risk for Type II diabetes.

Currently, treatment of diabetes during pregnancy is geared toward keeping blood sugar levels below hyperglycemic levels using special meal plans, scheduled physical activity and, if necessary, insulin injections. Monitoring of blood glucose levels after meals is also recommended. Recently, however, it has been suggested that overzealous control of hyperglycemia in pregnancy may lead to hypoglycemic episodes for the mother, Rosenn et al. (2000) *J Matern Fetal Med* 9:29-34, which is incorporated herein by reference in its entirety. As noted above, maternal hypoglycemia is associated with a variety of problems for the fetus including intrauterine growth retardation, high rates of gestational age-specific neonatal mortality, long term cognitive deficits, increased risk of coronary artery disease, diabetes and hypertension as an adult, Rosenn et al., above. Thus, ideally, blood sugar levels during pregnancy are controlled such that the mother is neither hypoglycemic nor hyperglycemic. Using the methods described herein, which allow for frequent monitoring of blood glucose levels, allows for frequent evaluation of blood glucose levels so that the mother can take appropriate action when either hyperglycemia or hypoglycemia are imminent.

XXVIII. Weight Management

Obesity is a major health problem in many countries and is associated with an increased risk for heart disease, certain cancers and development of Type II diabetes. According to the Centers for Disease Control's (CDC's) National Center for Health Statistics, 54% of adult Americans and between 11% and 14% of children were overweight in 1997, as determined using the Body Mass Index scale, which defines classes of non-obesity and obesity. According to guidelines proposed by the World Health Organization, individuals whose BMI is greater than 25 kg/m$^2$ are Grade 1 overweight. Those whose BMI is greater than 30 kg/m$^2$ are Grade 2 overweight, or obese, and individuals with a BMI greater than 40 kg/m$^2$ are Grade 3 overweight, or morbidly obese (Kopelman (2000) *Nature* 404: 635-643, which is incorporated herein by reference in its entirety).

According to the CDC, the average American woman is 5'3¾" tall, weighs 152 pounds, and has a BMI slightly greater than 26. A woman of the same height, but whose weight was 231 pounds, would have a BMI of 40 kg/m$^2$. As a person's body mass index increases past 30 kg/m$^2$, the risk of acquiring Type II diabetes increases sharply. The relative risk of developing Type II diabetes increases with increasing Body Mass Index (BMI). BMI is measured in kg/m$^2$. Accordingly to Kopelman (*Nature* 404: 635-643, 2000, which is incorporated herein by reference in its entirety), obesity is now so common within the world's population that it is beginning to replace under-nutrition and infectious diseases as the most significant contributor to ill health. Obesity is associated with diabetes mellitus, coronary heart disease, certain forms of cancer, and sleep-breathing disorders. Obesity is generally defined by a body-mass index (weight divided by square of the height) of 30 kg m$^{-2}$ or greater. This degree of obesity takes into account neither the morbidity/mortality associated with more modest degrees of a person (or animal) being overweight, nor the detrimental effect of intra-abdominal fat.

Thus, impaired glucose tolerance is a clear risk factor for Type II diabetes. A survey of American adults performed by the World Health Organization found impaired glucose tolerance in 10%-15% of the study populations. According to the Merck Manual (17$^{th}$ edition), weight loss and exercise are part of the recommended standard treatment for subjects with impaired glucose tolerance or Type II diabetes, and the condition can resolve following weight loss. Furthermore, a recent study correlated weight loss in subjects with impaired glucose tolerance and determined that weight loss can also prevent Type II diabetes from developing in the first place (Eriksson J et al. (1999) *Diabetologia* 42(7): 793-801, which is incorporated herein by reference in its entirety).

One weight loss program involves eating meals that balance the amounts of protein, fat and carbohydrate. See, e.g., Dr. Barry Sears, *Enter the Zone* (1995), Regan Books, which is incorporated herein by reference in its entirety. This diet, which is similar to that suggested for diabetic subjects, seeks to maintain blood glucose levels within specified ranges by limiting the amount of carbohydrate and fat intake and "balancing" fats and carbohydrates with proteins. Thus, frequent monitoring of blood glucose levels allows subjects following this diet to determine which foods (and what combinations of foods) to eat at what times so they maintain specified blood glucose levels that are neither hyperglycemic nor hypoglycemic.

In sum, using the methods described herein provides an excellent means for (1) demonstrating the need to reduce weight; (2) providing instant evidence of the deleterious effects of obesity; and (3) aiding dieters to monitor blood glucose levels and maintain normal levels by eating appropriately. Isolated finger stick procedures performed during occasional medical exams will most likely not have such an impact. Frequent reminders—be they weekly, monthly, daily or more—of abnormal blood glucose levels, in addition to a thorough education on the potential complications of the condition, will stand a greater chance of inspiring change. The methods described herein can be applied to weight gain, or weight maintenance as well.

Accordingly, in one aspect of the present invention a range of glucose values can be established for a subject based on desired blood glucose levels directed to the desired goal, for example, weight management. Alerts can be set in the glucose monitoring device to be activated when blood sugar levels falls below, or rise above, lower and upper limits (respectively) of the predetermined range. Such alerts provide an on-going assessment of the subject's glucose consumption and production, as well as rates and amounts thereof. Frequent and periodic monitoring of changes in the plasma or blood glucose in a subject provides information to the subject and/or health care profession (e.g., physician, dietician, etc.) that allows optimization of a food plan to suit the particular needs of the subject (for example, weight loss or weight gain).

An appropriate reference range of glucose values (i.e., a low and high threshold value) is typically determined by a trained, health-care professional. Such a reference range may also include a preferred average glucose value, as well as a preferred range of variation around the average value. Such a determination of reference glucose range is typically based on current physical characteristics of the subject (including, but not limited to, body mass index, percentage body fat, hydration level, etc.) and the subject's goal for weight management (i.e., gain, loss, or maintenance). This reference range is then entered into the glucose monitoring device typically with alerts set at the high and low threshold values. One or more microprocessor component of the glucose monitoring device typically includes an algorithm to maintain a record of all subject glucose values determined by the glucose monitoring device. A memory component of the glucose monitoring device may also store related information entered by a subject, such as, times and amounts of exercise, amounts and types of food, etc. Alternatively, such information may be entered into a system that interfaces with the glucose monitoring device, such as, a personal computer (PC), pocket PC, personal digital assistant (PDA, e.g., Palm Pilot.™. (Palm Inc., Santa Clara, Calif.)).

Accordingly, a record of glucose levels obtained by frequent sampling (for example, the GlucoWatch biographer provides approximately 3 glucose readings per hour) is developed. Typically, a subject enters the time of meals, snacks, or caloric intake and/or output, in order to keep track of glucose levels relative to such events. Regardless of the subject's inputted information, however, the glucose monitoring device alerts the subject to glucose levels outside of the predetermined range. One set of distinctive alerts may be associated with a low threshold glucose level in order to alert the subject to, for example, consume a snack, and another set of distinctive alerts may be associated with levels above the high threshold value to warn the subject of excessive caloric intake. Further, because an ongoing record of glucose levels is maintained by the glucose monitoring device (and/or an associated device) the records developed over days, weeks, months, etc., can be reviewed by a subject and/or a healthcare professional in order to provide appropriate modifications to the food plan. Accordingly, comparing a series of glucose amounts or concentrations as determined by the glucose monitoring device, the record of caloric intake and/or output, and the predetermined reference range of glucose values allows the subject (and/or health-care professional) to evaluate compliance with the reference range of glucose amounts or concentrations that is being used to achieve the weight management goal of the subject. Further, glucose level fluctuations that put the subject at risk can be evaluated and solutions to avoid such fluctuations proposed.

XXIX. Disease and/or Condition Management

A similar approach may be applied to numerous disease states or conditions, e.g., those described above. For example, a subject may enter information (e.g., time of dosing) about medications that are being taken (such as, HIV medications discussed above) and glucose levels can be evaluated relative to such events, i.e., comparing the record of medication to glucose levels. By keeping track of such information it may be possible to avoid HIV drug-related hyperglycemia and its attendant health problems by modifying the subject's dietary intake, perhaps relative to drug dosing times, in order to maintain glucose values within a predetermined reference range (i.e., between high and low threshold values).

Accordingly, by comparing a series of glucose amounts or concentrations in a subject being treated with a pharmaceutical composition (typically comprising at least one non-insulin-containing pharmaceutical compound, further such pharmaceutical compounds typically do not comprise pharmaceuticals used for the treatment of diabetes, rather they are pharmaceutical compounds with associated side-effects on glucose levels) and a reference record of dates/times of treatment with the pharmaceutical, it is possible to evaluate the effect of the pharmaceutical composition on glucose levels in the subject receiving the pharmaceutical composition over time. Further, a reference range of glucose amounts or concentrations that correspond to maintaining a desired range of glucose amounts or concentrations in the subject during a treatment course can be determined by the subject typically in cooperation with a health-care professional. The reference range is typically defined by a high threshold glucose value and a low threshold glucose value. Alerts may be set in the glucose monitoring device to make the subject aware of fluctuations outside of the reference range.

In another aspect, the above-described methods can be applied to a method for improving prognosis and/or reduction of adverse side-effects associated with a disease state or condition in a subject. In this aspect, a reference range of glucose amounts or concentrations is typically determined that corresponds to achieving an improved prognosis or reduction of adverse side-effects associated with said disease state or condition in the subject. The reference range of glucose amounts or concentrations typically comprises a high threshold glucose value and a low threshold glucose value, and further may include a desired average value with a preferred, associated range of variation. The glucose amount or concentration in the subject is monitored using a glucose monitoring device, for example, as described above.

A series of glucose values is obtained over a time course. By comparing the series of glucose amounts or concentrations and the reference range compliance with the reference range of glucose amounts or concentrations to achieve an improved prognosis or reduction of adverse side-effects associated with said disease state or condition in the subject can be evaluated. Clearly such monitoring of glucose levels is necessary and useful in diabetic disease, for example, Type I and Type II diabetes, however, the method is useful when applied to monitoring glucose in disease states or conditions where the primary effect of the disease state or condition is not directly on glucose levels in the subject, numerous such disease states and conditions are outlined above, including, but not limited to cancer remission, infection with human immunodeficiency virus (HIV), infection with Candida, long distance driving, organ transplantation, growth hormone therapy, renal failure, infection with malaria, alcoholism, intense exercise, cardiovascular disease, cystic fibrosis, stroke, and ischemia.

XXX. Exercise

As another example, the above-described method of providing a functional range of glucose values can be extended to endurance exercise and training. Different ranges of glucose can be established by the subject and/or a health-care professional wherein a selected range of glucose values is put into effect in the glucose monitoring device depending on the activity. For example, three reference glucose ranges may be established for a person undertaking an exercise or training program: a resting range of glucose values, where the high and low glucose threshold values are determined to maintain a certain weight, an aerobic-exercise range of glucose values, where the high and low glucose threshold values are determined to maintain optimum performance during aerobic exertion, and a training-exercise range, where most of the activity is not aerobic in nature (e.g., weight training) and the high and low glucose threshold values are determined to maintain optimum performance during the training activity.

A subject may activate a selected set of range values in the glucose monitoring device. A default setting may be selected by the subject to which settings the glucose monitoring device returns after a specified amount of time, or another alert may be programmed to remind the subject to change the selected set of range values after a certain period of time. In this embodiment of the present invention, a record of glucose level variation correlated to activities gives the subject information to evaluate which may reveal particular issues that need to be addressed. For example, consistently low glucose levels during sustained aerobic events may indicate to the subject that such events should be preceded by an increased intake in carbohydrates/fats/proteins. Further, review and evaluation of such a record (obtained over, for example, days, weeks, or months) may allow the subject to modify the intensity, duration, and/or type of exercise in order to maintain appropriate glucose levels throughout the subject's training program, thereby preventing over-exertion and/or reduction of muscle mass.

In an alternative embodiment, high and low glucose threshold values may be established for a reference glucose range. The glucose monitoring device may be worn by the subject in order to obtain frequent, periodic measurements of glucose amount or concentration in the subject. An independent record may be kept by the subject of caloric intake (e.g., meals and snacks) as well as caloric expenditure (e.g., exercise). This independent record can then be compared to the record of glucose values provided by the glucose monitoring device and the reference range of glucose values. Such comparison may be carried out by hand or by a computerized algorithm. In this aspect of the invention, trends of glucose levels can be compared to caloric intake/output and diet and exercise adjusted accordingly to achieve weight management goals. Accordingly, comparing a series of glucose amounts or concentrations as determined by the glucose monitoring device, the record of caloric intake/output, and the predetermined reference range of glucose values allows the subject (and/or health-care professional) to evaluate compliance with the reference range of glucose amounts or concentrations that is being used to achieve the weight management goal of the subject. Such independent record keeping by the subject may be applied to other disease states or conditions described above (e.g., medications, exercise training, long distance driving, etc.).

Following are examples which illustrate procedures for practicing the invention. These examples should not be construed as limiting. All percentages are by weight and all solvent mixture proportions are by volume unless otherwise noted.

EXAMPLE 1

Selection of Sensors

The following are examples of various sensor technologies that may be utilized in practicing the method of the present invention:

Microgravimetric Sensors

Microgravimetric sensors are based on the preparation of polymeric- or biomolecule-based sorbents that are selective for a particular analyte, such as glucose. A direct measurement of mass changes induced by binding of a sorbent with glucose can be observed by the propagation of acoustic shear waves in the substrate of the sensor. Phase and velocity of the acoustic wave are influenced by the specific adsorption of glucose onto the sensor surface. Piezoelectric materials, such as quartz ($SiO_2$) or zinc oxide (ZnO), resonate mechanically at a specific ultrasonic frequency when excited in an oscillating field. Electromagnetic energy is converted into acoustic energy, whereby piezoelectricity is associated with the electrical polarization of materials with anisotropic crystal structure. Generally, the oscillation method is used to monitor acoustic wave operation. Specifically, the oscillation method measures the series resonant frequency of the resonating sensor. Types of sensors derived from microgravimetric sensors include quartz crystal microbalance (QCM) devices that apply a thickness-shear mode (TSM) and devices that apply surface acoustic wave (SAW) detection principle. Additional devices derived from microgravimetric sensors include the flexural plate wave (FPW), the shear horizontal acoustic plate (SH-APM), the surface transverse wave (STW) and the thin-rod acoustic wave (TRAW).

Conducting Polymers

Conducting polymer sensors promise fast response time, low cost, and good sensitivity and selectivity. The technology is relatively simple in concept. A conductive material, such as carbon, is homogeneously blended in a non-conducting polymer that is specific for glucose and deposited as a thin film on an aluminum oxide substrate. The films lie across two electrical leads, creating a chemoresistor. As the polymer is subjected to EBC, it expands, increasing the distance between carbon particles, and thereby increasing the resistance. The polymer matrix swells because glucose absorbs into the film to an extent determined by the partition coefficient of the glucose. The partition coefficient defines the equilibrium distribution of glucose between the vapor phase and the condensed phase at a specified temperature. Each individual detector element requires a minimum absorbed amount of glucose to cause a response noticeable above the baseline noise. Sensitivity concentrations are reportedly adequate for some applications (tens of ppm). The technology is very portable (small and low power consumption), relatively fast in response time (less than 1 minute), low cost, and should be rugged and reliable.

Electrochemical Sensors

Electrochemical sensors measure a change in output voltage of a sensor caused by chemical interaction of a target analyte (such as glucose) with the sensor. Certain electrochemical sensors are based on a transducer principle. For example, certain electrochemical sensors use ion-selective electrodes that include ion-selective membranes, which generate a charge separation between the sample and the sensor surface. Other electrochemical sensors use a surface of the electrode as the complexation agent, where a change in the electrode potential relates to the concentration of the target analyte. Further examples of electrochemical sensors are based on semiconductor technology for monitoring charges at the surface of an electrode that has been built up on a metal gate between the so-called source and drain electrodes. The surface potential varies with the target analyte concentration.

Additional electrochemical sensor devices include amperometric, conductometric, and capacitive immunosensors. Amperometric immunosensors are designed to measure a current flow generated by an electrochemical reaction at a constant voltage. Generally, electrochemically active labels directly, or as products of an enzymatic reaction, are needed for an electrochemical reaction of a target analyte (such as glucose) at a sensing electrode. Any number of commonly available electrodes can be used in amperometric immunosensors, including oxygen and $H_2O_2$ electrodes.

Capacitive immunosensors are sensor-based transducers that measure the alteration of the electrical conductivity in a solution at a constant voltage, where alterations in conductivity are caused by biochemical enzymatic reactions, which specifically generate or consume ions. Capacitance changes are measured using an electrochemical system, in which a bioactive element is immobilized onto a pair of metal electrodes, such as gold or platinum electrodes.

Conductometric immunosensors are also sensor-based transducers that measure alteration of surface conductivity. As with capacitive immunosensors, bioactive elements are immobilized on the surface of electrodes. When the bioactive element interacts with a target analyte (such as glucose), it causes a decrease in the conductivity between the electrodes.

Electrochemical sensors are excellent for detecting low parts-per-million concentrations. They are also rugged, draw little power, linear and do not require significant support electronics or vapor handling (pumps, valves, etc.) They are moderate in cost ($50 to $200 in low volumes) and small in size.

Regardless of the specific electrochemical technique used to measure glucose concentrations in the EBC, glucose concentrations in EBC can be determined based either on its total mass in the sample or on its concentration. If the sample volume can be controlled accurately, for example, by hydration of a dehydrated hydrogel containing the glucose-binding molecule (such as an enzyme) and any necessary cofactors, then detecting the total quantity of glucose present allows one to calculate its concentration in the original EBC.

This can be accomplished, for example, by utilizing glucose oxidase to convert glucose to gluconolactone and an equivalent amount of hydrogen peroxide. Chronoamperometry can then be used to measure the total current required to oxidize the hydrogen peroxide by-product to $O_2$, and this can be related to the number of moles of hydrogen peroxide present, which is equal to the mass of glucose in the EBC. Complete consumption of the glucose and hydrogen peroxide makes it unnecessary to control the enzyme specific activity or quantity or the reaction time and temperature within narrow limits (provided that sufficient enzyme activity and time is present to allow complete conversion). This is particularly advantageous in sensors designed for use in a wide variety of environmental conditions.

Gas Chromatography/Mass Spectrometry (GC/MS)

Gas Chromatography/Mass Spectrometry (GC/MS) is actually a combination of two technologies. One technology separates the chemical components (GC) while the other one detects them (MS). Technically, gas chromatography is the physical separation of two or more compounds based on their differential distribution between two phases, the mobile phase and stationary phase. The mobile phase is a carrier gas that moves a vaporized sample through a column coated with a stationary phase where separation takes place. When a separated sample component elutes from the column, a detector converts the column eluent to an electrical signal that is measured and recorded. The signal is recorded as a peak in the chromatogram plot. Chromatograph peaks can be identified from their corresponding retention times. The retention time is measured from the time of sample injection to the time of the peak maximum, and is unaffected by the presence of other sample components. Retention times can range from seconds to hours, depending on the column selected and the component. The height of the peak relates to the concentration of a component in the sample mixture.

After separation, the chemical components need to be detected. Mass spectrometry is one such detection method, which bombards the separated sample component molecules with an electron beam as they elute from the column. This causes the molecules to lose an electron and form ions with a positive charge. Some of the bonds holding the molecule together are broken in the process, and the resulting fragments may rearrange or break up further to form more stable fragments. A given compound will ionize, fragment, and rearrange reproducibly under a given set of conditions. This makes identification of the molecules possible. A mass spectrum is a plot showing the mass/charge ratio versus abundance data for ions from the sample molecule and its fragments. This ratio is normally equal to the mass for that fragment. The largest peak in the spectrum is the base peak. The GC/MS is accurate, selective and sensitive.

Infrared Spectroscopy (FTIR, NDIR)

Infrared (IR) spectroscopy is one of the most common spectroscopic techniques used by organic and inorganic chemists. Simply, it is the absorption measurement of different IR frequencies by a sample positioned in the path of an IR beam. IR radiation spans a wide section of the electromagnetic spectrum having wavelengths from 0.78 to 1000 micrometers (microns). Generally, IR absorption is represented by its wave number, which is the inverse of its wavelength times 10,000. For a given sample to be detected using IR spectroscopy, the sample molecule must be active in the IR region, meaning that the molecule must vibrate when exposed to IR radiation. Several reference books are available which contain this data, including the Handbook of Chemistry and Physics from the CRC Press.

There are two general classes of IR spectrometers—dispersive and non-dispersive. In a typical dispersive IR spectrometer, radiation from a broadband source passes through the sample and is dispersed by a monochromator into component frequencies. The beams then fall on a detector, typically a thermal or photon detector, which generates an electrical signal for analysis. Fourier Transform IR spectrometers (FTIR) have replaced the dispersive IR spectrometer due to their superior speed and sensitivity. FTIR eliminates the physical separation of optical component frequencies by using a moving mirror Michelson interferometer and taking the Fourier transform of the signal.

Conversely, in the non-dispersive IR (NDIR) spectrometer, instead of sourcing a broad IR spectrum for analyzing a range of sample gases, the NDIR sources a specific wavelength which corresponds to the absorption wavelength of the target sample. This is accomplished by utilizing a relatively broad IR source and using spectral filters to restrict the emission to the wavelength of interest. For example, NDIR is frequently used to measure carbon monoxide (CO), which absorbs IR energy at a wavelength of 4.67 microns. By carefully tuning the IR source and detector during design, a high volume production CO sensor is manufactured. This is particularly impressive, as carbon dioxide is a common interferent and has an IR absorption wavelength of 4.26 microns, which is very close to that of CO.

NDIR sensors promise low cost (less than $200), no recurring costs, good sensitivity and selectivity, no calibration and high reliability. They are small, draw little power and respond quickly (less than 1 minute). Warm up time is nominal (less than 5 minutes). Unfortunately, they only detect one target gas. To detect more gases additional spectral filters and detectors are required, as well as additional optics to direct the broadband IR source.

Ion Mobility Spectrometry (IMS)

Ion Mobility Spectrometry (IMS) separates ionized molecular samples on the basis of their transition times when subjected to an electric field in a tube. As the sample is drawn into the instrument, it is ionized by a weak radioactive source. The ionized molecules drift through the cell under the influence of an electric field. An electronic shutter grid allows periodic introduction of the ions into the drift tube where they separate based on charge, mass, and shape. Smaller ions move faster than larger ions through the drift tube and arrive at the detector sooner. The amplified current from the detector is measured as a function of time and a spectrum is generated. A microprocessor evaluates the spectrum for the target compound, and determines the concentration based on the peak height.

IMS is an extremely fast method and allows near real time analysis. It is also very sensitive, and should be able to measure all the analytes of interest. IMS is moderate in cost (several thousand dollars) and larger in size and power consumption.

Metal Oxide Semiconductor (MOS) Sensors

Metal Oxide Semiconductor (MOS) sensors utilize a semiconducting metal-oxide crystal, typically tin-oxide, as the sensing material. The metal-oxide crystal is heated to approximately 400° C., at which point the surface adsorbs oxygen. Donor electrons in the crystal transfer to the adsorbed oxygen, leaving a positive charge in the space charge region. Thus, a surface potential is formed, which increases the sensor's resistance. Exposing the sensor to deoxidizing, or reducing, gases removes the surface potential, which lowers the resistance. The end result is a sensor which changes its electrical resistance with exposure to deoxidizing gases. The change in resistance is approximately logarithmic.

MOS sensors have the advantage of being extremely low cost (less than $8 in low volume) with a fast analysis time (milliseconds to seconds). They have long operating lifetimes (greater than five years) with no reported shelf life issues.

Thickness-Shear Mode Sensors (TSM)

TSM sensors consist of an AT-cut piezoelectric crystal disc, most commonly of quartz because of its chemical stability in biological fluids and resistance to extreme temperatures, and two electrodes (preferably metal) attached to opposite sides of the disc. The electrodes apply the oscillating electric field. Generally, TSM sensor devices are run in a range of 5-20 MHz. Advantages are, besides the chemical inertness, the low cost of the devices and the reliable quality of the mass-produced quartz discs.

Photo-Ionization Detectors (PID)

Photo-Ionization Detectors rely on the fact that all elements and chemicals can be ionized. The energy required to displace an electron and 'ionize' a gas is called its Ionization Potential (IP), measured in electron volts (eV). A PID uses an ultraviolet (UV) light source to ionize the gas. The energy of the UV light source must be at least as great as the IP of the sample gas. For example, benzene has an IP of 9.24 eV, while carbon monoxide has an IP of 14.01 eV. For the PID to detect the benzene, the UV lamp must have at least 9.24 eV of energy. If the lamp has an energy of 15 eV, both the benzene and the carbon monoxide would be ionized. Once ionized, the detector measures the charge and converts the signal information into a displayed concentration. Unfortunately, the display does not differentiate between the two gases, and simply reads the total concentration of both summed together.

Three UV lamp energies are commonly available: 9.8, 10.6 and 11.7 eV. Some selectivity can be achieved by selecting the lowest energy lamp while still having enough energy to ionize the gases of interest. The largest group of compounds measured by a PID are the organics (compounds containing carbon), and they can typically be measured to parts per million (ppm) concentrations. PIDs do not measure any gases with an IP greater than 11.7 eV, such as nitrogen, oxygen, carbon dioxide and water vapor. The CRC Press Handbook of Chemistry and Physics includes a table listing the IPs for various gases.

PIDs are sensitive (low ppm), low cost, fast responding, portable detectors. They also consume little power.

Surface Acoustic Wave Sensors (SAW)

Surface Acoustic Wave (SAW) sensors are constructed with interdigitated metal electrodes fabricated on piezoelectric substrates both to generate and to detect surface acoustic waves. Surface acoustic waves are waves that have their maximum amplitude at the surface and whose energy is nearly all contained within 15 to 20 wavelengths of the surface. Because the amplitude is a maximum at the surface such devices are very surface sensitive. Normally, SAW devices are used as electronic bandpass filters in cell phones. They are hermetically packaged to insure that their performance will not change due to a substance contacting the surface of the SAW.

SAW chemical sensors take advantage of this surface sensitivity to function as sensors. To increase specificity for specific compounds, SAW devices are frequently coated with a thin polymer film that will affect the frequency and insertion loss of the device in a predictable and reproducible manner. Each sensor in a sensor array is coated with a different polymer and the number and type of polymer coating are selected based on the number and type of chemicals to be detected. If the device with the polymer coating is then subjected to chemical fluids that absorb into the polymer material, then the frequency and insertion loss of the device will further change. It is this final change that allows the device to function as a chemical sensor.

SAW sensors are reasonably priced (less than $200) and have good sensitivity (tens of ppm) with very good selectivity. They are portable, robust and consume nominal power. They warm up in less than two minutes and require less than one minute for most analysis. They are typically not used in high accuracy quantitative applications, and thus require no calibration. SAW sensors do not drift over time, have a long operating life (greater than five years) and have no known shelf life issues.

Amplifying Fluorescent Polymer Technology

Sensors can use fluorescent polymers that react with volatile chemicals as sensitive target analyte (such as glucose) detectors. Conventional fluorescence detection normally measures an increase or decrease in fluorescence intensity or an emission wavelength shift that occurs when a single molecule of the target analyte interacts with an isolated chromophore, where the chromophore that interacts with the target analyte is quenched; the remaining chromophores continue to fluoresce.

A variation of this approach is the "molecular wire" configuration, as described by Yang and Swager, *J. Am. Chem. Soc.*, 120:5321-5322 (1998) and Cumming et al., *IEEE Trans Geoscience and Remote Sensing*, 39:1119-1128 (2001), both of which are incorporated herein by reference in their entirety. In the molecular wire configuration, the absorption of a single photon of light by any chromophore will result in a chain reaction, quenching the fluorescence of many chromophores and amplifying the sensory response by several orders of magnitude.

Fiber Optic Microsphere Technology

Fiber optic microsphere technology is based upon an array of a plurality of microsphere sensors (beads), wherein the microspheres are associated with a target analyte (such as glucose) and are placed on an optical substrate containing a plurality of micrometer-scale wells (see, for example, Michael et al., *Anal Chem*, 71:2192-2198 (1998); Dickinson et al., *Anal Chem.*, 71:2192-2198 (1999); Albert and Walt, *Anal Chem*, 72:1947-1955 (2000); and Stitzel et al., *Anal Chem*, 73:5266-5271 (1001), all of which are incorporated herein by reference in their entirety). The beads can be encoded with unique signatures to identify the bead as well as its location. Upon exposure to a target analyte (such as glucose), the beads respond to the target analyte and their intensity and wavelength shifts are used to generate fluorescence response patterns, which are, in turn, used to calculate the concentration of the analyte.

Interdigitated Microelectrode Arrays (IME)

Interdigitated microelectrode arrays are based on the used of a transducer film that incorporates an ensemble of nanometer-sized metal particles, each coated by an organic monomolecular layer shell (see, for example, Wohltjen and Snow, *Anal Chem*, 70:2856-2859 (1998); and Jarvis et al., *Proceedings of the 3$^{rd}$ Intl Aviation Security Tech Symposium*, Atlantic City, N.J., 639-647 (2001), both of which are incorporated herein by reference in their entirety). Such sensor devices are also known as metal-insulator-metal ensembles (MIME) because of the combination of a large group of colloidal-sized, conducting metal cores separated by thin insulating layers.

Microelectromechanical Systems (MEMS)

Sensor technology based on MEMS integrate mechanical elements, sensors, actuators, and electronics on a common silicon substrate for use in detecting target analytes (see, for example, Pinnaduwage et al., *Proceedings of 3$^{rd}$ Intl Aviation Security Tech Symposium*, Atlantic City, N.J., 602-615 (2001); and Lareau et al., *Proceedings of 3$^{rd}$ Intl Aviation Security Tech Symposium*, Atlantic City, N.J., 332-339 (2001), both of which are incorporated herein by reference in their entirety).

One example of sensor technology based on MEMS is microcantilever sensors. Microcantilever sensors are hairlike, silicon-based devices that are at least 1,000 times more sensitive and smaller than currently used sensors. The working principle for most microcantilever sensors is based on a measurement of displacement. Specifically, in biosensor applications, the displacement of a cantilever-probe is related to the binding of molecules on the (activated) surface of the cantilever beam, and is used to compute the strength of these bonds, as well as the presence of specific reagents in the solution under consideration (Fritz, J. et al., "Translating biomolecular recognition into nanomechanics," *Science*, 288: 316-318 (2000); Raiteri, R. et al., "Sensing of biological substances based on the bending of microfabricated cantilevers," *Sensors and Actuators B*, 61:213-217 (1999), both of which are incorporated herein by reference in their entirety). It is clear that the sensitivity of these devices strongly depends on the smallest detectable motion, which poses a constraint on the practically vs. theoretically achievable performance.

One example of microcantilever technology uses silicon cantilever beams (preferably a few hundred micrometers long and 1 μm thick) that are coated with a different sensor/detector layer (such as antibodies or aptamers). When exposed to a target analyte (such as glucose), the cantilever surface absorbs the target analyte, which leads to interfacial stress between the sensor and the absorbing layer that bends the cantilever.

Microcantilever sensors are highly advantageous in that they are rugged, reusable, and extremely sensitive, yet they cost little and consume little power.

Molecularly Imprinted Polymeric Film

Molecular imprinting is a process of template-induced formation of specific molecular recognition sites (binding or catalytic) in a polymeric material where the template directs the positioning and orientation of the polymeric material's structural components by a self-assembling mechanism (see, for example, Olivier et al., *Anal Bioanal Chem*, 382:947-956 (2005); and Ersoz et al., *Biosensors & Bioelectronics*, 20:2197-2202 (2005), both of which are incorporated herein by reference in their entirety). The polymeric material can include organic polymers as well as inorganic silica gels. Molecularly imprinted polymers (MIPs) can be used in a variety of sensor platforms including, but not limited to, fluorescence spectroscopy; UV/Vis spectroscopy; infrared spectroscopy; surface plasmon resonance; chemiluminescent adsorbent assay; and reflectometric interference spectroscopy. Such approaches allow for the realization of highly efficient and sensitive target analyte recognition.

EXAMPLE 2

Detection of Glucose in Exhaled Breath

Persons with diabetes presently check their blood glucose levels between 1 and 6-8 times each day. Knowledge of blood glucose levels is an absolute necessity for guiding proper administration and dosing of insulin and other medications used to control hyperglycemia. Presently the person must draw blood samples, usually from a finger using a lancet device, and place the sample on a "test strip" which is inserted into a glucose monitor that gives the blood glucose concentration. This process requires considerable skill, time and subjects the person with diabetes to immediate recognition as a diabetic and thus results in the potential for embarrassment and even prejudice and/or discrimination when applying for employment.

An attractive alternative is to use a sensor system that collects a sample of exhaled breath which for compounds such as glucose, which are extremely hydrophilic, condenses the sample into a "condensate" which is then placed in contact with the sensor by a pump or microfluidic system. Thus, persons with diabetes are far more likely to inconspicuously blow into a small hand-held device that provides a blood glucose concentration from an exhaled breath sample then to perform the multiple steps required for a blood sample, particularly in public places. This technology is likely to increase the acceptance of frequent blood glucose monitoring and reduce the embarrassment that many persons with diabetes feel when having to draw blood samples from their fingers. Further, because of the accuracy and non-invasive nature of the subject glucose monitoring system, it is a far more attractive system than the current blood sampling techniques, which have been shown to be only marginally reliable (as the blood-test strips are prone to error due to temperature, poor user technique and short shelf life and human factors related errors).

EXAMPLE 3

Correlation of Glucose in Exhaled Breath with Glucose in Blood

Figure 3A:
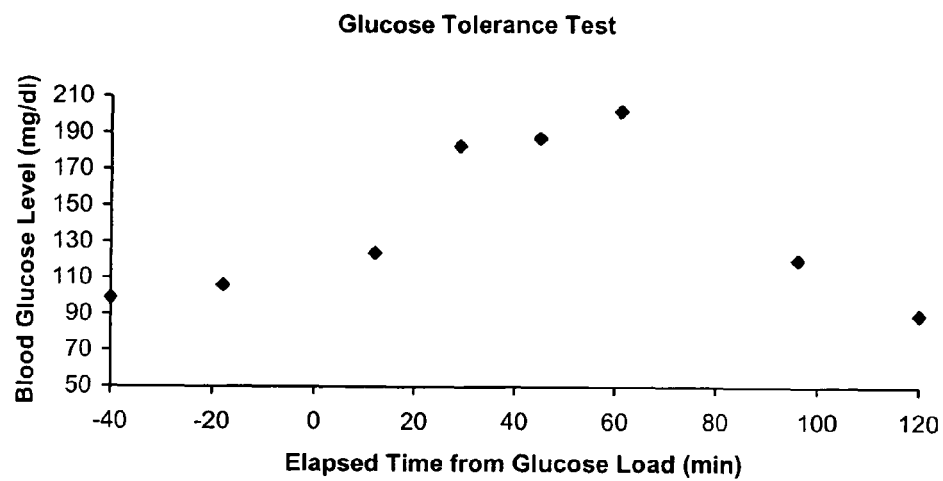
FIGS. 3A and 3B illustrate the blood (8a) and breath (8b) concentrations of glucose over time after the ingestion of a 100 gm glucose solution.
Figure 3B:
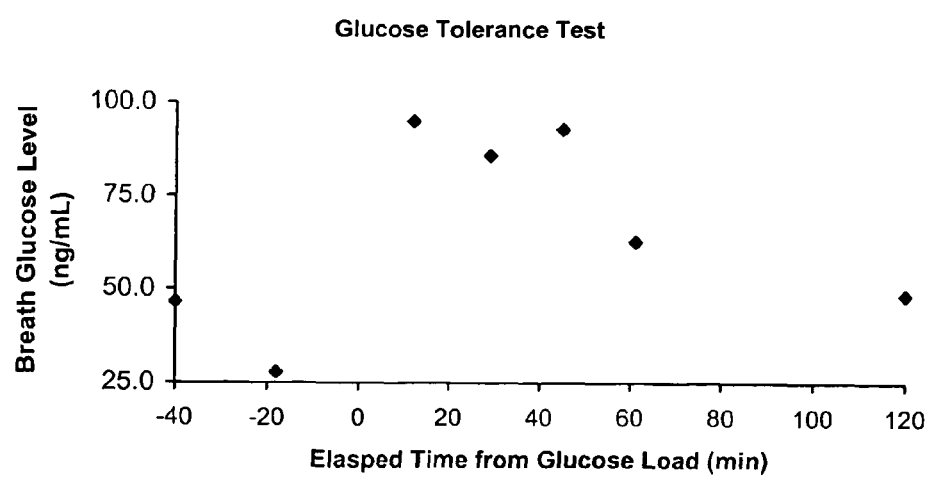

A non-diabetic subject ingested a 100 gm glucose solution. Both exhaled breath and blood samples were taken from the subject at 40 and 20 minutes before ingestion of the glucose solution and for 10 minutes interval every 15 minutes, see FIGS. 3A and 3B, after ingestion of the glucose solution. Glucose was readily detectable in the exhaled breath, which was condensed into a liquid. The concentration of both the breath and blood glucose rose and fell at the same rates (see FIGS. 3A and 3B).

According to the subject invention, the ratio of exhaled breath to blood glucose concentration is 3 to 5 magnitudes lower and that this ratio is predictable and reproducible. By analyzing glucose present in EBC, a more predictive, non-invasive, and simpler method is provided to monitor glucose concentration in a subject by monitoring breath rather than blood.

EXAMPLE 4

Measurement of Blood Glucose and Lactic Acid Concentrations in the Operating Room During Surgical Procedures Using Exhaled Breath An elderly subject with a history of insulin dependent diabetes (Type I) requires a serious operation in which significant blood loss is anticipated. As part of the routine monitoring of the subject, the anesthesiologist continuously monitors exhaled breath glucose and lactic acid. Several recent medical research studies have shown that tight control of glucose in the normal range improves outcome, wound healing and rate of post-operative infection in persons with diabetes. Presently, the anesthesiologist can only monitor blood glucose intermittently by drawing blood samples. These results guide the administration of insulin. Excessive doses can lead to hypoglycemia, with disastrous consequences and inadequate doses can lead to hyperglycemia, which can result in intra- and post-operative complications. Exhaled breath affords the potential of continuous tight glucose control without the potential for either hyperglycemia or hypoglycemia. In fact, a "closed loop" system is possible where the exhaled breath glucose concentration is used to control and insulin infusion, thus freeing the anesthesiologist of having to give boluses of insulin.

In addition to monitoring glucose continuously, the anesthesiologist monitors exhaled breath lactic acid to determine whether there is excessive blood loss or other reasons for decrease perfusion of vital organs. Presently, blood pressure, heart rate and, on occasions, central venous pressure are used to monitor subjects for blood loss with resulting hypovolemia and diminished perfusion. This in turn leads to lactic acidosis, an ominous complication, but presently lactic acid can only be measured intermittently from blood samples. By continuously monitoring lactic acid levels in EBC, the anesthesiologist will have a much better means of determining if there is hypoperfusion of vital organs. Thus, measurement of compounds continuously in exhaled breath in either the gaseous or condensed state can lead to marked improvement in monitoring, and therefore, treatment of subjects in the operating room and the intensive care unit.

Continuous or frequent monitoring of EBC glucose and lactic acid has broad application for evaluating the status of world class athletes and war fighters, especially special forces personnel.

EXAMPLE 5

Detection and Correlation of Glucose in EBC to Blood Concentrations

A sensor of the invention can include an appropriate hydrogel monomer (such as HEMA—hydroxyethylmethacrylate, or PVA—polyvinyl alcohol) that was polymerized in the presence of an appropriate enzyme specific for glucose (such as glucose hexokinase [GHK] or dehydrogenase [GDH]) and other compounds necessary for an amperometric reading of glucose concentration (including pyrroloquinoline [PQQ] and ferricyanide). Hydrogels are polymers that contain large voids that can be filled with water and other water soluble compounds. Hydrogels can be made with a wide range of water to hydrogel ratios and the polymer can contain up to about 99% water, preferably up to about 80% water.

The subject amperometric technique for detecting glucose in EBC allows for complete consumption of the glucose present in the sample to determine the glucose concentration. This is an advanced form of glucose measurements that measures total glucose consumption rather than enzymatic kinetics.

Glucose, in the presence of PQQ and GDH is catalyzed to gluconic acid and the reduced form of PQQ-PQQH$_2$. The PQQH$_2$ then reacts with the ferricyanide in the of GDH to ferrocyanide and PQQ. The ferrocyanide then gives off an electron and returns to ferricyanide.

In a preferred embodiment, the enzyme and additional compounds are cross-linked in the hydrogel and are present in sufficient quantity to be in excess of any glucose concentration present in the EBC. The hydrogel-enzyme complex is freeze dried onto an appropriate surface, such as the inside of a collection reservoir or a tube that a patient could blow through. Appropriate circuitry is placed in the tube below the freeze dried hydrogel complex in order to measure the current generated when the glucose from the sample is introduced to the hydrogel complex. In certain embodiments, appropriate electrolyte sensing electrodes (i.e. $K^+$, $Na^+$, or $Cl^-$) are placed above the hydrogel, which would contact the surface of the hydrogel when it has fully swelled. These electrodes would serve two purposes, to determine when the hydrogel was fully swelled and to determine appropriate electrolyte concentration.

On the outside of the collection reservoir or tube (or within the walls or surface of the collection reservoir or tube) is commercially available technology that is able to selectively cool or heat the collection reservoir or tube in the area where the hydrogel has been deposited. One such device is a Peltier device, which can be heated or cooled rapidly. According to the subject invention, when the subject blows into the collection reservoir or tube, the Peltier is also cooling the collection reservoir or tube. This increases the condensation of breath on the hydrogel, which if applied in a thin layer, will rapidly swell to maximum hydration. Since the hydrogel can only swell to a known quantity based on its formulation, a precise amount of EBC containing glucose will be absorbed by the hydrogel. Complete absorption and swelling will be detected by the electrodes above the hydrogel.

At that point, a signal will alert the subject to stop blowing into the collection reservoir or tube and the Peltier will warm to a temperature that will optimize the rate of the enzymatic reaction. Simultaneously the electrodes will measure the appropriate electrolyte to determine whether the sample has been diluted or concentrated and an appropriate "dilution factor" can be calculated.

The enzymatic reaction will be allowed to proceed to completion and the glucose concentration in the EBC will be calculated by integrating the "area under the curve" of the current generated during consumption of glucose by the enzyme and its conversion to $H_2O_2$. Such methods are well-known to the skilled artisan for calculating total concentration or other values. With compensation for any dilution, the EBC glucose concentration will be used to calculate the blood glucose concentration. In certain embodiments, EBC glucose concentration can be used to calculate blood glucose concentration using a conveniently available table or other means of calculating blood glucose concentration (such as calculator, etc.).

It should be understood that the examples and embodiments described herein are for illustrative purposes only and that various modifications or changes in light thereof will be suggested to persons skilled in the art and are to be included within the spirit and purview of this application and the scope of the appended claims. Specifically, the glucose detection method of the present invention is intended to cover detection not only through the exhalation by a subject with a device utilizing enzyme-based sensor technology, but also other suitable technologies, such as gas chromatography, transcutaneous/transdermal detection, semiconductive gas sensors, mass spectrometers, IR or UV or visible or fluorescence spectrophotometers.

All patents, patent applications, provisional applications, and publications referred to or cited herein, or from which a claim for benefit of priority has been made, are incorporated by reference in their entirety to the extent they are not inconsistent with the explicit teachings of this specification.

We claim:

1. A non-invasive, portable glucose monitoring device comprising:
   a) at least one collection reservoir for collecting at least one exhaled breath sample, wherein said collection reservoir comprises a sensor and a signaling means, said sensor, said signaling means or both either comprising or being in operative communication with at least one processor; and
   b) a means for extracting condensates from the exhaled breath sample, wherein said sensor is equipped to identify glucose and at least one solute in the extracted condensate, and where the concentration of said at least one solute, the concentration of which is both tightly regulated in blood and which concentration is substantially identical in airway lining fluid to that in blood, is used by said processor as a ratio with the concentration of that same solute in blood to determine a dilution factor to be utilized in correlating the concentration of glucose in blood with the glucose identified in the extracted condensate by multiplying said dilution factor with the concentration of glucose in said condensate.

2. The device of claim 1, wherein the collection reservoir is comprised within at least one breathing tube.

3. The device of claim 2, wherein the at least one breathing tube is disposable.

4. The device of claim 2, comprising a plurality of breathing tubes that are provided in a collapsed state.

5. The device of claim 1, wherein the sensor comprises a hydrophilic hydrogel comprising at least one glucose-binding molecule.

6. The device of claim 5, wherein the glucose-binding molecule is selected from the group consisting of: antibodies, enzymes, oligonucleotides, peptides, or proteins.

7. The device of claim 6, wherein the glucose-binding molecule is selected from the group consisting of glucose-oxidase, glucose dehydrogenase, and glucose hexokinase.

8. The device of claim 5, further comprising a pressure transducer near the hydrogel.

9. The device of claim 1, wherein the means for extracting condensates comprises a Peltier device, which surrounds the collection reservoir or is otherwise in sufficient contact to achieve control over the temperature of said collection reservoir.

10. The device of claim 1, wherein the sensor is equipped to identify chloride or other electrolytes, and wherein the sensor comprises one sensor for identifying glucose and chloride, or other electrolytes, or a first sensor for identifying glucose and a second sensor for identifying chloride or other electrolytes.

11. The device of claim 1, wherein the sensor further comprises a calibration sensor.

12. The device according to claim 1 which detects the glucose concentration in a subject at risk of hyperglycemia, hypoglycemia or fluctuations between hyperglycemia and hypoglycemia.

13. The device according to claim 12 which detects blood glucose levels at frequent intervals or constantly over a period of time.

14. The non-invasive, portable glucose monitoring device according to claim 1 wherein said airway lining fluid is comprised predominantly from alveolar lining fluid, fluid from capillary endothelial cells, and combinations thereof and wherein said solute is chloride.

15. A glucose monitoring device comprising:
   (a) at least one collection reservoir for collecting at least one exhaled breath sample,
   (b) at least one sensor, coupled to at least one signaling means, said sensor or said signaling means or both comprising or being in operative communication with at least one processor; and
   (c) a means for extracting condensate from said at least one exhaled breath sample;

wherein said condensate is contacted with said at least one sensor;

wherein said at least one sensor is adapted to measure the concentration of glucose in said condensate and to measure the concentration of at least one solute other than glucose in said condensate such that the concentration of said at least one solute, the concentration of which is both tightly regulated in blood and which concentration is substantially identical in airway lining fluid to that in blood, is used by said processor as a ratio with the concentration of that same at least one solute in blood to determine a dilution factor which is utilized by said processor to multiply said dilution factor with the concentration of glucose measured in said condensate by said sensor, to thereby provide the concentration of glucose in blood wherein said means for extracting condensate from said at least one exhaled breath sample extracts condensate by cooling said at least one exhaled breath sample to a temperature below body temperature wherein said temperature below body temperature is a temperature selected from the group consisting of between 10 to 15 degrees Centigrade below body temperature.

16. A glucose monitoring device comprising:
(a) at least one collection reservoir for collecting at least one exhaled breath sample,
(b) at least one sensor, coupled to at least one signaling means, said sensor or said signaling means or both comprising or being in operative communication with at least one processor; and
(c) a means for extracting condensate from said at least one exhaled breath sample;
wherein said condensate is contacted with said at least one sensor;
wherein said at least one sensor is adapted to measure the concentration of glucose in said condensate and to measure the concentration of at least one solute other than glucose in said condensate such that the concentration of said at least one solute, the concentration of which is both tightly regulated in blood and which concentration is substantially identical in airway lining fluid to that in blood, is used by said processor as a ratio with the concentration of that same at least one solute in blood to determine a dilution factor which is utilized by said processor to multiply said dilution factor with the concentration of glucose measured in said condensate by said sensor, to thereby provide the concentration of glucose in blood, wherein said means for extracting condensate from said at least one exhaled breath sample extracts condensate by cooling said at least one exhaled breath sample to a temperature below body temperature wherein said temperature below body temperature is a temperature selected from the group consisting of 20.6 degrees centigrade, −2.8 degrees centigrade, and −17.8 degrees centigrade.

17. The glucose monitoring device according to claim 16 wherein said airway lining fluid is comprised predominantly from alveolar lining fluid, fluid from capillary endothelial cells, and combinations thereof and wherein said solute is chloride.

18. A glucose monitoring device comprising:
(a) at least one collection reservoir for extracting and collecting condensate from at least one exhaled breath sample
(b) at least one sensor, coupled to at least one signaling means, said sensor or said signaling means or both comprising or being in operative communication with at least one processor;
wherein said condensate is contacted with said at least one sensor;
wherein said at least one sensor is adapted to measure the concentration of glucose in said condensate and to measure the concentration of at least one solute other than glucose in said condensate such that the concentration of said at least one solute, the concentration of which is both tightly regulated in blood and which concentration is substantially identical in airway lining fluid to that in blood, is used by said processor as a ratio with the concentration of that same at least one solute in blood to determine a dilution factor which is utilized by said processor to multiply said dilution factor with the concentration of glucose measured in said condensate by said sensor, to thereby provide the concentration of glucose in blood.

19. The non-invasive portable glucose monitoring device of claim 18, wherein said at least one sensor comprises a first sensor for identifying glucose and a second sensor for identifying said at least one solute.

20. The device according to claim 19 which detects the glucose concentration in a subject at risk of hyperglycemia, hypoglycemia or fluctuations between hyperglycemia and hypoglycemia.

21. The device according to claim 20 which detects blood glucose levels at frequent intervals or constantly over a period of time.

22. A glucose monitoring device comprising:
(a) at least one collection reservoir for collecting at least one exhaled breath sample,
(b) at least one sensor, coupled to at least one signaling means, said sensor or said signaling means or both comprising or being in operative communication with at least one processor; and
(c) a means for extracting condensate from said at least one exhaled breath sample;
wherein said condensate is contacted with said at least one sensor;
wherein said at least one sensor is adapted to measure the concentration of glucose in said condensate and to measure the concentration of at least one solute other than glucose in said condensate such that the concentration of said at least one solute, the concentration of which is both tightly regulated in blood and which concentration is substantially identical in airway lining fluid to that in blood, is used by said processor as a ratio with the concentration of that same at least one solute in blood to determine a dilution factor which is utilized by said processor to multiply said dilution factor with the concentration of glucose measured in said condensate by said sensor, to thereby provide the concentration of glucose in blood.

23. The device of claim 22 wherein said means for extracting condensate from said at least one exhaled breath sample extracts condensate by cooling said at least one exhaled breath sample to a temperature below body temperature.

24. The device according to claim 22 which detects the glucose concentration in a subject at risk of hyperglycemia, hypoglycemia fluctuations between hyperglycemia and hypoglycemia.

25. The device according to claim 24 which detects blood glucose levels at frequent intervals or constantly over a period of time.

26. The device of claim 23, wherein said means for extracting condensate comprises a Peltier device.

27. The device of claim 22 wherein said at least one exhaled breath sample is an end-tidal exhaled breath sample.

28. The device of claim 22, wherein said at least one sensor comprises a first sensor for identifying glucose and a second sensor for identifying said at least one solute.

29. The device of claim 22 wherein said solute is an electrolyte the concentration of which is measured in said condensate, wherein said electrolyte is selected from the group consisting of chloride, sodium, potassium and combinations thereof.

30. The device of claim 29 wherein the electrolyte, the concentration of which that is measured in said condensate, is chloride.

31. A non-invasive, portable glucose monitoring device comprising at least one processor and at least one collection reservoir for extracting and collecting condensate from at least one exhaled breath sample, wherein said collection reservoir comprises a sensor and a signaling means, wherein said sensor is equipped to identify glucose and at least one solute in the extracted condensate, and where the concentration of said at least one solute, the concentration of which is both tightly regulated in blood and which concentration is substantially identical in airway lining fluid to that in blood, is used by said processor as a ratio with the concentration of that same solute in blood to determine a dilution factor to be utilized in correlating the concentration of glucose in blood with the glucose identified in the extracted condensate by multiplying said dilution factor with the concentration of glucose in said condensate.

32. The non-invasive portable glucose monitoring device of claim 31, wherein said at least one sensor comprises a first sensor for identifying glucose and a second sensor for identifying said at least one solute.

33. A glucose monitoring device comprising:
(a) at least one collection reservoir for collecting at least one exhaled breath sample,
(b) at least one sensor, coupled to at least one signaling means, said sensor or said signaling means or both comprising or being in operative communication with at least one processor; and
(c) a means for extracting condensate from said at least one exhaled breath sample;
wherein said condensate is contacted with said at least one sensor;
wherein said at least one sensor is adapted to measure the concentration of glucose in said condensate and to measure the concentration of at least one solute other than glucose in said condensate such that the concentration of said at least one solute, the concentration of which is both tightly regulated in blood and which concentration is substantially identical in airway lining fluid to that in blood, is used by said processor as a ratio with the concentration of that same at least one solute in blood to determine a dilution factor which is utilized by said processor to multiply said dilution factor with the concentration of glucose measured in said condensate by said sensor, to thereby provide the concentration of glucose in blood wherein said means for extracting condensate from said at least one exhaled breath sample extracts condensate by cooling said at least one exhaled breath sample to a temperature below body temperature.

* * * * *